(12) United States Patent
Agnello

(10) Patent No.: US 10,639,511 B2
(45) Date of Patent: May 5, 2020

(54) ISOMETRIC-EXERCISE TOWEL AND METHODS OF ISOMETRIC EXERCISE

(71) Applicant: Gregory Agnello, New Rochelle, NY (US)

(72) Inventor: Gregory Agnello, New Rochelle, NY (US)

(*) Notice: Subject to any disclaimer, the term of this patent is extended or adjusted under 35 U.S.C. 154(b) by 144 days.

(21) Appl. No.: 15/404,094

(22) Filed: Jan. 11, 2017

(65) Prior Publication Data

US 2018/0193685 A1 Jul. 12, 2018

(51) Int. Cl.

| | | |
|---|---|---|
| A63B 21/002 | (2006.01) | |
| A47K 10/02 | (2006.01) | |
| A63B 23/00 | (2006.01) | |
| A63B 21/00 | (2006.01) | |
| A63B 71/06 | (2006.01) | |

(Continued)

(52) U.S. Cl.
CPC .......... *A63B 21/0023* (2013.01); *A47K 10/02* (2013.01); *A63B 21/00043* (2013.01); *A63B 21/00185* (2013.01); *A63B 21/1645* (2013.01); *A63B 21/4015* (2015.10); *A63B 21/4021* (2015.10); *A63B 21/4025* (2015.10); *A63B 21/4037* (2015.10); *A63B 71/0622* (2013.01); *G16H 20/30* (2018.01); *A63B 2023/006* (2013.01); *A63B 2209/00* (2013.01)

(58) Field of Classification Search
CPC .......... A63B 21/0023; A63B 2023/006; A63B 21/002; A63B 21/00185; A47K 10/02
See application file for complete search history.

(56) References Cited

U.S. PATENT DOCUMENTS

| | | | |
|---|---|---|---|
| 817,263 A | 4/1906 | Murray | |
| 1,990,568 A * | 2/1935 | Scheidler | ............... A47K 7/022 |
| | | | 15/222 |

(Continued)

OTHER PUBLICATIONS

Product Screen on Fletcher Pilates Site, for the Knotted Fletcher Pilates "Towelwork to Go(TM)" Physical Conditioning Towel, circa Jan. 2017, 1 Page.

(Continued)

*Primary Examiner* — Nyca T Nguyen
(74) *Attorney, Agent, or Firm* — Thomas J. Perkowski, Esq., PC

(57) ABSTRACT

An isometric-exercise towel for use in performing isometric exercises, including a layer of moisture-absorbent material having four corners, and a thick pile having moisture-wicking characteristics, a hand/foot-insertable aperture formed in each of the four corners of the isometric-exercise towel. The perimeter of each hand/foot-insertable aperture is reinforced with double stitching, and a reinforced stitching pattern is formed between pairs of hand/foot-insertable apertures formed on opposing ends of the isometric-exercise towel. The hand and/or foot of a person using the isometric-exercise towel, or both hands and/or feet of the person, can be inserted within any one or more of the hand/foot-insertable apertures formed in the isometric-exercise towel so as to perform one or more isometric exercises by the person using his or her hands and/or feet to exert forces against the side inner perimeter surfaces of the hand/foot-insertable apertures of the isometric-exercise towel in an outwardly and isometric manner.

16 Claims, 49 Drawing Sheets

(51) Int. Cl.
*A63B 21/16* (2006.01)
*G16H 20/30* (2018.01)

(56) References Cited

U.S. PATENT DOCUMENTS

| | | | |
|---|---|---|---|
| 2,352,067 A * | 6/1944 | Barr | A47K 10/02 |
| | | | 139/396 |
| 2,544,354 A * | 3/1951 | Reiter | A47K 7/022 |
| | | | 15/222 |
| 2,754,532 A | 7/1956 | Kanehl et al. | |
| 4,224,712 A | 9/1980 | Black et al. | |
| 4,251,070 A | 2/1981 | Leseberg | |
| 4,290,597 A | 9/1981 | Schleffendorf | |
| 4,417,727 A | 11/1983 | Ottenheimer | |
| 4,428,577 A | 1/1984 | Weingardt | |
| 4,489,933 A | 12/1984 | Fisher et al. | |
| 4,497,071 A | 2/1985 | Bell | |
| 4,519,148 A | 5/1985 | Sisco | |
| 4,638,995 A | 1/1987 | Wilson | |
| 4,696,469 A | 9/1987 | Elder | |
| 4,698,854 A | 10/1987 | Slimmon | |
| 4,703,928 A | 11/1987 | Escher | |
| 4,759,543 A | 7/1988 | Feldman | |
| 4,836,530 A | 6/1989 | Stanley | |
| 4,946,453 A | 8/1990 | Monson | |
| 4,993,980 A | 2/1991 | Dulin et al. | |
| 4,998,722 A | 3/1991 | Scott | |
| 5,012,543 A | 5/1991 | Lewis | |
| 5,072,467 A | 12/1991 | Hunt | |
| 5,099,530 A | 3/1992 | Scott | |
| 5,144,694 A | 9/1992 | oud et al. | |
| 5,186,698 A | 2/1993 | Mason et al. | |
| 5,211,598 A | 5/1993 | Hall | |
| 5,242,348 A | 9/1993 | Bates | |
| 5,467,487 A | 11/1995 | Sicard | |
| 5,584,786 A | 12/1996 | Almeda | |
| 5,647,829 A | 7/1997 | Rivas | |
| 5,685,764 A | 11/1997 | Kostritzky | |
| 5,702,324 A | 12/1997 | Wendel et al. | |
| 5,711,747 A | 1/1998 | Steinback | |
| 5,735,776 A | 4/1998 | Swezey et al. | |
| 5,737,773 A | 4/1998 | Dicker et al. | |
| 5,839,122 A | 11/1998 | Dicker et al. | |
| 5,871,424 A | 2/1999 | Conner | |
| 5,893,223 A | 4/1999 | Glass | |
| 5,894,271 A | 4/1999 | Namisniak | |
| 5,978,966 A | 11/1999 | Dicker et al. | |
| 6,036,621 A | 3/2000 | Hancock | |
| 6,047,433 A * | 4/2000 | Chang | A47K 7/022 |
| | | | 15/222 |
| 6,151,715 A | 11/2000 | Doherty | |
| 6,517,471 B2 | 2/2003 | Chen | |
| 6,547,703 B1 | 4/2003 | Swezey et al. | |
| 6,652,421 B1 | 11/2003 | Chen | |
| 6,692,420 B2 | 2/2004 | Walden | |
| 6,712,745 B1 | 3/2004 | Lynne | |
| 6,733,420 B1 | 5/2004 | Schroeder | |
| 6,751,816 B1 | 6/2004 | Wechsler | |
| 6,872,187 B1 | 3/2005 | Stark et al. | |
| 6,881,179 B2 | 4/2005 | Mostardi | |
| 6,913,559 B2 | 7/2005 | Smith | |
| 6,979,282 B1 | 12/2005 | Mangano | |
| 7,241,252 B1 | 7/2007 | Gagliardi | |
| 7,255,666 B2 | 8/2007 | Cardenas | |
| 7,828,703 B1 | 11/2010 | Boesch | |
| 7,837,600 B1 | 11/2010 | Habing | |
| 8,029,426 B2 | 10/2011 | Sohn | |
| 8,220,087 B2 | 7/2012 | Villa et al. | |
| 8,631,833 B2 | 1/2014 | Garbarino | |
| 8,916,251 B2 | 12/2014 | Tvelil | |
| 9,398,832 B2 | 7/2016 | Sohn | |
| 9,439,492 B2 | 9/2016 | Johnson | |
| 9,737,744 B2 * | 8/2017 | Austin | A63B 21/0023 |
| 2005/0271857 A1 * | 12/2005 | Brody | A63B 21/0004 |
| | | | 428/78 |
| 2007/0066467 A1 * | 3/2007 | Edwards | A63B 21/4037 |
| | | | 482/148 |
| 2008/0120774 A1 * | 5/2008 | Hite | A41B 13/06 |
| | | | 5/494 |
| 2009/0098348 A1 * | 4/2009 | Barker | A47K 10/02 |
| | | | 428/195.1 |
| 2009/0144874 A1 * | 6/2009 | Stein | A41D 15/04 |
| | | | 2/69 |
| 2009/0144924 A1 * | 6/2009 | Stein | A41D 1/00 |
| | | | 15/210.1 |
| 2011/0072581 A1 * | 3/2011 | Villa | A63B 21/4037 |
| | | | 5/420 |
| 2011/0143083 A1 | 6/2011 | Scorgie | |
| 2011/0305867 A1 * | 12/2011 | Lee | B32B 5/26 |
| | | | 428/102 |
| 2012/0124739 A1 * | 5/2012 | Crowne | A47G 9/062 |
| | | | 5/417 |
| 2012/0151649 A1 | 6/2012 | Peterson | |
| 2012/0210517 A1 * | 8/2012 | Patel | A47G 9/062 |
| | | | 8/137 |
| 2012/0255643 A1 | 10/2012 | Duan | |
| 2013/0125307 A1 * | 5/2013 | Margalit | A47G 9/062 |
| | | | 5/417 |
| 2013/0156980 A1 * | 6/2013 | Bonanno | A47K 10/02 |
| | | | 428/34.9 |
| 2013/0276230 A1 * | 10/2013 | Kress | A47G 9/062 |
| | | | 5/419 |
| 2014/0068858 A1 | 3/2014 | Wambeke | |
| 2014/0215687 A1 | 8/2014 | Andrews | |
| 2015/0238055 A1 * | 8/2015 | Manno | A47K 10/02 |
| | | | 34/95.2 |
| 2015/0238803 A1 * | 8/2015 | Neal | A43B 17/00 |
| | | | 5/417 |
| 2015/0272400 A1 * | 10/2015 | Lan | A47K 10/02 |
| | | | 15/209.1 |
| 2016/0270605 A1 | 9/2016 | Jones-Felton | |
| 2017/0252597 A1 * | 9/2017 | Klein | A63B 21/0555 |

OTHER PUBLICATIONS

Product Screen on YogaOutlet.com Site, for the Gaiam Thirty Yoga Hand Towel, circa Jan. 2017, 1 Page.
Product Screen on YogaRat Site, for the 32"×68" Beach and Pool Towel, circa Jan. 2017, 1 Page.

* cited by examiner

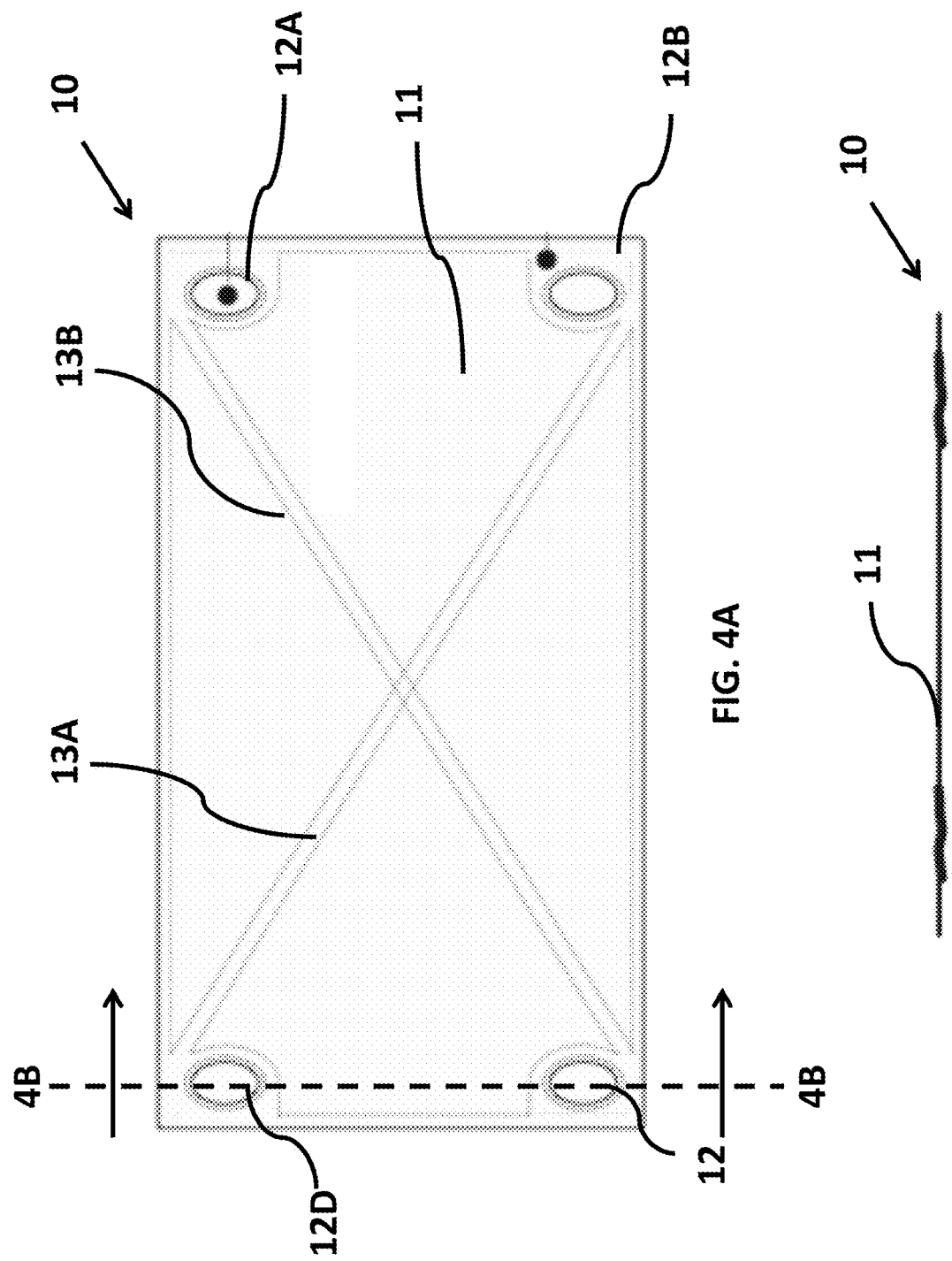

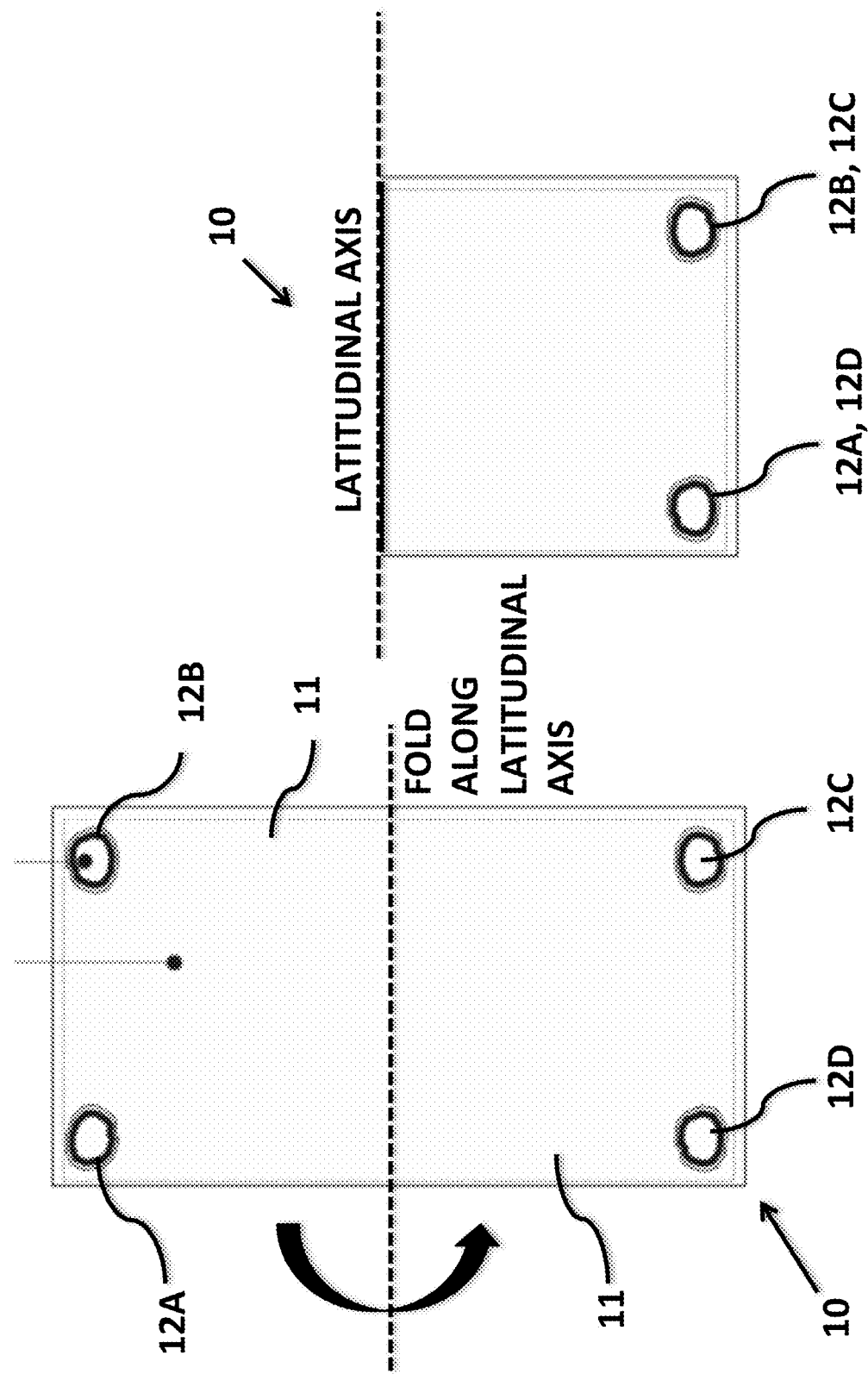

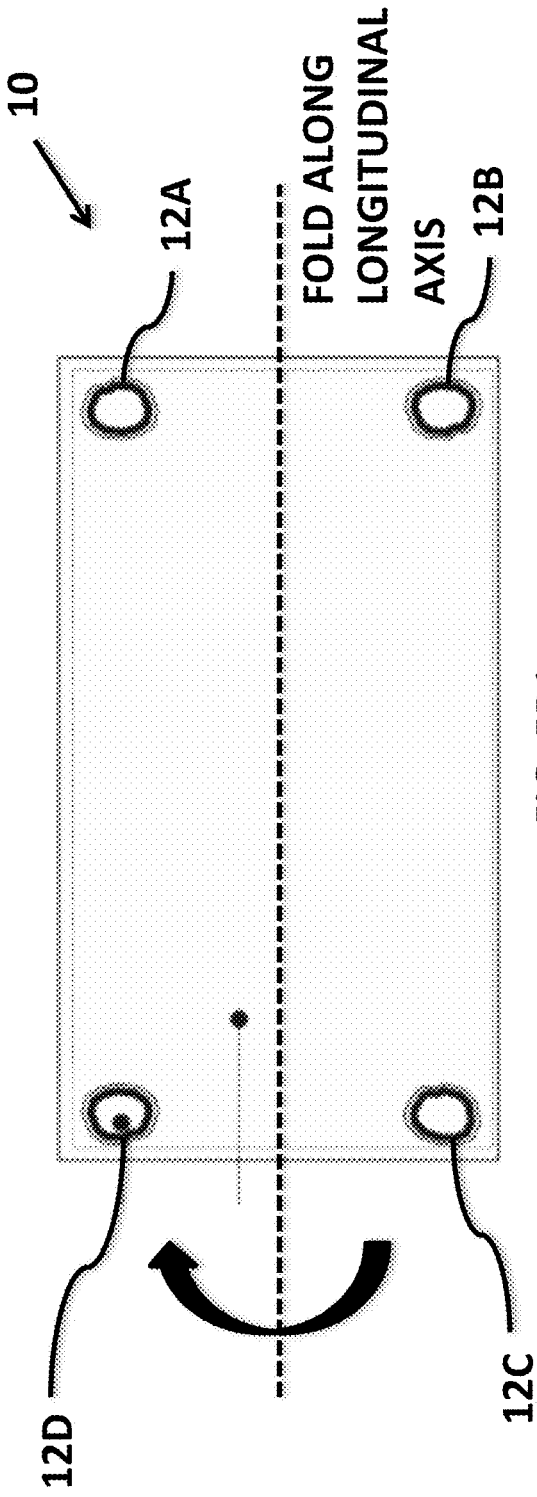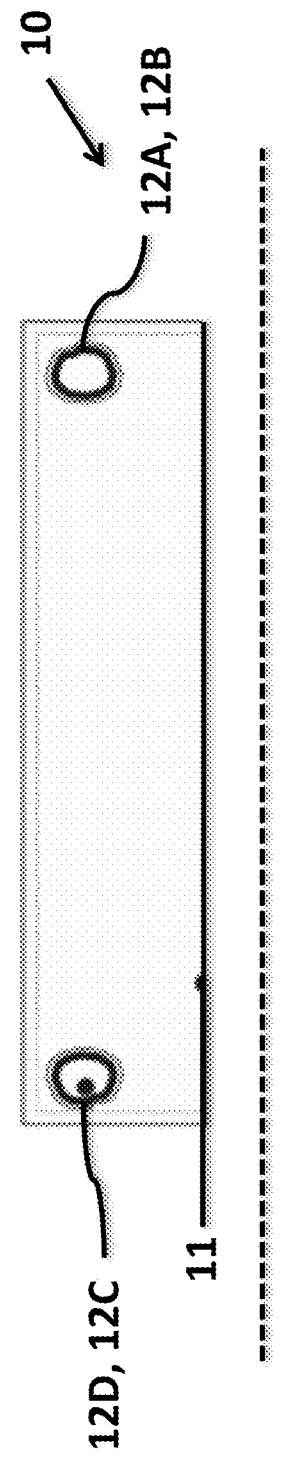
FIG. 5B1
FIG. 5B2

METHOD OF MANUFACTURING ISOMETRIC-EXERCISE TOWEL OF THE PRESENT INVENTION

A: Positioning a piece of moisture-absorbent fabric material on a flat surface and using a CNC-based fabric cutting machine table to cut the fabric so that it meets its dimensions, and has necessary the hand/foot-insertable apertures

B: Using a CNC-based sewing machine table to apply stitches to the fabric material to reinforce each hand/foot-insertable aperture, form necessary reinforcements between the hand/foot-passable apertures

C: Applying finishing operations to the fabric material using a CNC-based inspection and finishing machine table to produce the isometric-exercise towel of the first embodiment of the present invention

FIG. 6

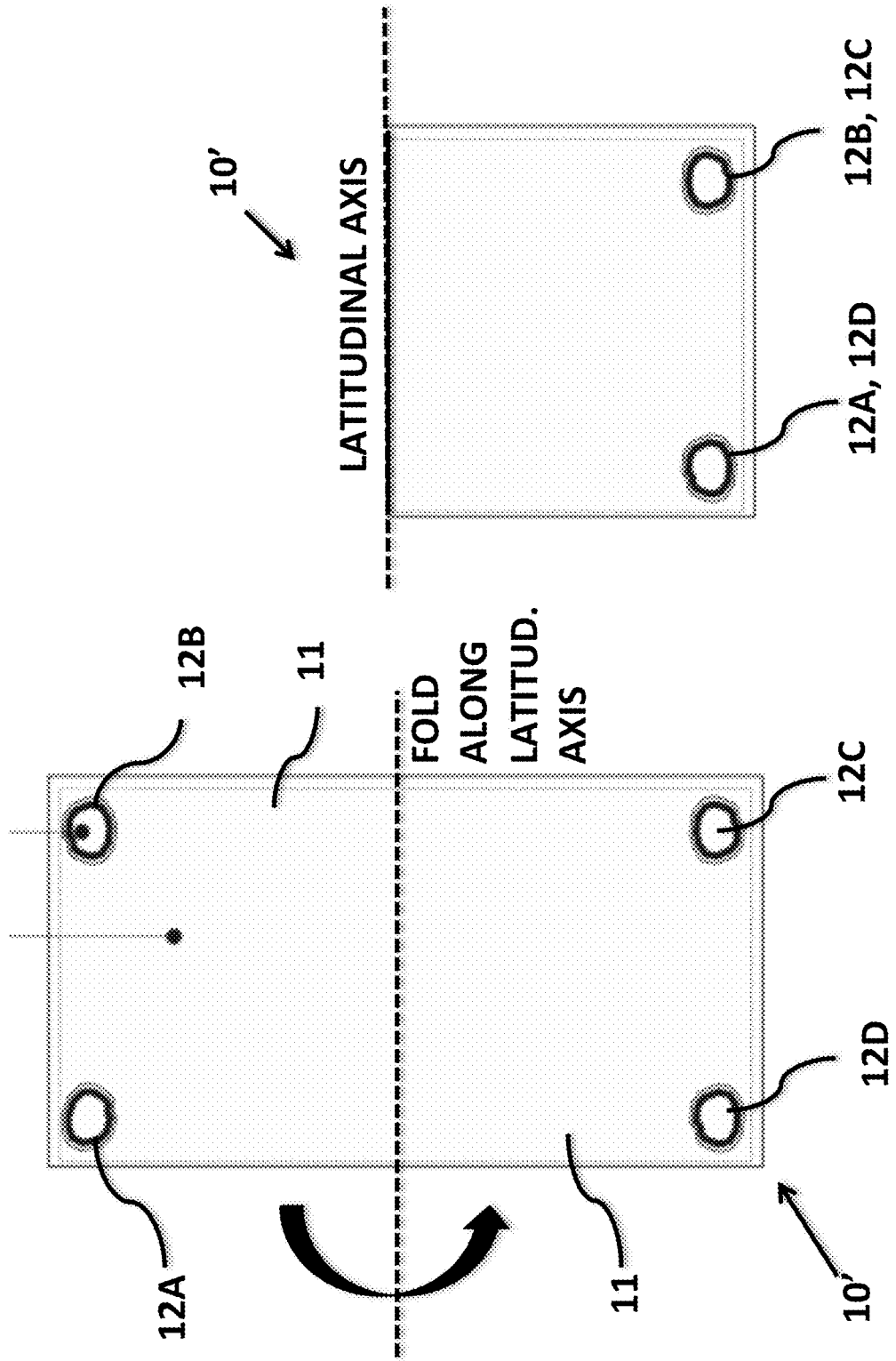

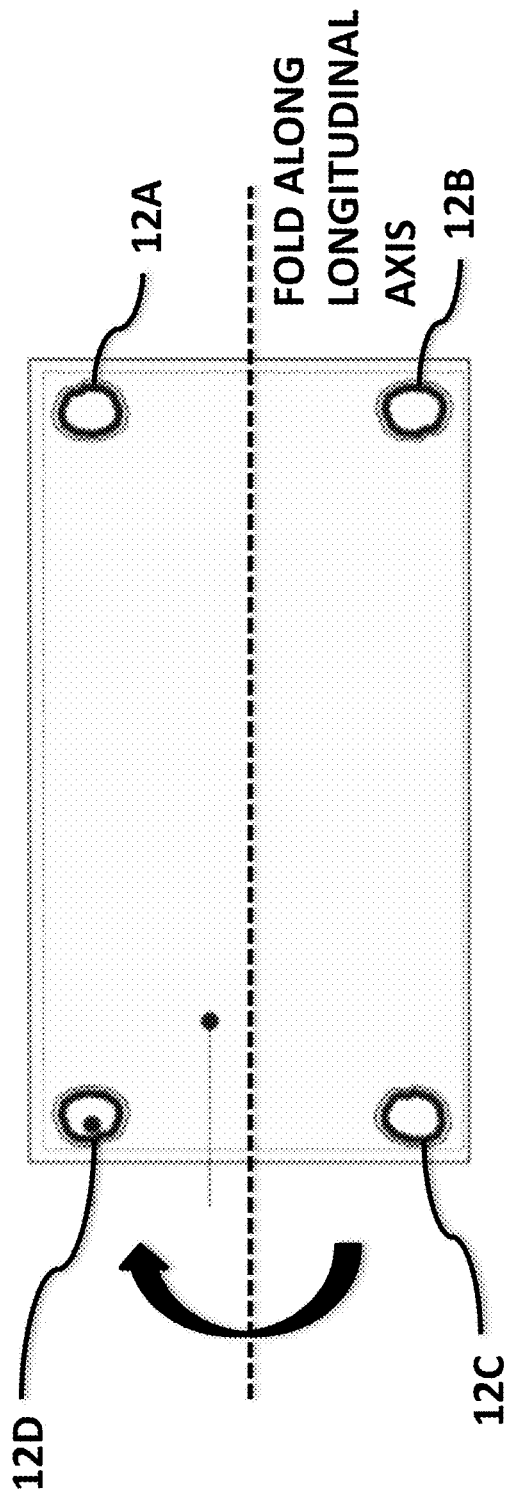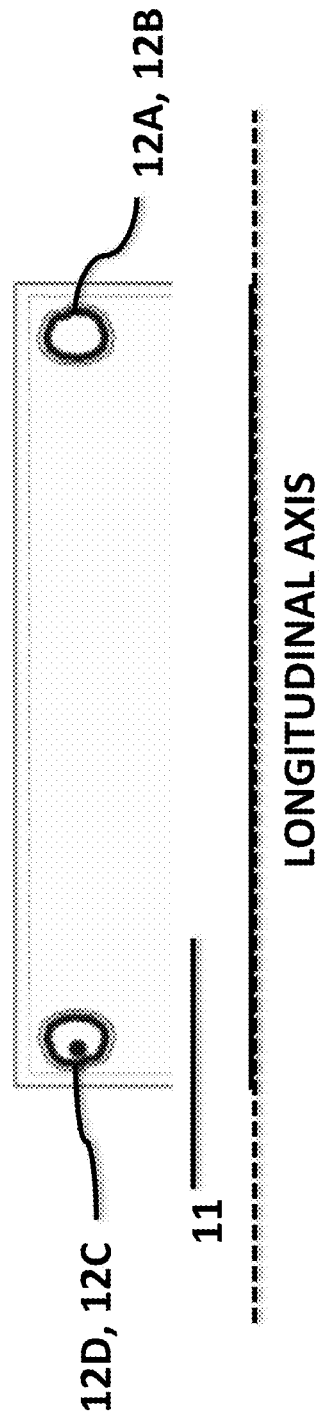
FIG. 8B1
FIG. 8B2

METHOD OF MANUFACTURING ISOMETRIC-EXERCISE TOWEL OF THE PRESENT INVENTION

A: Positioning a piece of moisture-absorbent fabric material on a flat surface and using a CNC-based fabric cutting machine table to cut it so that it meets its dimensions, and has necessary The hand/foot-insertable apertures; and also positioning a piece of canvas material on the table to be cut into two pieces with hand/foot-insertable apertures, for each isometric-exercise towel to be manufactured

B: Using A CNC-based sewing machine table to stitch to the fabric material and canvass pieces together to reinforce each hand/foot-passable aperture, and also form necessary reinforcements between the hand/foot-insertable apertures

C: Applying finishing operations to the fabric material using a CNC-based inspection and finishing machine table to produce the isometric-exercise towel of the second illustrative embodiment of the present invention

FIG. 9

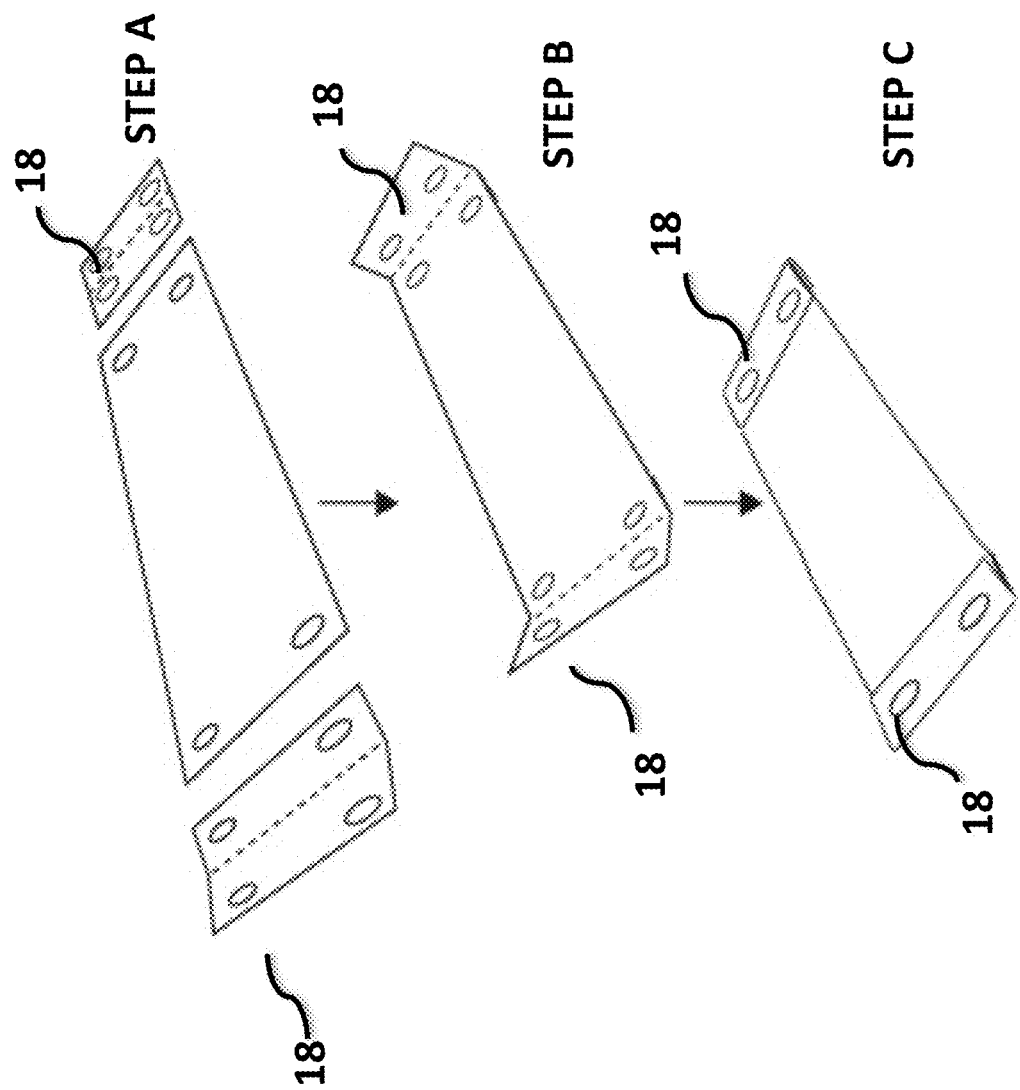

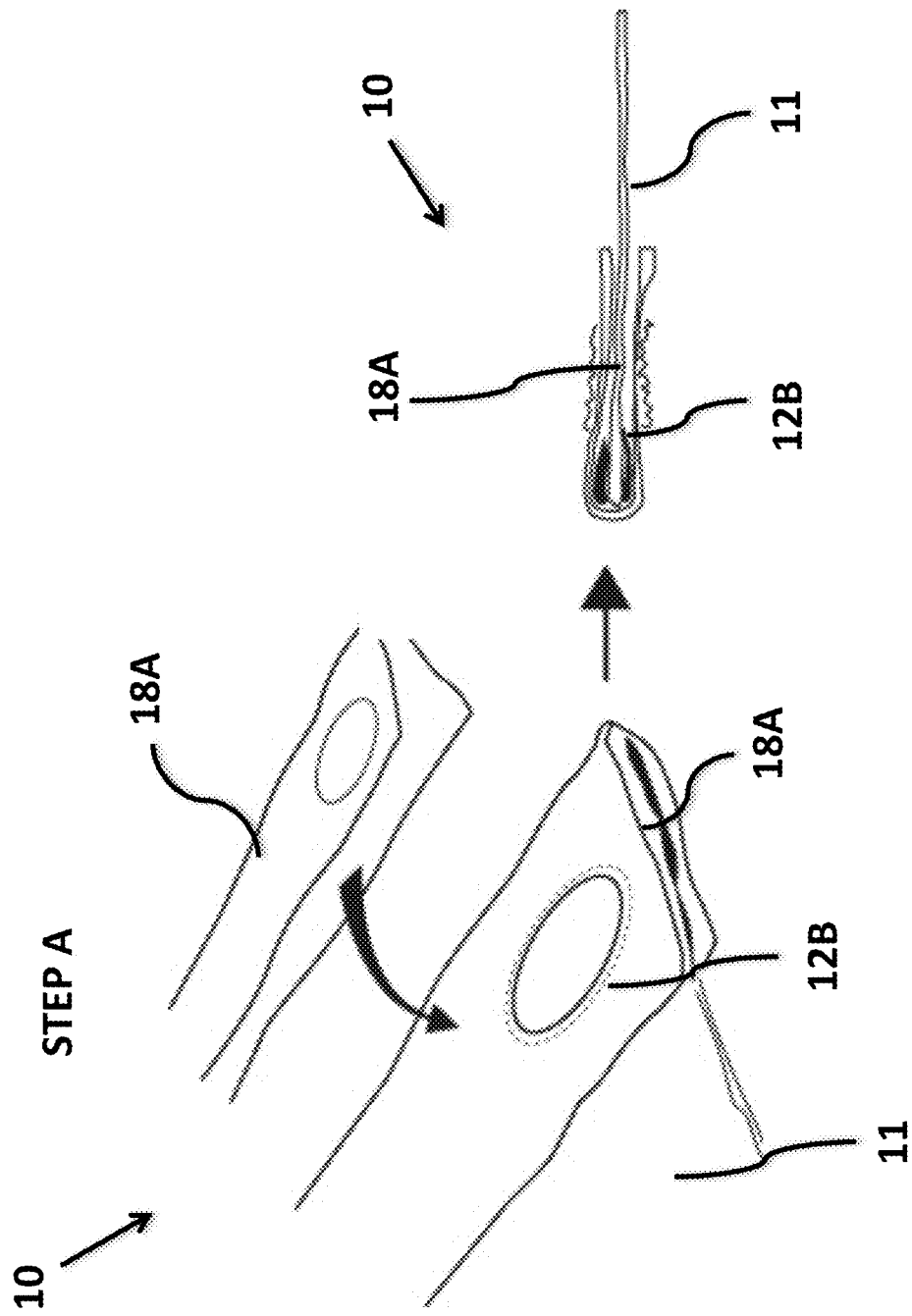

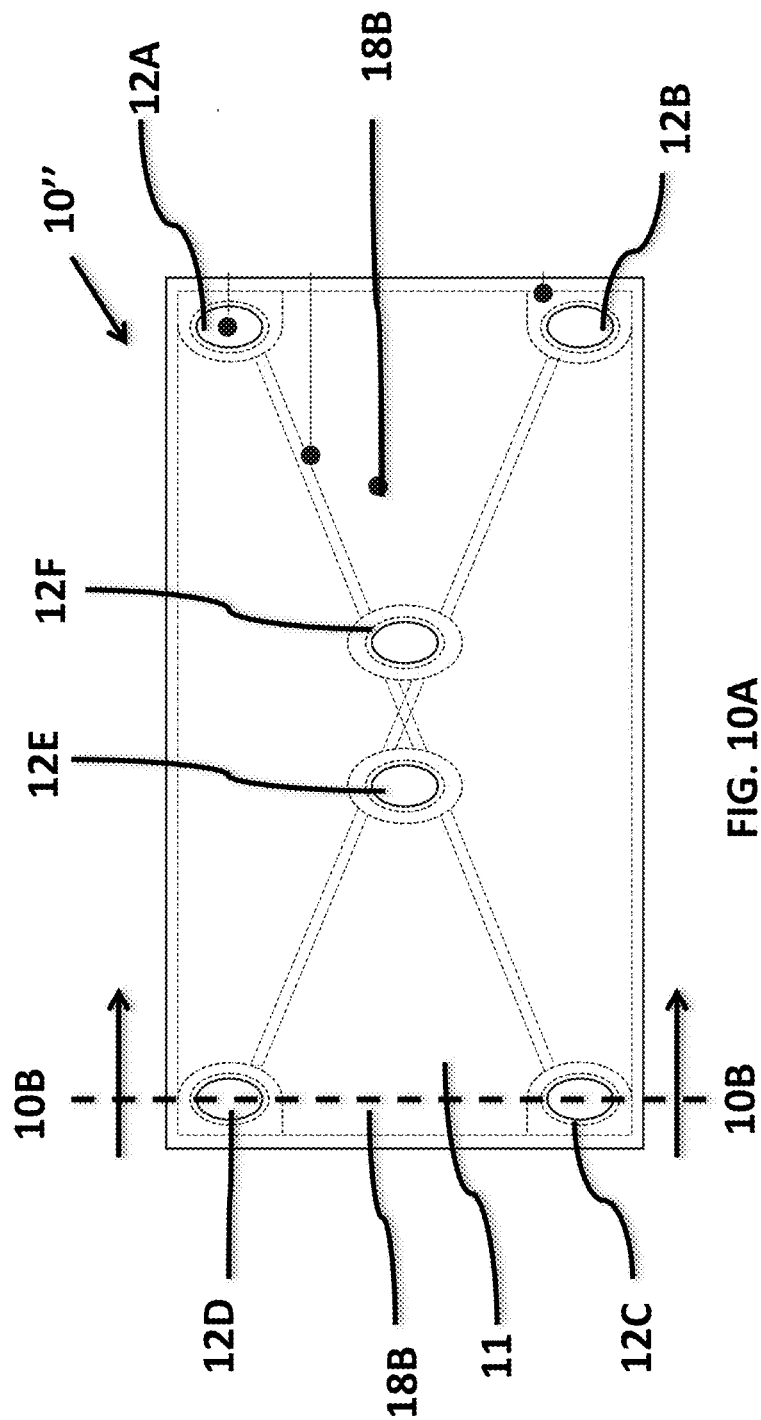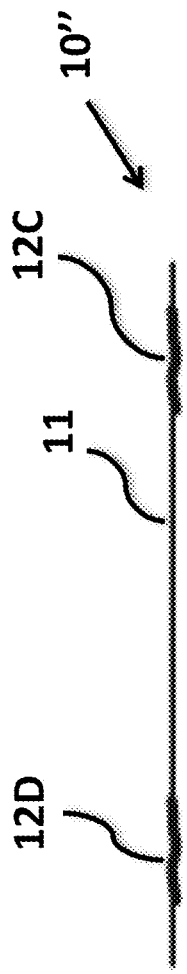
FIG. 10A
FIG. 10B

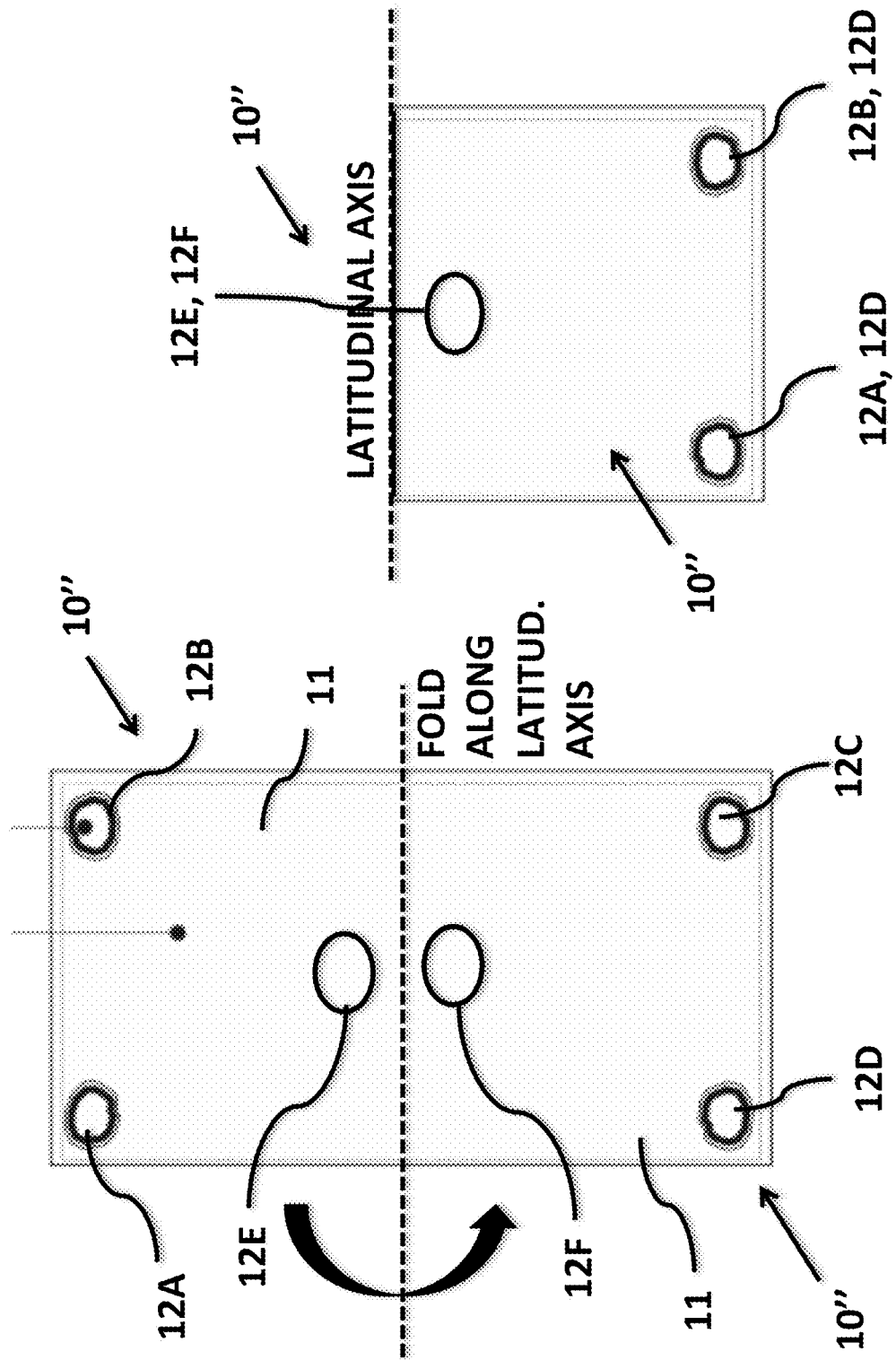

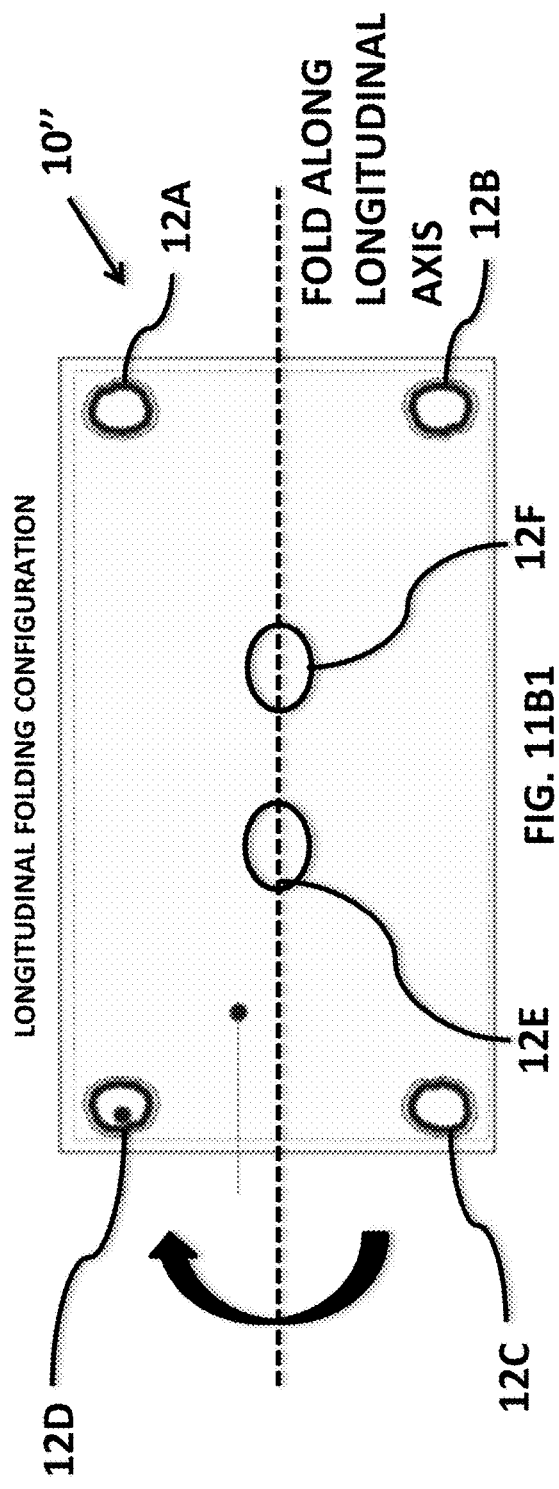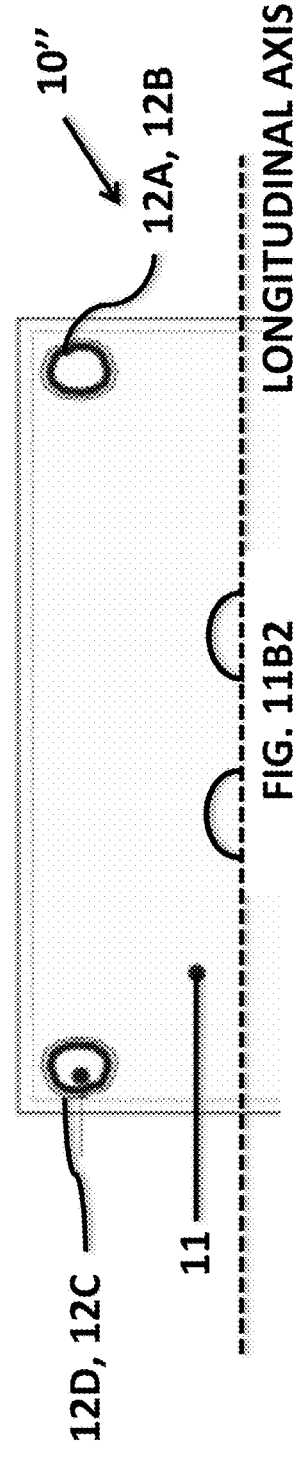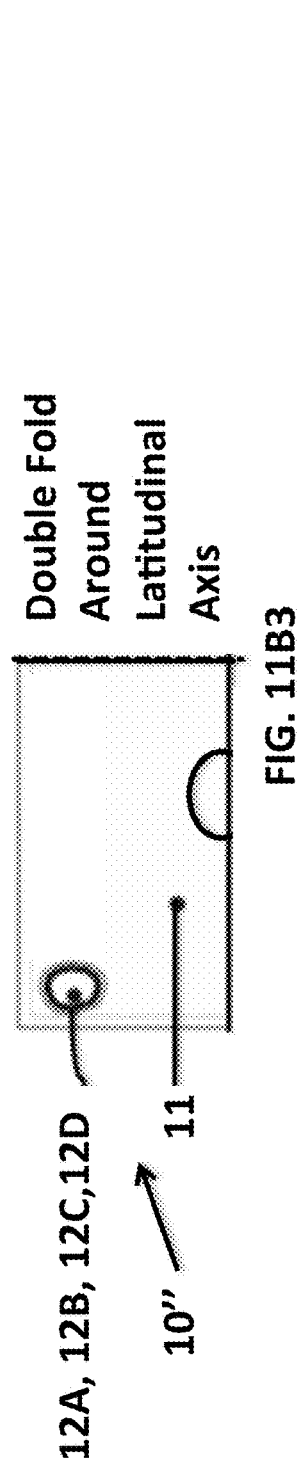
FIG. 11B1  FIG. 11B2  FIG. 11B3

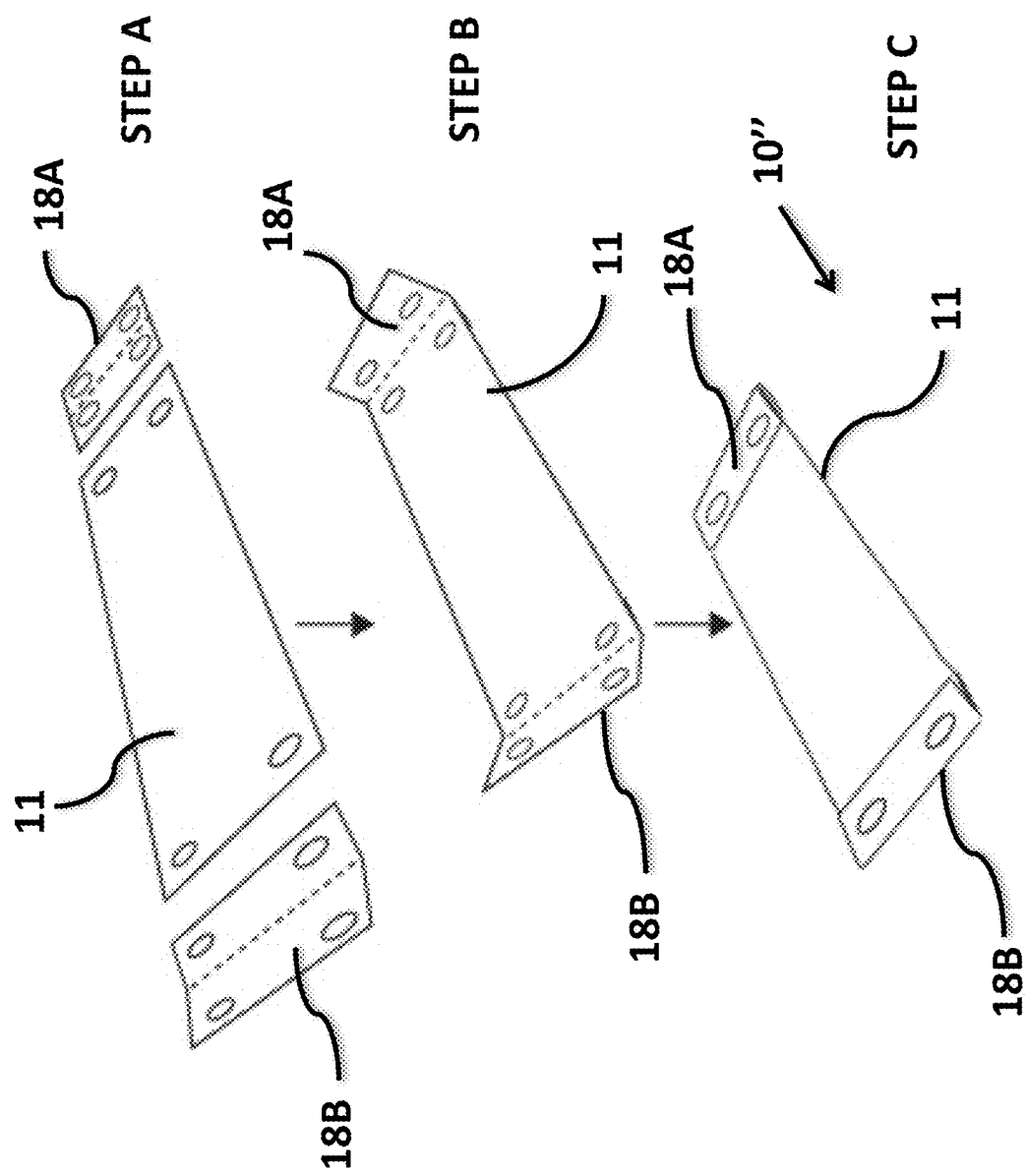
FIG. 12B1

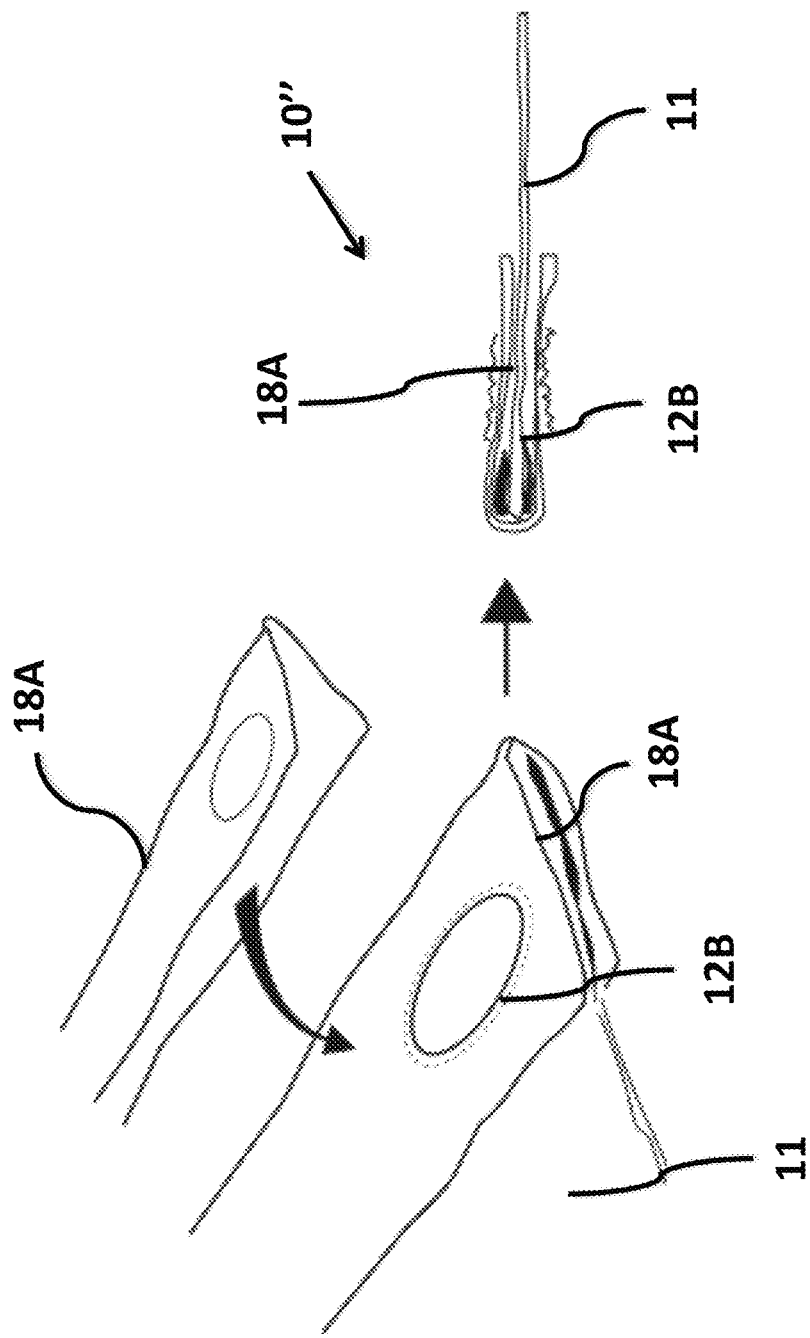

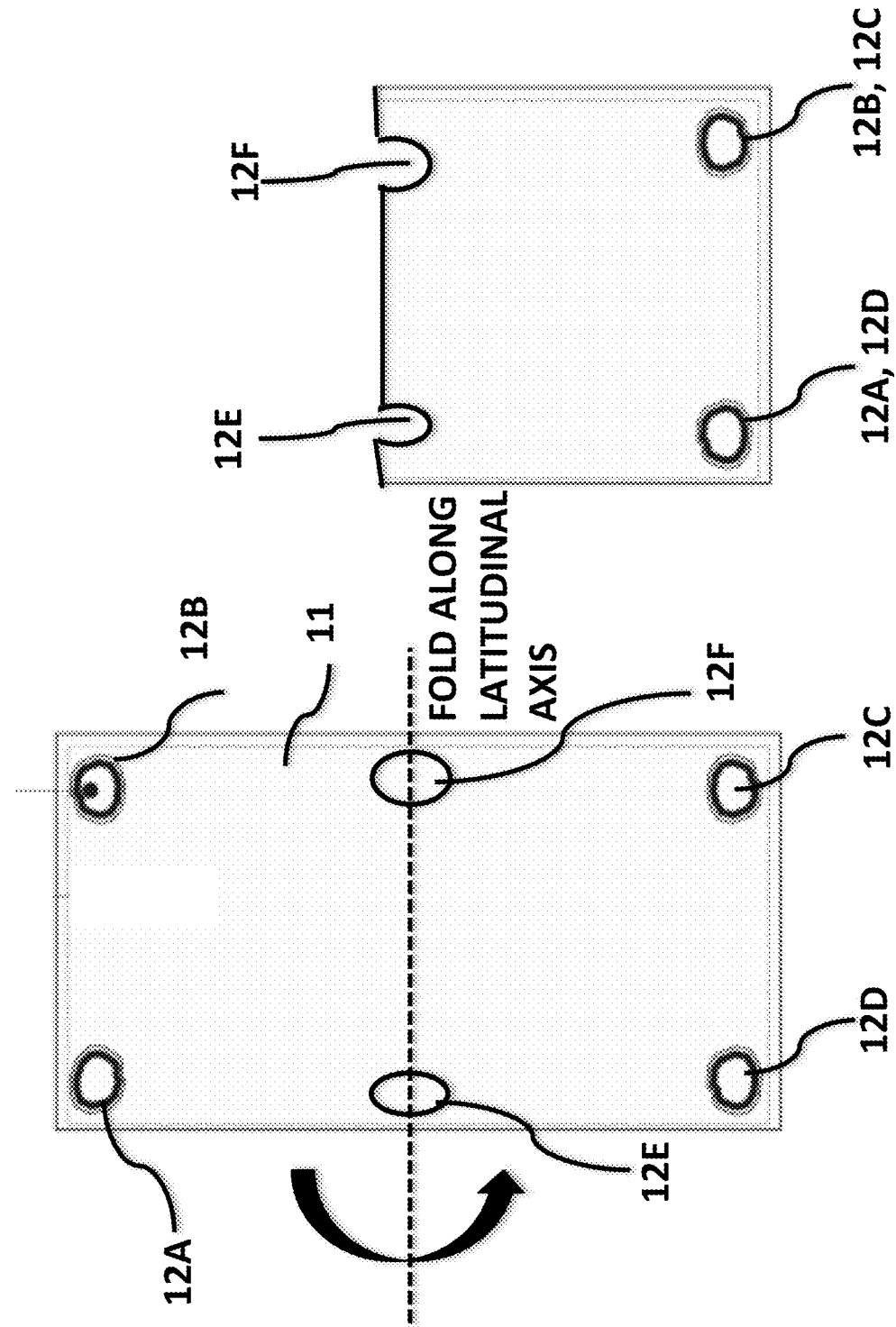

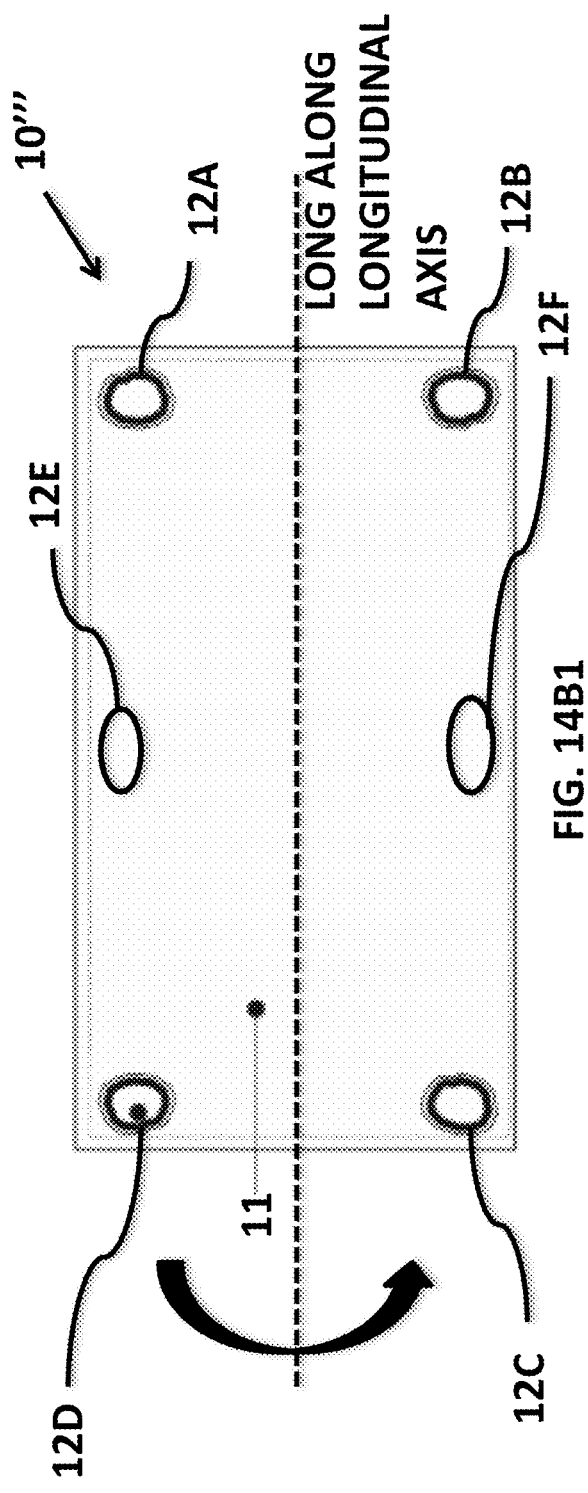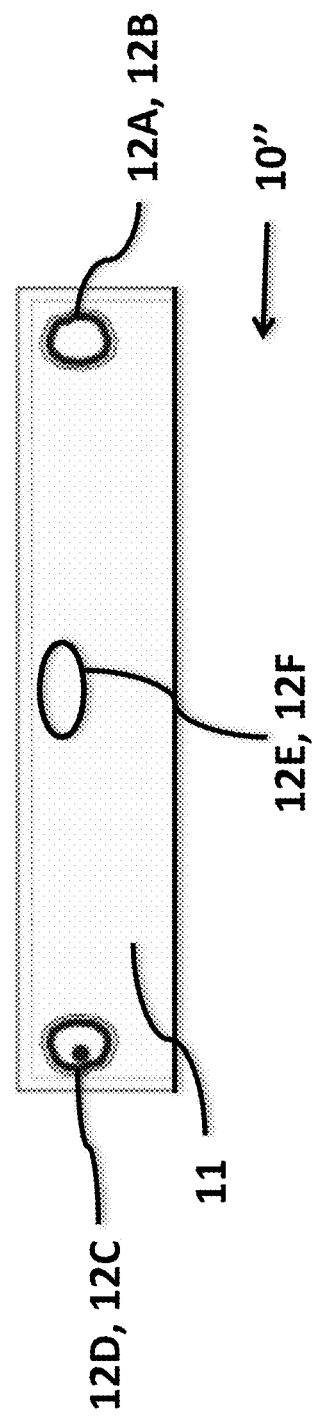
FIG. 14B1
FIG. 14B2

METHOD OF MANUFACTURING ISOMETRIC-EXERCISE TOWEL OF THE PRESENT INVENTION

A: Positioning a piece of moisture-absorbent fabric material on a flat surface and using a CNC-based fabric cutting machine table to cut it so that it meets its dimensions, and has necessary the hand/foot-insertable apertures; and also positioning a piece of canvas material on the table to be cut into two pieces with hand/foot-insertable apertures, for each isometric-exercise towel to be manufactured

→

B: Using A CNC-based sewing machine table to apply stitches to the fabric material to reinforce each hand/foot-insertable aperture, form necessary reinforcements between the hand/foot-insertable apertures

→

C: Applying finishing operations to the fabric Material using a CNC-based inspection and finishing machine table to produce the isometric-exercise towel of the first embodiment of the present invention

FIG. 15

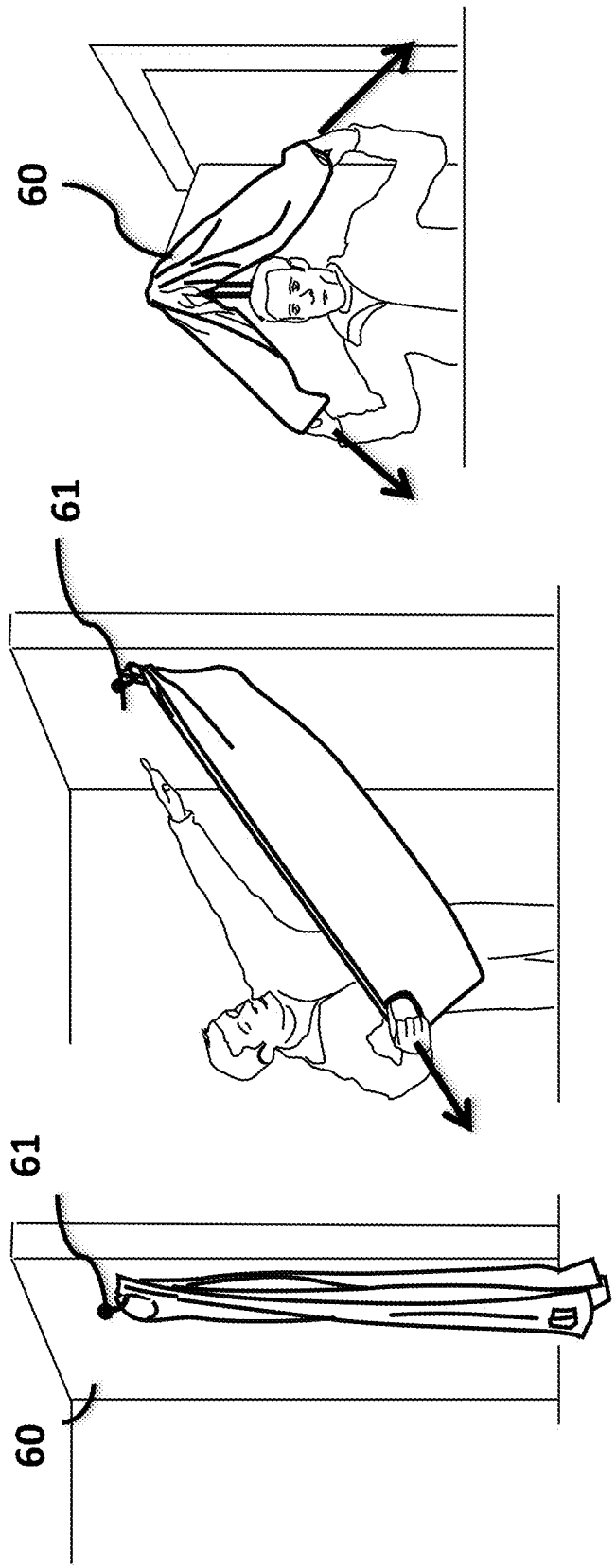

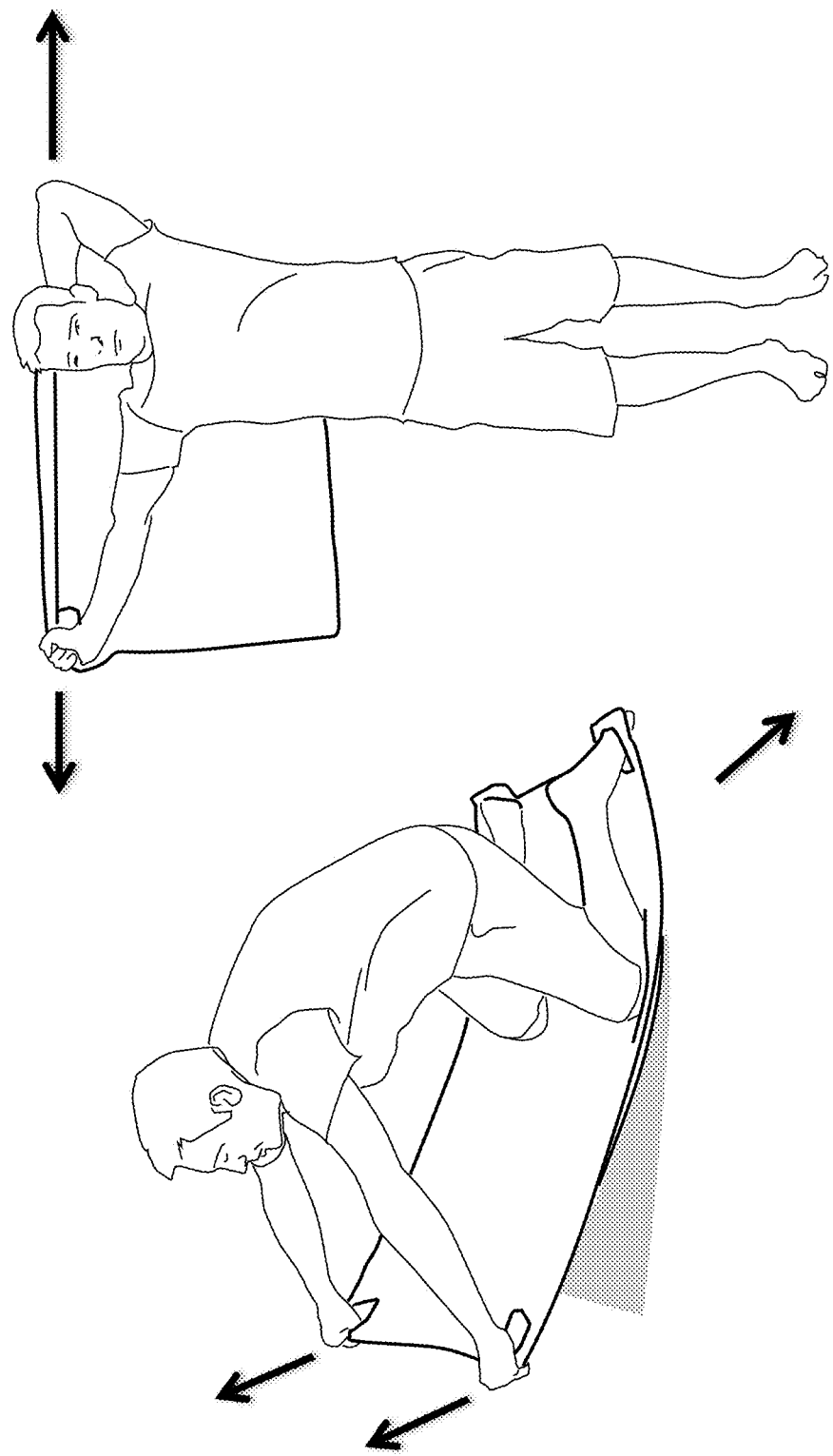

ISOMETRIC-EXERCISE TOWEL AND METHODS OF ISOMETRIC EXERCISE

BACKGROUND OF INVENTION

Field of Invention

The present invention relates to new and improved methods of and apparatus for performing isometric exercises in diverse environment.

Brief Description of the State of Knowledge in the Art

It is well known that physical exercise enhances and maintains an individual's physical fitness and overall health and wellness. Physical exercise is performed for various reasons, including increasing growth and development, preventing aging, strengthening muscles and the cardiovascular system, honing athletic skills, weight loss or maintenance, and merely enjoyment. Frequent and regular physical exercise boosts the immune system and helps prevent cardiovascular disease, type 2 diabetes, and obesity. It may also help prevent stress and depression, increase quality of sleep and act as a non-pharmaceutical sleep aid to treat diseases such as insomnia. Physical exercise also helps promote or maintain positive self-esteem, improve mental health, maintain steady digestion and treat constipation and gas, regulate fertility health, and augment an individual's sex appeal or body image.

Exercises are generally grouped into three types depending on the overall effect they have on the human body.

Aerobic exercises, such as cycling, walking, running, hiking, and playing tennis, focus on increasing cardiovascular endurance.

Anaerobic exercises, such as weight training, increase short-term muscle strength; and Flexibility exercises such as stretching improve the range of motion of muscles and joints.

Isometric exercise, or Isometrics, ("iso" means equal, or the same, and "metric" refers to length) involves tensing muscles either against other muscles or immovable objects, while the length of the muscle remains the same. Isometrics can be a useful part of an exercise program to help reverse age-related muscle loss. Research has shown that one can sometimes obtain gains in both muscle size and muscle strength using isometric exercises.

Research has shown that because of the reduced blood flow during prolonged muscle tension, numerous growth factors remain in the muscle tissue longer and actually stimulate muscle growth. Doing a higher number of contractions increases strength, while holding contractions longer increases muscle mass.

Currently, most isometric exercises involve a person pushing his or her hands, arms and/or feet against other parts of one's body, or stationary objects, to tension ones muscles against other muscles or immovable objects.

FIGS. 1A through 1F illustrate six very common prior art isometric exercises performed by a person without the use of special-isometric apparatus.

FIG. 2, on the other hand, shows the prior art Steel Bow® Bullworker™ isometric apparatus which is used by many to perform isometric exercises around the world.

FIG. 3 shows the prior art Grip™ isometric apparatus also used by many to perform isometric exercise, with the benefit of displaying a measure of tension that can be helpful to some during a their isometric exercise programs.

While there have been some advances in the art of isometric exercise, clearly there is a great need in the art for new and improved ways of performing isometric exercises, in a more convenient and useful manner, while avoiding the shortcomings and drawbacks of prior art devices and methodologies.

OBJECTS AND SUMMARY OF THE PRESENT INVENTION

It is therefore a primary object of the present invention to provide a new and improved apparatus and methods of isometric exercise in diverse end-user environments, while avoiding the shortcomings and drawbacks of prior art devices and methodologies.

Another object of the present invention is to provide a new and improved isometric-exercise towel constructed from a layer of moisture-absorbent material (i) having a thick woven pile offering excellent moisture-wicking characteristics, (ii) four hand/foot-insertable apertures formed in the corners of the isometric-exercise towel, reinforced with double stitching about the perimeter of each hand/foot-insertable aperture, and (iii) a reinforced stitching pattern between pairs of hand/foot-insertable apertures formed on opposing ends of the isometric-exercise towel.

Another object of the present invention is to provide a new and improved isometric-exercise towel having reinforced stitching made about hand/foot-insertable apertures formed in the corners of the isometric-exercise towel.

Another object of the present invention is to provide a new and improved isometric-exercise towel having multiple stitches passing through and reinforcing the layer of moisture-absorbent material, along lines between the hand-foot-insertable apertures, where the stitching is made.

Another object of the present invention is to provide a new and improved isometric-exercise towel which can be folded along its latitudinal axis so that the apertures on the latitudinal ends are spatially aligned for insertion of the user's hands or feet.

Another object of the present invention is to provide a new and improved isometric-exercise towel which can be folded along its longitudinal axis, so that the apertures on the longitudinal sides are spatially aligned for insertion of the user's hands or feet.

Another object of the present invention is to provide a new and improved process for manufacturing an isometric-exercise towel comprising the steps of (a) positioning a piece of moisture-absorbent fabric material on a flat surface and using a CNC-based fabric cutting machine table to cut it so that it meets its dimensions, and has necessary the hand/foot-insertable apertures, (b) using a CNC-based sewing machine table to apply stitches to the fabric material to reinforce each hand/foot-insertable aperture, form necessary reinforcements between the hand/foot-insertable apertures, and (c) applying finishing operations to the fabric material using a CNC-based inspection and finishing machine table to produce the isometric-exercise towel.

Another object of the present invention is to provide a new and improved isometric-exercise towel constructed from (i) a layer of moisture absorbent material (e.g. Terricloth) having a thick woven pile offering excellent moisture-wicking characteristics, and two pieces of pliant canvass material for reinforcing the ends of the layer of moisture-absorbent material in which the four hand/foot-insertable apertures are formed in the corners of the isometric-exercise towel, and reinforced with double stitching about the perimeter of each hand/foot-insertable aperture, and between pairs of hand/foot-insertable apertures formed on opposing ends of the isometric-exercise towel.

Another object of the present invention is to provide a new and improved isometric-exercise towel of having reinforced stitching made about hand/foot-insertable apertures formed in the corners of the isometric-exercise towel.

Another object of the present invention is to provide a new and improved isometric-exercise towel having multiple stitches passing through and reinforcing the layer of moisture-absorbent material, along lines between the hand-foot-insertable apertures, where the stitching is made.

Another object of the present invention is to provide a new and improved isometric-exercise towel which can be folded along its latitudinal axis so that the apertures on the latitudinal ends are spatially aligned for insertion of the user's hands or feet.

Another object of the present invention is to provide a new and improved isometric-exercise towel which can be folded along its longitudinal axis, so that the apertures on the longitudinal sides are spatially aligned for insertion of the user's hands or feet.

Another object of the present invention is to provide a new and improved process for manufacturing an isometric-exercise towel comprising the steps of (a) positioning a piece of moisture-absorbent fabric material on a flat surface and using a CNC-based fabric cutting machine table to cut it so that it meets its dimensions, and has necessary the hand/foot-insertable apertures, and also positioning a piece of canvas material on the table to be cut into two pieces with hand/foot-insertable apertures, for each isometric-exercise towel to be manufactured, (b) using a CNC-based sewing machine table to apply stitches to the fabric material to reinforce each hand/foot-insertable aperture, form necessary reinforcements between the hand/foot-insertable apertures, and (c) applying finishing operations to the fabric material using a CNC-based inspection and finishing machine table to produce the isometric-exercise towel.

Another object of the present invention is to provide a new and improved video-based isometric exercise communication and presentation network allowing individual users remotely situated to use wireless mobile computing devices such as an Apple® iPad device or Android® tablet device to display videos showing isometric exercise routines and programs using the isometric-exercise towel of the present invention.

Another object of the present invention is to provide a first new and improved method of isometric exercise workout using an isometric-exercise towel attached to a door hook.

Another object of the present invention is to provide a second new and improved method of isometric exercise using an isometric-exercise towel attached to the top surface of a door to perform an isometric exercise using the isometric-exercise towel.

Another object of the present invention is to provide a third new and improved method of isometric exercise, involving a person inserting his/her two feet within the lower pair of hand/foot-insertable apertures in an isometric-exercise towel, and his two hands inserted within the upper hand/foot-insertable apertures thereof, so as to perform an isometric exercise using the same by stretching the isometric-exercise towel in outward directions in an isometric manner.

Another object of the present invention is to provide a fourth new and improved method of isometric exercise, involving a person inserting one foot within the lower pair of folded hand/foot-insertable apertures in the isometric-exercise towel, arranged in a longitudinally folded configuration, while his left hand is inserted within the upper folded pair of hand/foot-insertable apertures thereof, so as to perform an isometric exercise using the same by stretching the isometric-exercise towel in outward directions in an isometric manner.

Another object of the present invention is to provide a fifth new and improved method of isometric exercise involving a person inserting one foot within the lower pair of folded hand/foot-insertable apertures in the isometric-exercise towel, arranged in a folded configuration, while both his left and right hands are inserted within the upper folded pair of hand/foot-insertable apertures thereof, so as to perform an isometric exercise using the same by stretching the isometric-exercise towel in outward directions in an isometric manner.

Another object of the present invention is to provide a sixth new and improved method of isometric exercise involving a person inserting one his left hand within one hand/foot-insertable aperture in the isometric-exercise towel, while his right hand is inserted within the opposing hand/foot-insertable aperture and the towel is draped behind his shoulders, so as to perform an isometric exercise using the same by stretching the isometric-exercise towel in outward directions in an isometric manner.

Another object of the present invention is to provide a seventh new and improved method of isometric exercise involving a person inserting one his left hand within one hand/foot-insertable aperture in the isometric-exercise towel, while his right hand is inserted within the opposing hand/foot-insertable aperture and the towel is draped behind his shoulders, so as to perform an isometric exercise using the same by stretching the isometric-exercise towel in outward directions in an isometric manner.

Another object of the present invention is to provide an eighth new and improved method of isometric exercise involving a person sitting down with his legs crossed and upon one longitudinal end of the isometric-exercise towel, while his left and right hands are inserted within the pair of opposing hand/foot-insertable apertures on the opposing ends of the isometric-exercise towel, so as to perform an isometric exercise using the same by lifting the opposing end of the isometric-exercise towel and stretching the isometric-exercise towel in outward directions in an isometric manner.

Another object of the present invention is to provide a ninth new and improved method of isometric exercise involving a person sitting down with his legs cross and sitting in the middle of the isometric-exercise towel, while the person's pair of left and right hands are inserted within the pair of hand/foot-insertable apertures on one longitudinal end of the isometric-exercise towel pulled up from behind the back of the person, so as to perform an isometric exercise using the same by stretching the isometric-exercise towel in outward directions in an isometric manner.

Another object of the present invention is to provide a tenth new and improved method of isometric exercise involving a person inserting his left hand within one hand/foot-insertable aperture in the isometric-exercise towel in its latitudinally-folded configuration, while his right hand is inserted within the other hand/foot-insertable aperture on the same side of the towel, so as to perform an isometric exercise using the same by stretching the isometric-exercise towel in outward directions in an isometric manner.

Another object of the present invention is to provide an eleventh new and improved method of isometric exercise involving a person inserting right hand within the first pair of folded hand/foot-insertable apertures in the isometric-exercise towel, arranged in a latitudinally-folded configuration, while his left foot is inserted within the lower folded pair of hand/foot-insertable apertures thereof, so as to perform an isometric exercise using the same by stretching the isometric-exercise towel in outward directions in an isometric manner.

Another object of the present invention is to provide a twelfth new and improved method of isometric exercise involving a person inserting left hand within the first pair of folded hand/foot-insertable apertures in the isometric-exercise towel, arranged in a latitudinally folded configuration, while right left hand is inserted within the upper folded pair of hand/foot-insertable apertures thereof, so as to perform an isometric exercise using the same by stretching the isometric-exercise towel in outward directions in an isometric manner.

Another object of the present invention is to provide a thirteenth new and improved method of isometric exercise involving a person inserting left hand within the first pair of folded hand/foot-insertable apertures in the isometric-exercise towel, arranged in a longitudinally folded configuration, while his right hand is inserted within the upper folded pair of hand/foot-insertable apertures thereof, as the isometric-exercise towel is wrapped around the person's rear waist region, so as to perform an isometric exercise using the same by stretching the isometric-exercise towel in outward directions in an isometric manner.

Another object of the present invention is to provide a fourteenth new and improved method of isometric exercise involving a person inserting one hand within the first pair of hand/foot-insertable apertures in the isometric-exercise towel, while his left hand is inserted within the upper folded pair of hand/foot-insertable apertures thereof, as the towel is wrapped behind the person's rear waist region, so as to perform an isometric exercise using the same by stretching the isometric-exercise towel in outward directions in an isometric manner.

Another object of the present invention is to provide a fifteenth new and improved method of isometric exercise involving a person inserting both hands within the first pair of folded hand/foot-insertable apertures in the isometric-exercise towel, while kneeling on the middle region of the isometric-exercise towel, as the person's feet are inserted within the opposing pair of hand/foot-insertable apertures thereof, so as to perform an isometric exercise using the same by stretching the isometric-exercise towel in outward directions in an isometric manner.

Another object of the present invention is to provide a sixteenth new and improved method of isometric exercise involving a person inserting his right hand within the hand/foot-insertable aperture in one end of the isometric-exercise towel, while his left hand is inserted within the opposing hand/foot-insertable aperture, while the isometric-exercise towel is suspended behind the person's head, so as to perform an isometric exercise using the same by stretching the isometric-exercise towel in outward directions in an isometric manner.

These and other objects of invention will become apparent hereinafter and in the Claims to Invention appended hereto.

BRIEF DESCRIPTION OF THE DRAWINGS

In order to more fully understand the objects of the present invention, the following detailed description of the illustrative embodiments should be read in conjunction with the accompanying figure Drawings in which:

FIG. 4A is a plan view of the first illustrative embodiment of the isometric-exercise towel of the present invention constructed from a layer of moisture-absorbent material so as to have (i) a thick woven pile offering excellent moisture-wicking characteristics, (ii) four hand/foot-insertable apertures formed in the corners of the isometric-exercise towel, reinforced with double stitching about the perimeter of each hand/foot-insertable aperture, and (iii) a reinforced stitching pattern between pairs of hand/foot-insertable apertures formed on opposing ends of the isometric-exercise towel;

FIG. 4B is a cross-sectional view of the first illustrative embodiment of the isometric-exercise towel of the present invention, taken about line 4B-4B in FIG. 4A showing the reinforced stitching made about the hand/foot-insertable apertures form on the end side of the isometric-exercise towel;

FIGS. 5A1 and 5A2 set forth schematic illustrations showing how the isometric-exercise towel of the first illustrative embodiment of the present invention, depicted in FIGS. 4A and 4B, is folded along its latitudinal axis so that the apertures on the latitudinal ends are spatially aligned for insertion of the user's hands or feet, as described hereinafter;

FIGS. 5B1 and 5B2 set forth schematic illustrations showing how the isometric-exercise towel of the first illustrative embodiment of the present invention, depicted in FIGS. 4A and 4B, is folded along its longitudinal axis, so that the apertures on the longitudinal sides are spatially aligned for insertion of the user's hands or feet, as described hereinafter;

FIG. 6 is a flow chart describing the primary steps involved in manufacturing the isometric-exercise towel of the first illustrative embodiment of the present invention, comprising (a) positioning a piece of moisture-absorbent fabric material on a flat surface and using a computer-numerically-controlled (CNC) based fabric cutting machine table, or like machine, configured and programmed to cut fabric material so that it meets its dimensions, and has a necessary set of hand/foot-insertable apertures, (b) using a CNC-based sewing machine table to make and apply stitches to the fabric material to reinforce each hand/foot-insertable aperture, and form necessary reinforcements between the hand/foot-insertable apertures, and (c) applying finishing operations to the fabric material using a CNC-based inspection and finishing machine table, or like machine, configured and programmed to produce the isometric-exercise towel of the first embodiment of the present invention, in a fully-automated or semi-automated manner using as many human workers as may be required or prescribed;

FIGS. 8A1 and 8A2 set forth schematic illustrations showing how the isometric-exercise towel of the second illustrative embodiment of the present invention, depicted in FIGS. 7A and 7B, is folded along its latitudinal axis, so that when folded that the apertures on the latitudinal ends are spatially aligned for insertion of the user's hands and/or feet, as described hereinafter;

FIGS. 8B1 and 8B2 set forth schematic illustrations showing how the isometric-exercise towel of the second illustrative embodiment of the present invention, depicted in FIGS. 7A and 7B, is folded along its longitudinal axis, so that when folded the apertures on the longitudinal sides are spatially aligned for insertion of the user's hands and/or feet, as described hereinafter;

FIG. 9 is a flow chart describing the primary steps involved in manufacturing the isometric-exercise towel of the second illustrative embodiment of the present invention, comprising (a) positioning a piece of moisture-absorbent fabric material on a flat surface and using a CNC-based fabric cutting machine table to cut it so that it meets its dimensions, and has necessary the hand/foot-insertable apertures, and also positioning a piece of canvass material on the table to be cut into two pieces with hand/foot-insertable apertures, for each isometric-exercise towel to be manufactured, (b) using a CNC-based sewing machine table to apply stitches to the fabric material to reinforce each hand/foot-insertable aperture, form necessary reinforcements between the hand/foot-insertable apertures, and (c) applying finishing operations to the fabric material using a CNC-based inspection and finishing machine table to produce the isometric-exercise towel of the second embodiment of the present invention;

FIGS. 9B1 and 9B2 is provide perspective views illustrating the steps used to assemble the pieces of fabric and canvass prior to sewing and stitching operations so as to construct the isometric-exercise towel of the second illustrative embodiment of the present invention, having structurally-reinforced hand-foot-insertable apertures formed in the corners of the isometric-exercise towel;

FIG. 9C is a first perspective view of stitches made about the inside perimeter of a hand/foot-insertable aperture formed in isometric-exercise towel of FIGS. 7A and 7B, using the CNC fabric sewing machine table illustrated in FIG. 9B;

FIG. 10A is a plan view of the third illustrative embodiment of the isometric-exercise towel of the present invention, constructed from a layer of moisture-absorbent material and two pieces of pliant canvass material so as to have (i) a thick woven pile offering excellent moisture-wicking characteristics, (ii) four hand/foot-insertable apertures formed in the corners of the isometric-exercise towel, reinforced with double stitching about the perimeter of each hand/foot-insertable aperture, and (iii) a reinforced stitching pattern between pairs of hand/foot-insertable apertures formed on opposing ends of the isometric-exercise towel;

FIG. 10B is a cross-sectional view of the third illustrative embodiment of the isometric-exercise towel of the present invention, illustrating its thick woven pile, and hand/foot-insertable apertures formed in the corner regions and central region of the isometric-exercise towel, structurally reinforced with double stitching about the inner perimeter of each hand/foot-insertable aperture;

FIGS. 11A1 and 11A2 set forth schematic illustrations showing how the isometric-exercise towel of the third illustrative embodiment of the present invention, depicted in FIGS. 10A and 10B, is folded along its latitudinal axis, so that when folded the apertures on the latitudinal ends are spatially aligned for insertion of the user's hands or feet, as described hereinafter;

FIGS. 11B1, 11B2 and 11B3 set forth schematic illustrations showing how the isometric-exercise towel of the third illustrative embodiment of the present invention, depicted in FIGS. 10A and 10B, is folded along its longitudinal axis, so that when folded the apertures on the longitudinal sides are spatially aligned for insertion of the user's hands or feet, as described hereinafter;

FIGS. 12B1 and 12B2 provide perspective views illustrating the steps used to assemble the pieces of fabric and canvass prior to sewing and stitching operations so as to construct the isometric-exercise towel of the third illustrative embodiment of the present invention;

FIG. 12C is a cross-sectional view of stitches made about the inside perimeter of a hand/foot-insertable aperture formed in isometric-exercise towel of FIGS. 10A and 10B, using the CNC fabric sewing machine table illustrated in FIG. 12D;

FIGS. 14A1 and 14A2 set forth schematic illustrations showing how the isometric-exercise towel of the fourth illustrative embodiment of the present invention, depicted in FIGS. 13A and 13B, is folded along its latitudinal axis, so that the apertures on the latitudinal ends are spatially aligned for insertion of the user's hands or feet, as described hereinafter;

FIGS. 14B1 and 14B2 set forth schematic illustrations showing how the isometric-exercise towel of the fourth illustrative embodiment of the present invention, depicted in FIGS. 13A and 13B, is folded along its longitudinal axis, so that the apertures on the longitudinal sides are spatially aligned for insertion of the user's hands or feet, as described hereinafter;

FIG. 15 is a flow chart describing the primary steps involved in manufacturing the isometric-exercise towel of the fourth illustrative embodiment of the present invention, comprising (a) positioning a piece of moisture-absorbent fabric material on a flat surface and using a CNC-based fabric cutting machine table to cut it so that it meets its dimensions, and has necessary the hand/foot-insertable apertures, and also positioning a piece of canvas material on the table to be cut into two pieces with hand/foot-insertable apertures, for each isometric-exercise towel to be manufactured, (b) using a CNC-based sewing machine table to apply stitches to the fabric material to reinforce each hand/foot-insertable aperture, form necessary reinforcements between the hand/foot-insertable apertures, and (c) applying finishing operations to the fabric material using a CNC-based inspection and finishing machine table to produce the isometric-exercise towel of the fourth embodiment of the present invention;

FIGS. 16B1 and 16B2 illustrate the steps used to assemble the pieces of fabric and canvass prior to sewing and stitching operations so as to construct the isometric-exercise towel of the fourth illustrative embodiment of the present invention;

FIG. 18 is a graphical illustration of a graphical user interface (GUI) screen showing a door hook being used to store the isometric-exercise towel of the present invention;

FIG. 19 is a graphical illustration of a GUI screen showing a person using a door hook to perform a first isometric exercise in accordance with principles of the present invention;

FIG. 20 is a graphical illustration of a GUI screen showing a person using the top surface of a door to perform an isometric exercise using the isometric-exercise towel of the present invention;

FIG. 33 is a graphical illustration of a GUI screen showing a person inserting both hands within the first pair of folded hand/foot-insertable apertures in the isometric-exercise towel of the present invention, while kneeling on the middle region of the isometric-exercise towel, as the person's feet are inserted within the opposing pair of hand/foot-insertable apertures thereof, so as to perform an isometric exercise using the same by stretching the isometric-towel in a direction indicated by the force vector present in the graphical illustration; and FIG. 34 is a graphical illustration of a GUI screen showing a person inserting his right hand within the hand/foot-insertable aperture in one end of the isometric-exercise towel of the present invention, while his left hand is inserted within the opposing hand/foot-insertable aperture, while the isometric-exercise towel is suspended behind the person's head, so as to perform an isometric exercise using the same by stretching the isometric-towel in a direction indicated by the force vector present in the graphical illustration.

DETAILED DESCRIPTION OF THE ILLUSTRATIVE EMBODIMENTS OF THE PRESENT INVENTION

In each of the illustrative embodiments of the present invention, a new and improved apparatus is provided for performing diverse sets of isometric exercises, while remaining dry from perspiration produced during a physical workout, or otherwise refreshed from the feeling obtained when wiped down using a flush, soft moisture-absorbent towel.

In the first illustrative embodiment depicted in FIGS. 4A through 6D, the apparatus is realized in the form of a novel isometric-exercise towel constructed from a single layer of moisture-absorbent material, and stitched so as to provide reinforcement about each hand/foot-insertable aperture formed in one of its corners. As will be illustrated in great detail hereinafter, this portable apparatus can be used in an unfolded configuration, or in a folded as shown in FIGS. 5A and 5B, and may be stored in a folded manner or rolled up clipped or banded to retain the form of a rolled up apparatus.

Figures 7A, 7B:
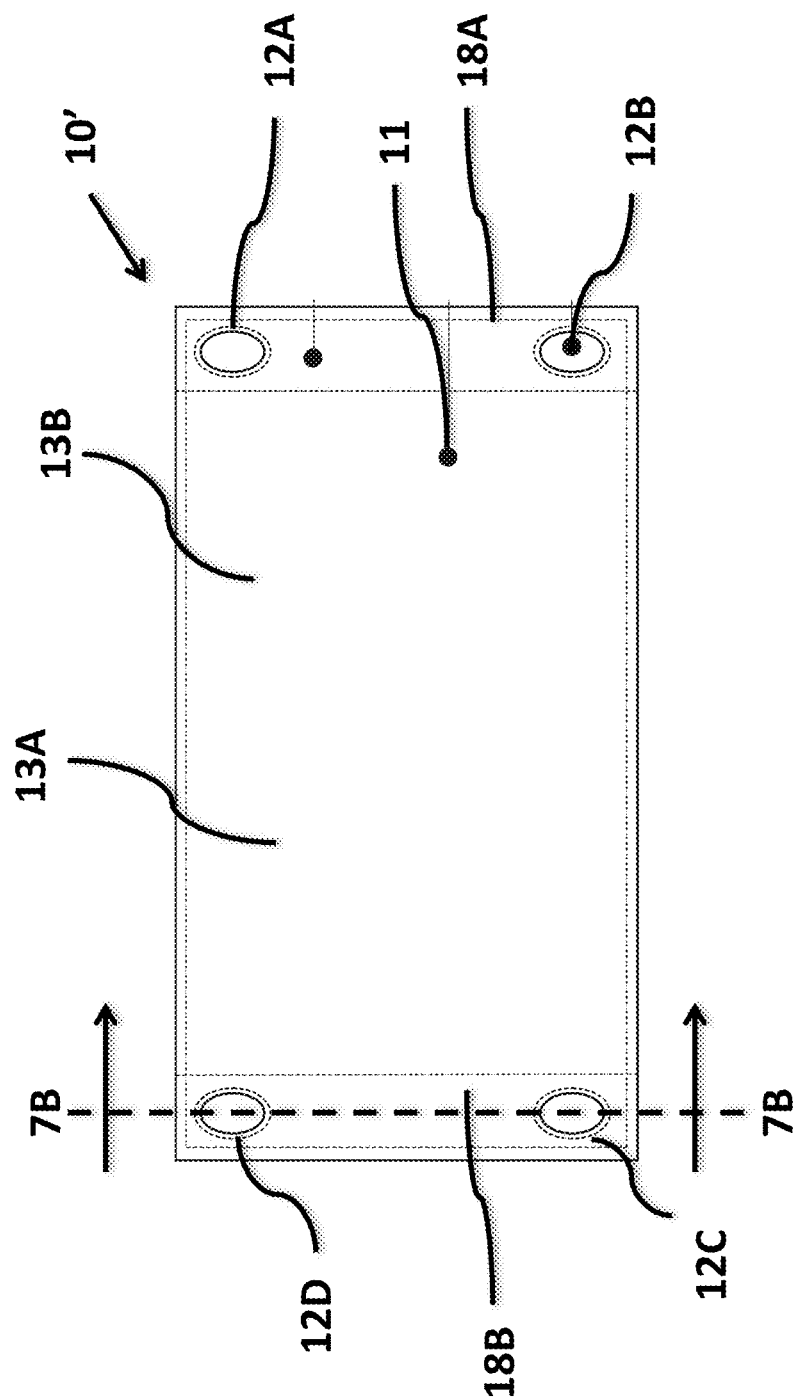
FIG. 7A is a plan view of the second illustrative embodiment of the isometric-exercise towel of the present invention, constructed from (i) a layer of moisture absorbent material (e.g. Terricloth) having a thick woven pile offering excellent moisture-wicking characteristics, and (ii) two pieces of pliant canvass material used for reinforcing the ends of the layer of moisture-absorbent material in which the four hand/foot-insertable apertures are formed in the corners of the isometric-exercise towel, and reinforced with double stitching about the perimeter of each hand/foot-insertable aperture, and also reinforced with stitching between pairs of hand/foot-insertable apertures formed on opposing ends of the isometric-exercise towel.
FIG. 7B is a cross-sectional view of the second illustrative embodiment of the isometric-exercise towel of the present invention, illustrating its thick woven pile, hand/foot-insertable apertures, reinforced with double stitching about the perimeter thereof.

In a second illustrative embodiment depicted in FIGS. 7A and 7B, the apparatus is realized in the form of a novel isometric-exercise towel constructed from a single layer of moisture-absorbent material coupled to several pieces of pliant canvass material sewn together as taught in great detail herein, and having stitching reinforcement about each hand/foot-insertable aperture formed in one of its corners. As will be illustrated in great detail hereinafter, this portable apparatus can be used in an unfolded configuration, or in a folded as shown in FIGS. 8A and 8B, and may be stored in a folded manner or rolled up clipped or banded to retain the form of a rolled up apparatus.

In a third illustrative embodiment depicted in FIGS. 10A and 10B, the apparatus is realized in the form of a novel isometric-exercise towel constructed from a single layer of moisture-absorbent material, and several pieces of pliant canvass material sewn together as taught in great detail herein, to provide reinforcement about each hand/foot-insertable aperture formed in one of its corners. As will be illustrated in great detail hereinafter, this portable apparatus can be used in an unfolded configuration, or in a folded as shown in FIGS. 11A and 11B, and may be stored in a folded manner or rolled up clipped or banded to retain the form of a rolled up apparatus.

Figure 13A:
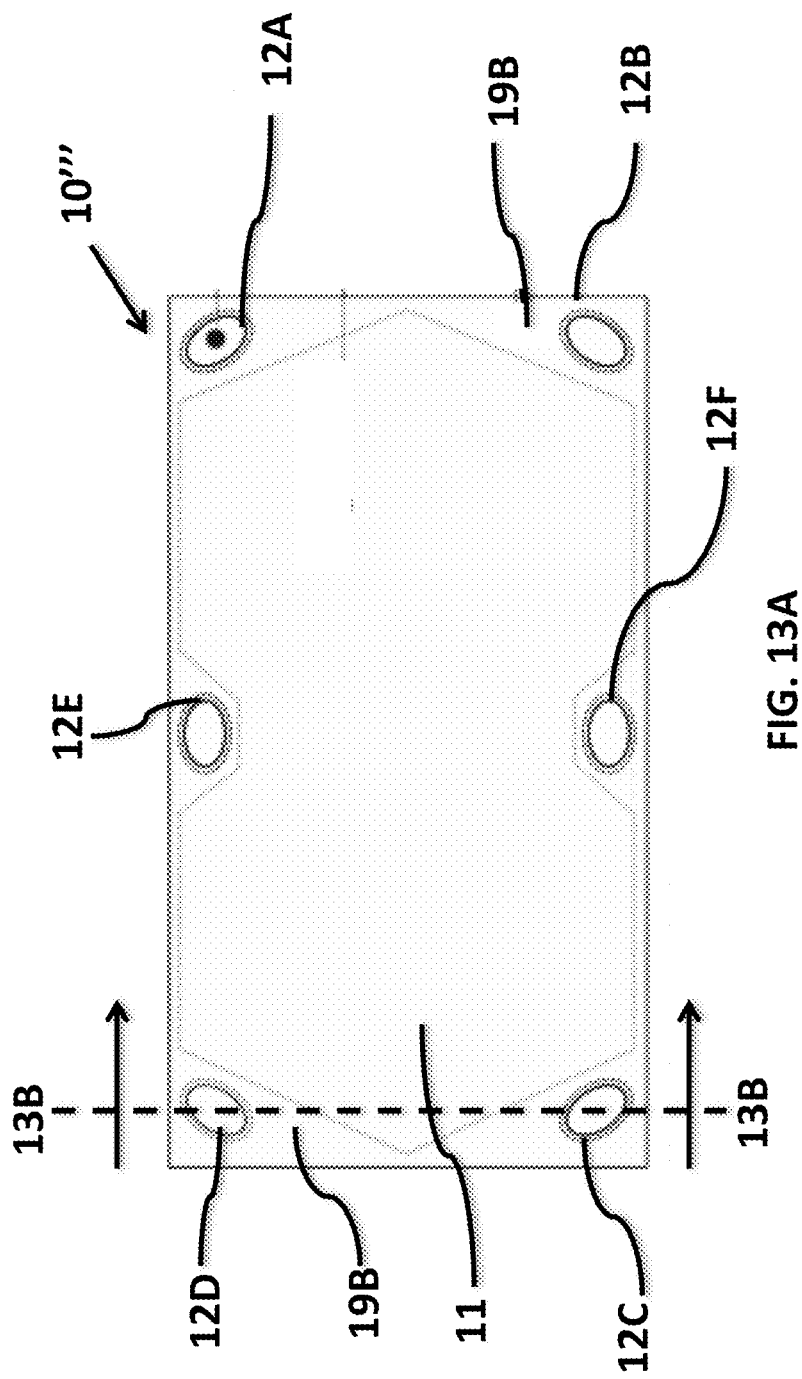
FIG. 13A is a plan view of the fourth illustrative embodiment of the isometric-exercise towel of the present invention, constructed from a layer of pliant canvass material and a layer of moisture-absorbent material (i) having a thick woven pile offering excellent moisture-wicking characteristics, (ii) six hand/foot-insertable apertures formed in the corners of the isometric-exercise towel, reinforced with double stitching about the perimeter of each hand/foot-insertable aperture, and (iii) a reinforced stitching pattern between pairs of hand/foot-insertable apertures formed on opposing ends of the isometric-exercise towel.
Figure 13B:
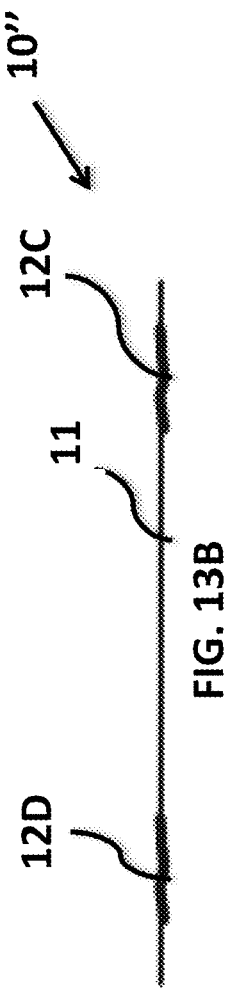
FIG. 13B is a cross-sectional view of the fourth illustrative embodiment of the isometric-exercise towel of the present invention, illustrating its thick woven pile, hand/foot-insertable apertures, reinforced with double stitching about the perimeter thereof.

In a fourth illustrative embodiment depicted in FIGS. 13A and 13B, the apparatus is realized in the form of a novel isometric-exercise towel constructed from a single layer of moisture-absorbent material coupled to several pieces of pliant canvass material sewn together as taught in great detail herein, to provide reinforcement about each hand/foot-insertable aperture formed in one of its corners. As will be illustrated in great detail hereinafter, this portable apparatus can be used in an unfolded configuration, or in a folded as shown in FIGS. 14A and 14B, and may be stored in a folded manner or rolled up clipped or banded to retain the form of a rolled up apparatus.

It is appropriate at this juncture to describe each of these illustrative embodiments in great technical detail, with reference to the Figure Drawings attached hereto.

Specification of the First Illustrative Embodiment of the Isometric-Exercise Towel of the Present Invention In FIGS. 4A and 4B, the first illustrative embodiment of the isometric-exercise towel of the present invention 10 is shown constructed from a layer of moisture-absorbent material 11 having: (i) a thick woven pile offering excellent moisture-wicking characteristics; (ii) four hand/foot-insertable apertures 12A through 12D formed in the corners of the isometric-exercise towel, reinforced with double stitching 14 about the perimeter of each hand/foot-insertable aperture; and (iii) a reinforced stitching pattern 13A and 13B between pairs of hand/foot-insertable apertures formed on opposing ends of the isometric-exercise towel 10.

Figure 4C:
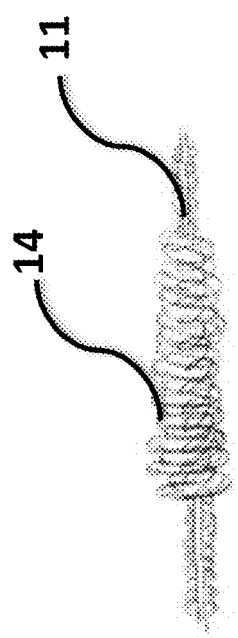
FIG. 4C is a cross-sectional view of the first illustrative embodiment of the isometric-exercise towel of the present invention, taken about a section of reinforcement stitching made through the moisture-absorbent fabric material, showing multiple stitches passing through and reinforcing the layer of moisture-absorbent material, along lines where the stitching is made.
Figure 4D:
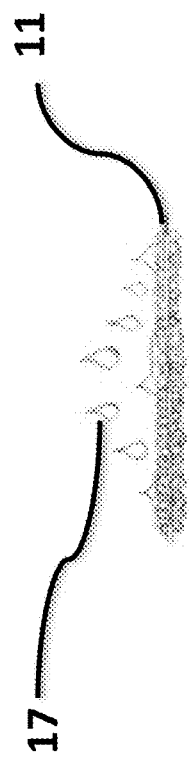
FIG. 4D is a cross-sectional view of the moisture-absorbent fabric material of the isometric-exercise towel of FIGS. 4A and 4B, illustrating the absorption of moisture within the fibers thereof.

FIG. 4C shows the reinforcement stitching 14 made through the moisture-absorbent fabric material of the isometric-exercise towel 10 of FIGS. 4A and 4B, showing multiple stitches passing through and reinforcing the layer of moisture-absorbent material 11, along lines where the stitching is made. In the illustrative embodiment, the CNC-operated sewing machine table 30 shown in FIG. 6B is used to make such reinforced stitches 14 in the moisture-absorbent fabric material 11 used to construction the isometric-exercise towel 10 of the present invention. FIG. 4D shows the cross-sectional nature of the moisture-absorbent fabric material 11 of the isometric-exercise towel of FIGS. 4A and 4B, illustrating the absorption of moisture 17 within the fibers thereof.

In the illustrative embodiments shown and described herein, the layer of moisture-absorbent material 11 is realized using a thick Terry clothe fabric with loops that can absorb large amounts of water and/or perspiration 17. The Terry clothe fabric can be manufactured by weaving or knitting. Typically, the fabric is woven on special looms that have two beams of longitudinal warp through which the filler or weft is fired laterally. The first industrial production of terrycloth towels was by the English manufacturer Christy, in 19850. The first "Christy" towels were shown at the Great Exhibition of 1852 at the Crystal Palace, London, England.

In general, there are two types of terry fabrics: Towell Terry; and French Terry. Towell Terry is a woven fabric with long loops that can absorb large amounts of water. Its content is usually 100% cotton, but may sometimes contain polyester. French Terry is a fabric often used in men's, women's and children's clothes. One of its sides is flat, while the other side is with cross loops. It is either 100% cotton or contains polyester with elastaine (Lycra). It is often warp knitted, and the term French Terry is colloquially used for all warp knitted Terry. In general, it is the length of the loops that determines how much fluid is absorbed by the cloth as longer loops provide more surface area to absorb and come in contact with the fluid.

While Terry fabric is a preferred fabric for constructing the isometric-exercise towel of the present invention, it is understood, however, that other kinds of natural and/or synthetic fabric material having suitable moisture-absorbing properties and characteristics, sufficient to wick perspiration away from a person's skin tissue, can be used to practice the present invention.

Figure 1A:
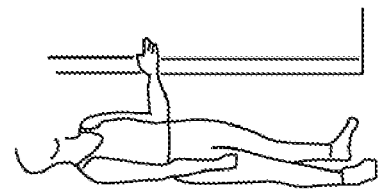
FIGS. 1A through 1F set forth a set of illustrations describing six different prior art isometric exercises performed by a person without the use of special-isometric apparatus.
Figure 1B:
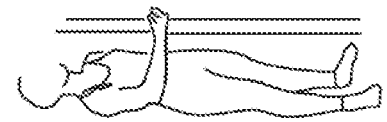
Figure 1C:
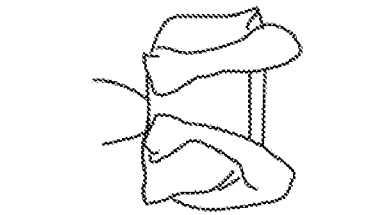
Figure 1D:
Figure 1E:
Figure 1F:
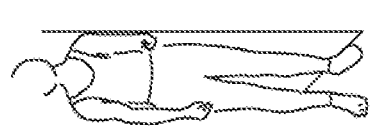
Figure 2:
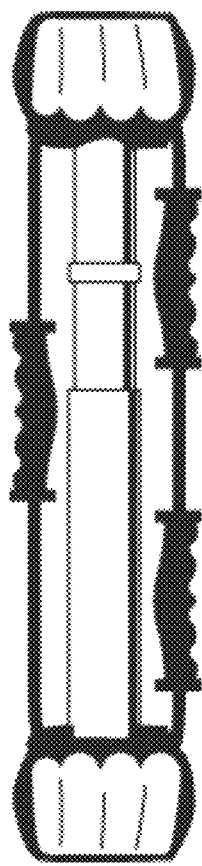
FIG. 2 is a schematic illustration of the prior art Steel Bow® Bullworker™ isometric apparatus allowing a person to push its two end-grips inwardly, or pull its hand-grips mounted on its cords, so as to perform isometric exercises while measuring and displaying on a visual scale, a measure of the force being applied by the person during isometric exercise.
Figure 3:
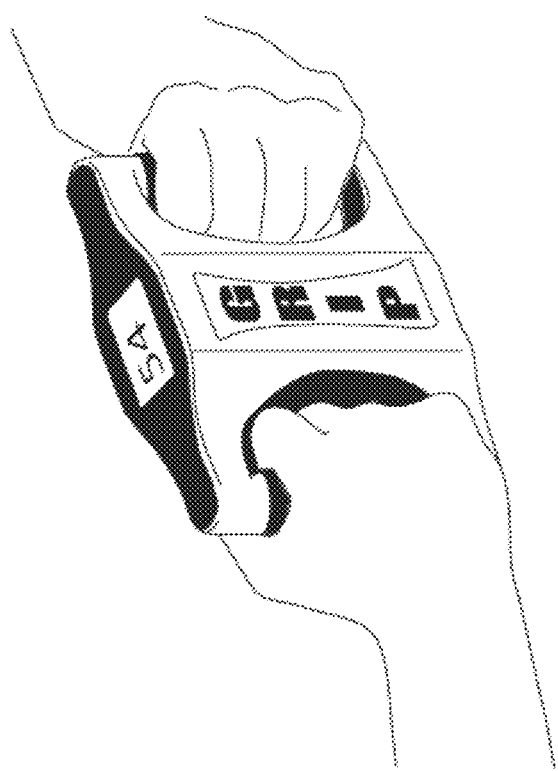
FIG. 3 is a schematic illustration of the prior art Grip™ isometric apparatus allowing a person to pull its two handgrips outwardly and or push inwardly to perform isometric exercises while measuring and displaying, on an LCD display, a measure of the force being applied by the person during isometric exercise.

FIGS. 5A1 and 5A2 show how the isometric-exercise towel of the first illustrative embodiment of the present invention 10 is folded along its latitudinal axis so that the apertures on the latitudinal ends are spatially aligned for insertion of the user's hands or feet, as described hereinafter.

FIGS. 5B1 and 5B2 show how the isometric-exercise towel of the first illustrative embodiment of the present invention 10 is folded along its longitudinal axis, so that the apertures on the longitudinal sides are spatially aligned for insertion of the user's hands or feet, as described hereinafter.

FIG. 6 describes the primary steps involved in manufacturing the isometric-exercise towel of the first illustrative embodiment of the present invention. As shown, the process comprises: (a) positioning a piece of moisture-absorbent fabric material on a flat surface 22 and using a CNC-based fabric cutting machine table 20 to cut it so that it meets its dimensions, and has necessary the hand/foot-insertable apertures; (b) using a CNC-based sewing machine table 30 to apply stitches 14 to the fabric material to reinforce each hand/foot-insertable aperture 12A through 12D, and form necessary reinforcements 13A, 13B between the hand/foot-insertable apertures 12A through 12D; and (c) applying finishing operations to the fabric material (e.g. Terri clothe) using a CNC-based inspection and finishing machine table 30 to produce the isometric-exercise towel of the first embodiment 10.

Figure 6A:
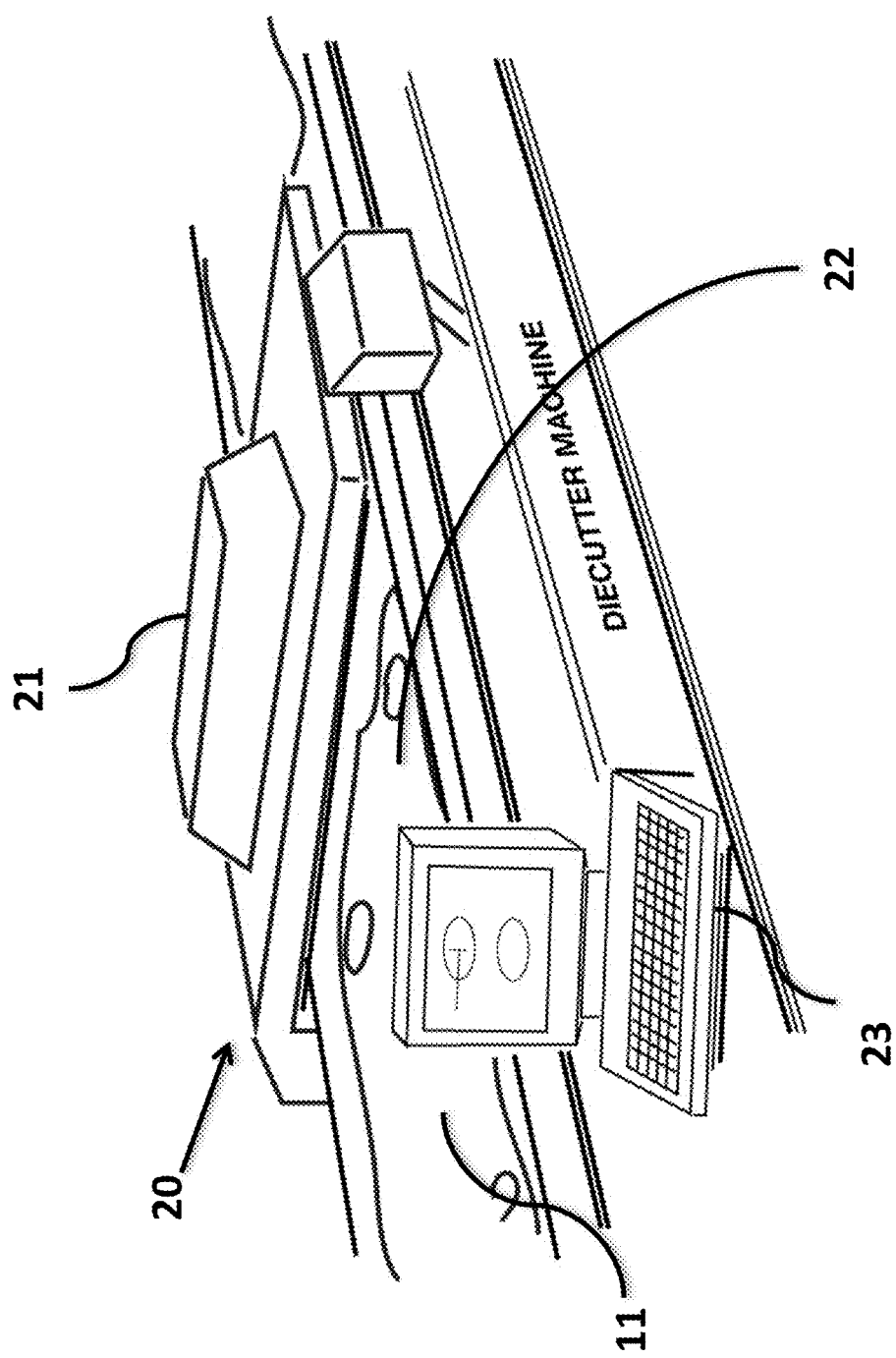
FIG. 6A is a perspective view of an exemplary CNC fabric cutting machine table supporting a fabric cutting head, used to cut and trim the moisture absorbent fabric used to construct the isometric-exercise towel of the first illustrative embodiment of the present invention.
Figure 6B:
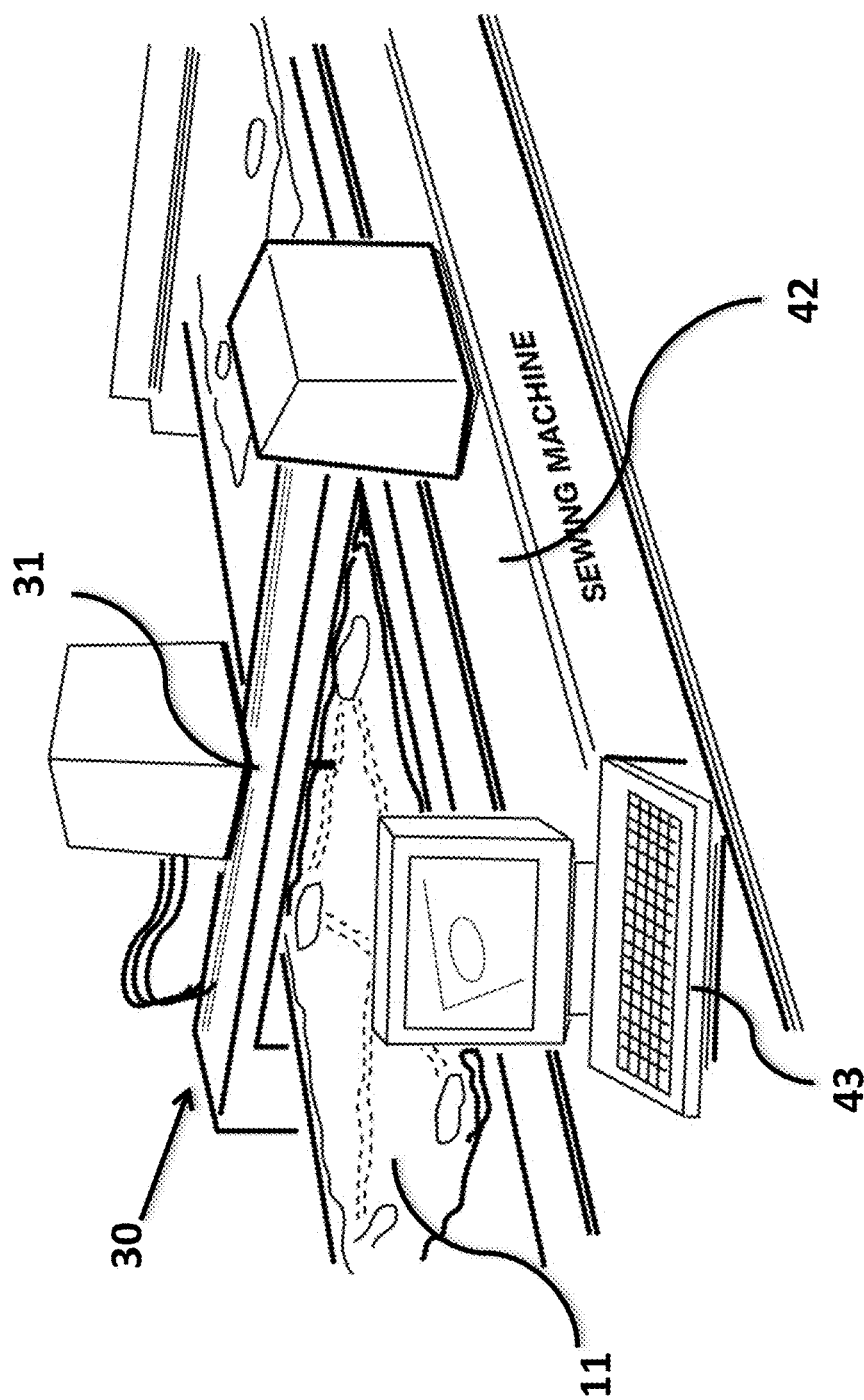
FIG. 6B is a perspective view of an exemplary CNC fabric sewing machine table supporting a fabric sewing head, configured and programmed to make stitches in moisture absorbent fabric used to construct the isometric-exercise towel of the first illustrative embodiment of the present invention.

FIG. 6A shows the CNC fabric cutting machine table 30 supporting a fabric cutting head 31, used to cut and trim the moisture absorbent fabric material that is used to construct the isometric-exercise towel of the first illustrative embodiment 10. The machine 30 includes a robotic gantry 42 supporting the sewing head 31 and a user console and computer 43, in a manner known in the art.

FIG. 6B shows the CNC fabric sewing machine table 30 supporting a fabric sewing head 31, used to make stitches 14 in moisture-absorbent fabric 11 used to construct the isometric-exercise towel of the first illustrative embodiment 10.

Figure 6C:
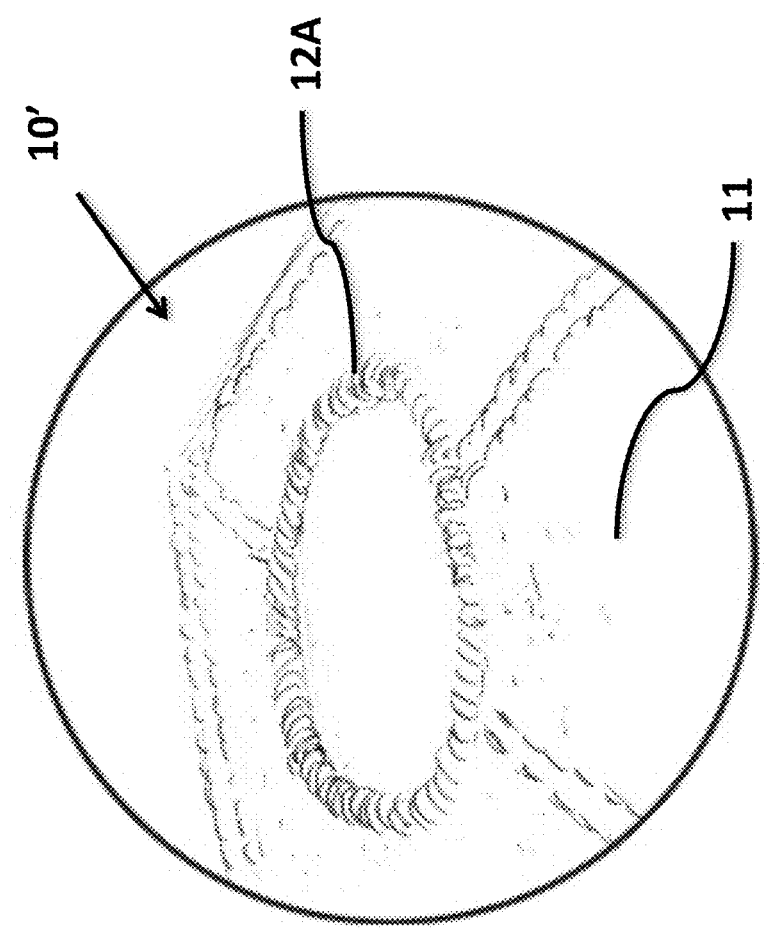
FIG. 6C is a first perspective view of stitches made about the inside perimeter of a hand/foot-insertable aperture formed in the corner region of the isometric-exercise towel of FIGS. 4A and 4B, using the CNC fabric sewing machine table illustrated in FIG. 6B.
Figure 6D:
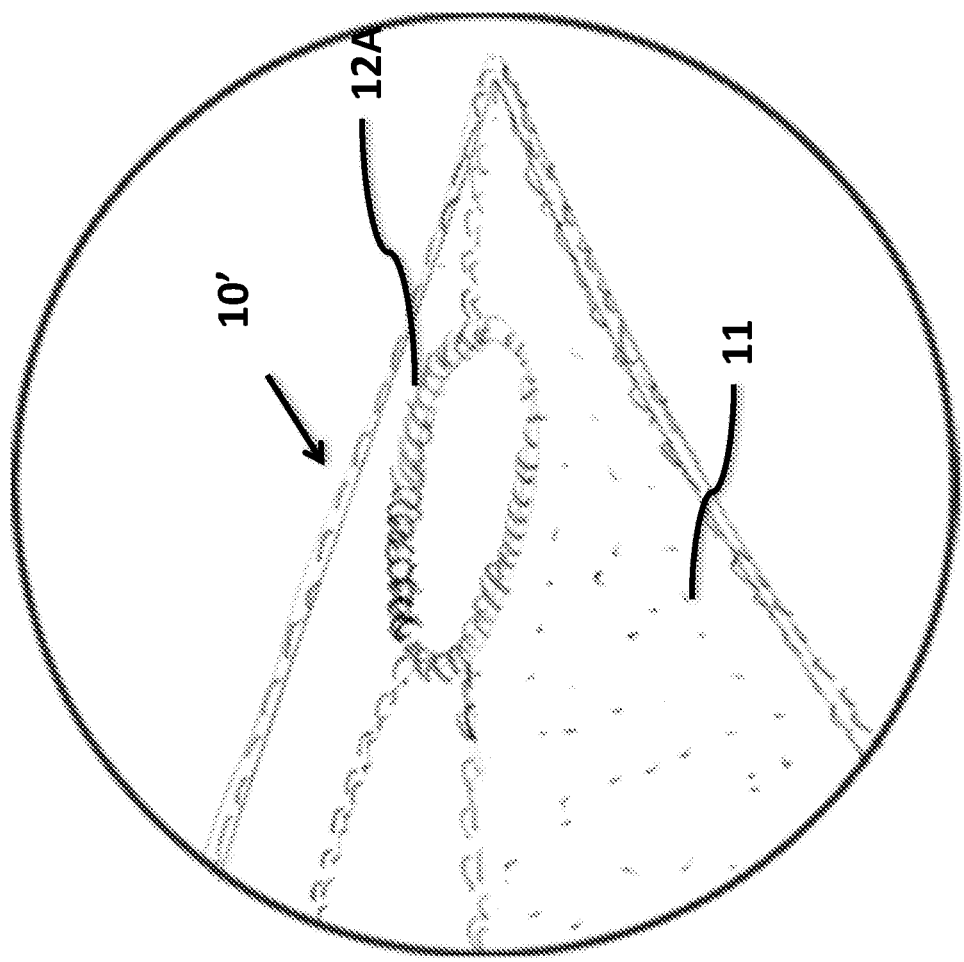
FIG. 6D is a second perspective view of stitches made about the inside perimeter of a hand/foot-insertable aperture formed in the corner region of the isometric-exercise towel of FIGS. 4A and 4B, using the CNC fabric sewing machine table illustrated in FIG. 6B.

FIGS. 6C and 6D shows stitches 14 made about the inside perimeter of a hand/foot-insertable aperture formed in isometric-exercise towel of FIGS. 4A and 4B, using the CNC fabric sewing machine table 30 illustrated in FIG. 6B.

Specification of the Second Illustrative Embodiment of the Isometric-Exercise Towel of the Present Invention In FIGS. 7A and 7B, the second illustrative embodiment of the isometric-exercise towel of the present invention 10" is shown constructed from (i) a layer of moisture absorbent material (e.g. Terricloth) 11 having a thick woven pile offering excellent moisture-wicking characteristics, and two pieces of pliant canvass material 18A, 18B for reinforcing the ends of the layer of moisture-absorbent material in which the four hand/foot-insertable apertures 12A through 12D are formed in the corners of the isometric-exercise towel 10', and reinforced with double stitching 14 about the perimeter of each hand/foot-insertable aperture (12), and reinforcement stitching 13A, 13B between pairs of hand/foot-insertable apertures 12A, 12C, and 12B, 12D, formed on opposing ends of the isometric-exercise towel 10'.

FIGS. 8A1 and 8A2 show how the isometric-exercise towel of the second illustrative embodiment of the present invention 10', depicted in FIGS. 7A and 7B, is folded along its latitudinal axis, so that the apertures on the latitudinal ends are spatially aligned for insertion of the user's hands or feet, as described hereinafter.

FIGS. 8B1 and 8B2 show how the isometric-exercise towel of the second illustrative embodiment 10', depicted in FIGS. 7A and 7B, is folded along its longitudinal axis, so that the apertures on the longitudinal sides are spatially aligned for insertion of the user's hands or feet, as described hereinafter.

FIG. 9 shows the primary steps involved in manufacturing process of the isometric-exercise towel of the second illustrative embodiment of the present invention. As shown the process comprises: (a) positioning a piece of moisture-absorbent fabric material 11 on a flat surface 31 and using a CNC-based fabric cutting machine table 30 shown in FIG. 9A to cut it so that it meets its dimensions, and when stitched and finished, has necessary the hand/foot-insertable apertures 12A through 12D, and also positioning a piece of canvas material 18 on the table to be cut into two pieces 18A, 18B with apertures for use in reinforcing the apertures 12A through 12D in each isometric-exercise towel being manufactured; (b) using a CNC-based sewing machine table 30 shown in FIG. 9D and to apply stitches to the fabric material to reinforce each hand/foot-insertable aperture 12A through 12D, and form necessary structural reinforcements 13A, 13B in the isometric-exercise towel between the hand/foot-insertable apertures 12A, 12C and 12B,12D; and (c) applying finishing operations to the fabric material using a CNC-based inspection and finishing machine table (not shown) to produce the isometric-exercise towel of the second embodiment 10'.

Figure 9A:
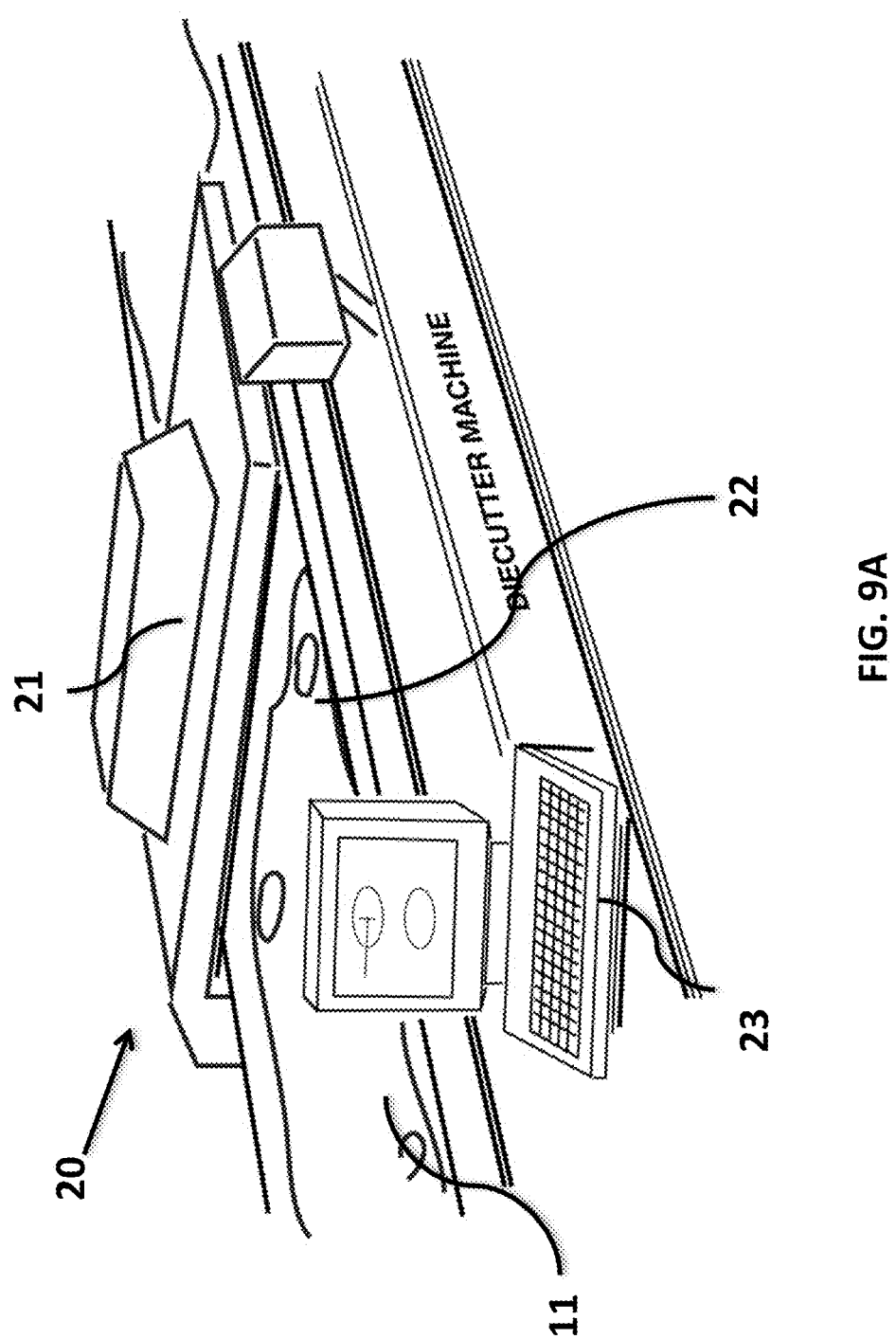
FIG. 9A is a perspective view of a CNC fabric cutting machine table supporting a fabric cutting head, used to cut and trim the moisture absorbent fabric used to construct the isometric-exercise towel of the second illustrative embodiment of the present invention.
Figure 9D:
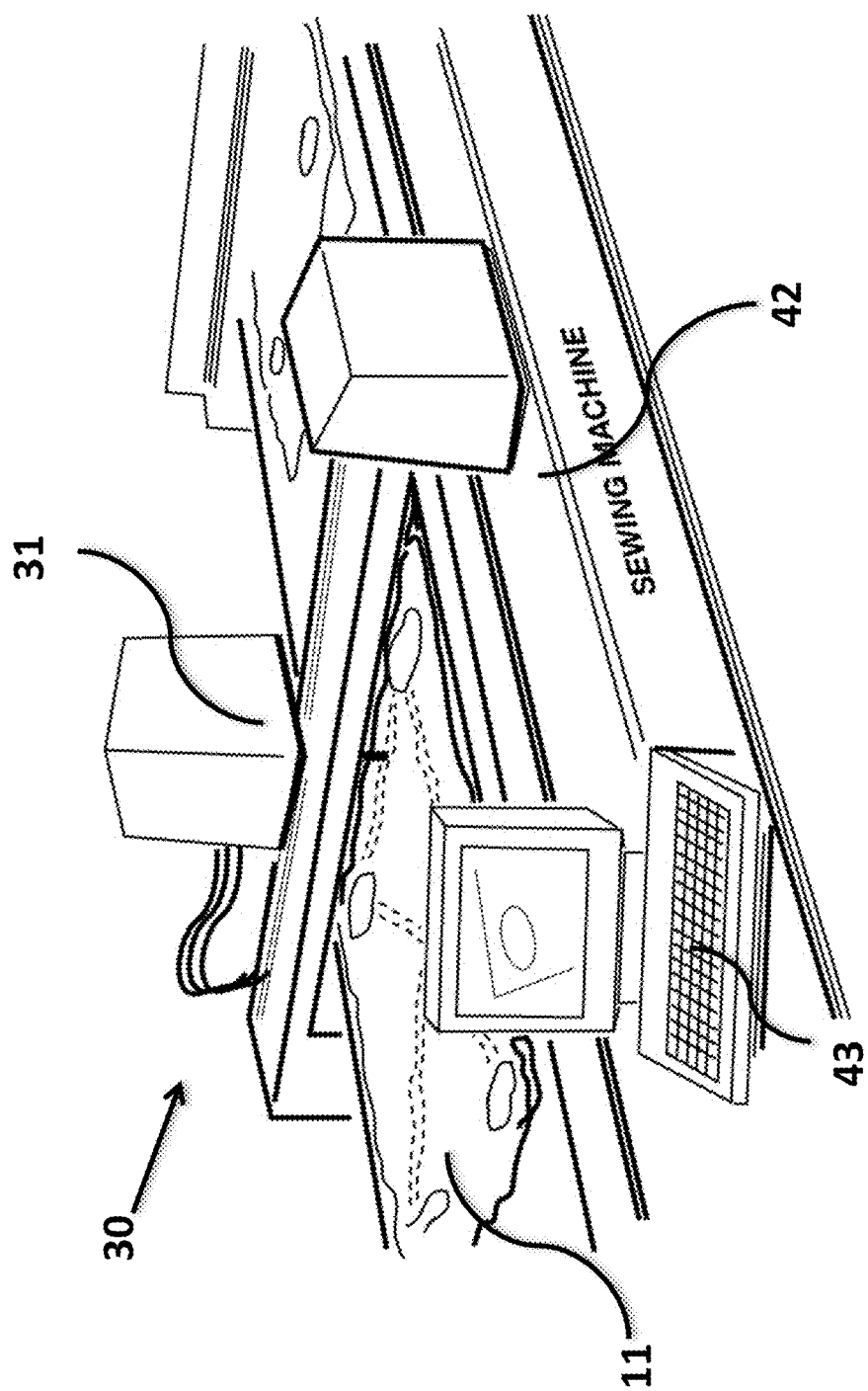
FIG. 9D is a perspective view of a CNC fabric sewing machine table used to construct the isometric-exercise towel of the second illustrative embodiment of the present invention.

FIG. 9C shows stitches 14 made about the inside perimeter of a hand/foot-insertable aperture 12A-12D formed in isometric-exercise towel of FIGS. 7A and 7B, using the CNC fabric sewing machine table illustrated in FIG. 9D.

Figure 9E:
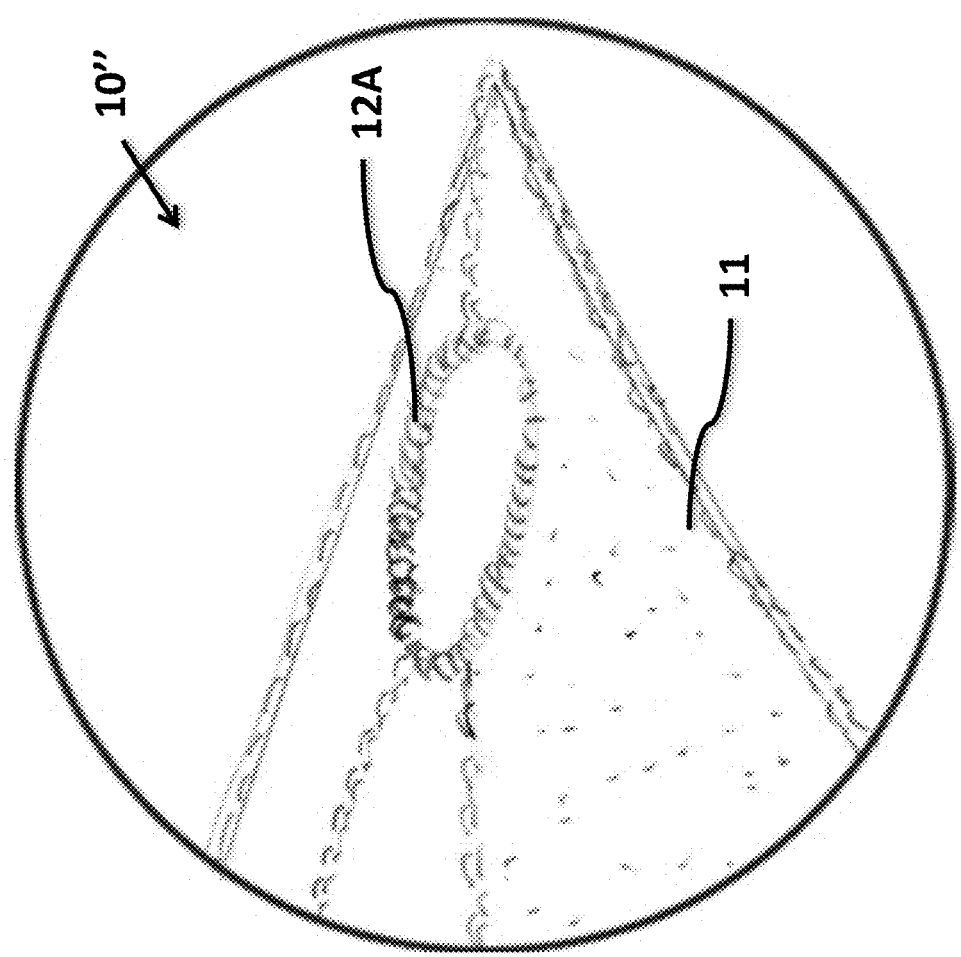
FIG. 9E is a first perspective view of stitches made about the inside perimeter of a hand/foot-insertable aperture formed in isometric-exercise towel of FIGS. 7A and 7B, using the CNC fabric sewing machine table illustrated in FIG. 9B.
Figure 9F:
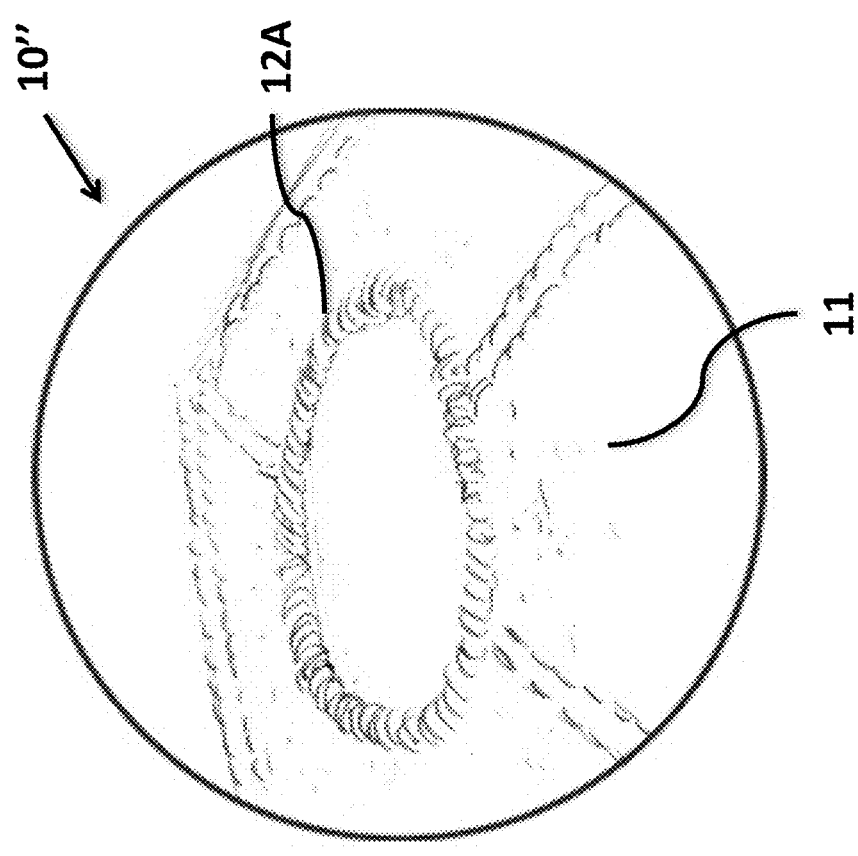
FIG. 9F is a second perspective view of stitches made about the inside perimeter of a hand/foot-insertable aperture formed in isometric-exercise towel of FIGS. 7A and 7B, using the CNC fabric sewing machine table illustrated in FIG. 9B.

FIGS. 9E and 9F show stitches 14 made about the inside perimeter of a hand/foot-insertable aperture formed in isometric-exercise towel of FIGS. 7A and 7B, using the CNC fabric sewing machine table 30 illustrated in FIG. 9D.

Specification of the Third Illustrative Embodiment of the Isometric-Exercise Towel of the Present Invention In FIGS. 10A and 10B, the third illustrative embodiment of the isometric-exercise towel of the present invention 10" is shown constructed from two cut pieces of pliant canvass material 18A, 18B and a layer of moisture-absorbent material 11 having a thick woven pile offering excellent moisture-wicking characteristics. When assembled together following the process of FIG. 12, the isometric-exercise towel 10" has (ii) four hand/foot-insertable apertures 12A through 12D formed in the corners of the isometric-exercise towel, and two hand/foot-insertable apertures 12E and 12F formed in the middle region thereof. Each aperture is reinforced with double stitching formed about the perimeter of each hand/foot-insertable aperture. Also, a reinforced stitching pattern is formed between pairs of hand/foot-insertable apertures on opposing ends of the isometric-exercise towel. This increases the structural integrity of the isometric-exercise towel during isometric exercises.

FIG. 10C shows the third illustrative embodiment of the isometric-exercise towel of the present invention 10", illustrating the double stitching about the perimeter of each hand/foot-insertable aperture.

FIGS. 11A1 and 11A2 show how the isometric-exercise towel of the third illustrative embodiment 10", depicted in FIGS. 10A and 10B, is folded along its latitudinal axis, so that the apertures on the latitudinal ends are spatially aligned for insertion of the user's hands or feet, as described hereinafter.

FIGS. 11B1, 11B2 and 11B3 show how the isometric-exercise towel of the third illustrative embodiment 10", depicted in FIGS. 10A and 10B, is folded along its longitudinal axis, so that the apertures on the longitudinal sides are spatially aligned for insertion of the user's hands or feet, as described hereinafter.

Figure 12:
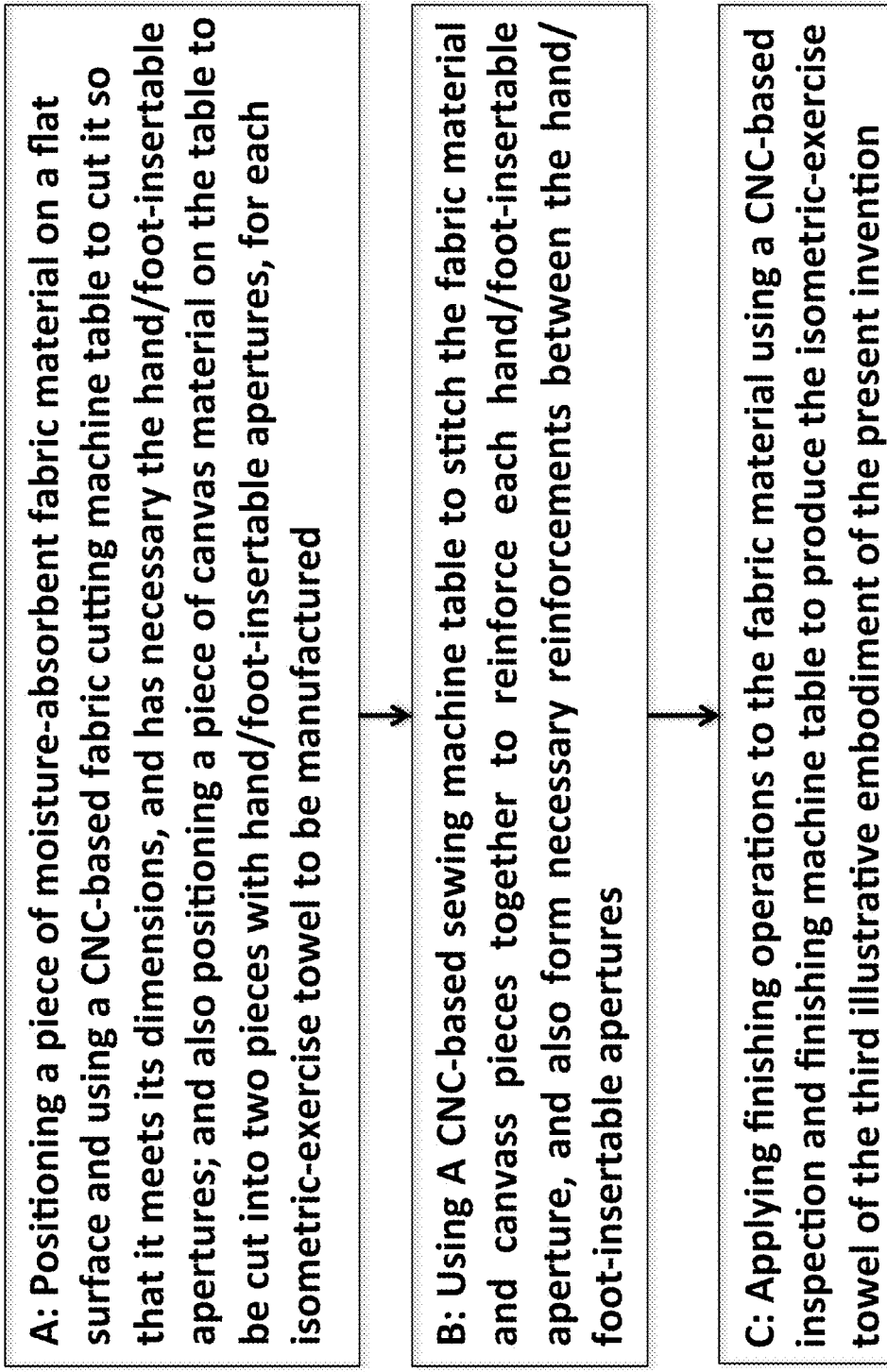
FIG. 12 is a flow chart describing the primary steps involved in manufacturing the isometric-exercise towel of the third illustrative embodiment of the present invention, comprising (a) positioning a piece of moisture-absorbent fabric material on a flat surface and using a CNC-based fabric cutting machine table to cut it so that it meets its dimensions, and has necessary the hand/foot-insertable apertures, and also positioning a piece of canvas material on the table to be cut into two pieces with hand/foot-insertable apertures, for each isometric-exercise towel to be manufactured, (b) using a CNC-based sewing machine table to apply stitches to the fabric material to reinforce each hand/foot-insertable aperture, form necessary reinforcements between the hand/foot-insertable apertures, and (c) applying finishing operations to the fabric material using a CNC-based inspection and finishing machine table to produce the isometric-exercise towel of the third embodiment of the present invention.

FIG. 12 describes the primary steps involved in manufacturing process for the isometric-exercise towel of the third illustrative embodiment 10", comprising: (a) positioning a piece of moisture-absorbent fabric material 11 on a flat surface 21 and using a CNC-based fabric cutting machine table 20 to cut it so that it meets its dimensions, and has necessary the hand/foot-insertable apertures, and also positioning a piece of canvas material 18 on the table to be cut into two pieces 18A, 18B with hand/foot-insertable apertures, for each isometric-exercise towel to be manufactured; (b) using a CNC-based sewing machine table 30 to apply stitches to the fabric material 11 to reinforce each hand/foot-insertable aperture, form necessary reinforcements between the hand/foot-insertable apertures 12A through 12D; and (c) applying finishing operations to the fabric material using a CNC-based inspection and finishing machine table to produce the isometric-exercise towel of the third embodiment of the present invention 10".

Figure 12A:
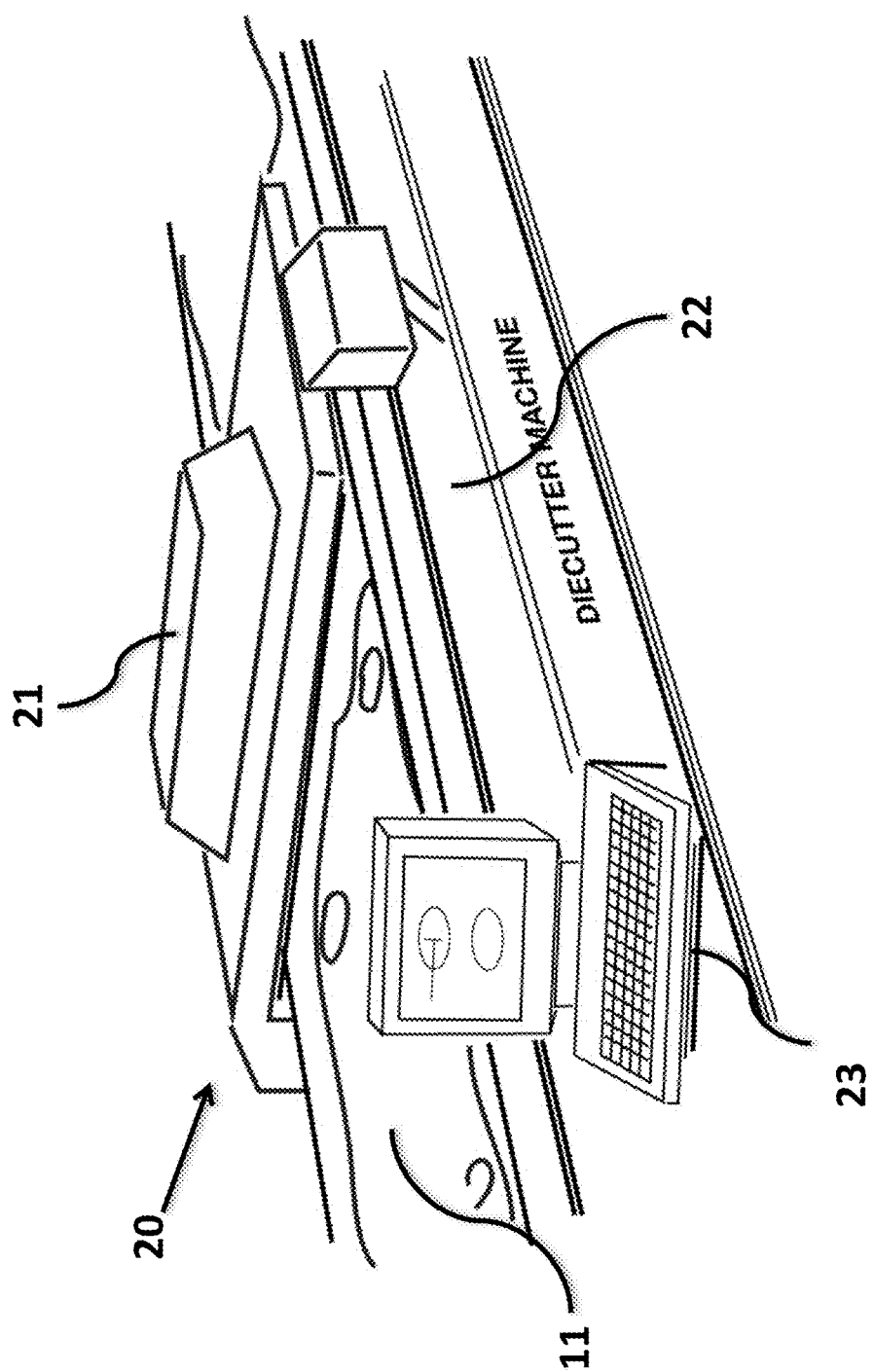
FIG. 12A is a perspective view of a CNC fabric cutting machine table supporting a fabric cutting head, used to cut and trim the moisture absorbent fabric used to construct the isometric-exercise towel of the third illustrative embodiment of the present invention.

FIG. 12A shows a CNC fabric cutting machine table supporting a fabric cutting head, used to cut and trim the moisture absorbent fabric used to construct the isometric-exercise towel of the third illustrative embodiment of the present invention.

FIG. 12B shows assemble the pieces of fabric prior 19A, 19B and 11 to sewing and stitching operations so as to construct the isometric-exercise towel of the third illustrative embodiment of the present invention 10".

FIG. 12C shows a CNC fabric sewing machine table 30 used to construct the isometric-exercise towel of the third illustrative embodiment 10".

Figure 12D:
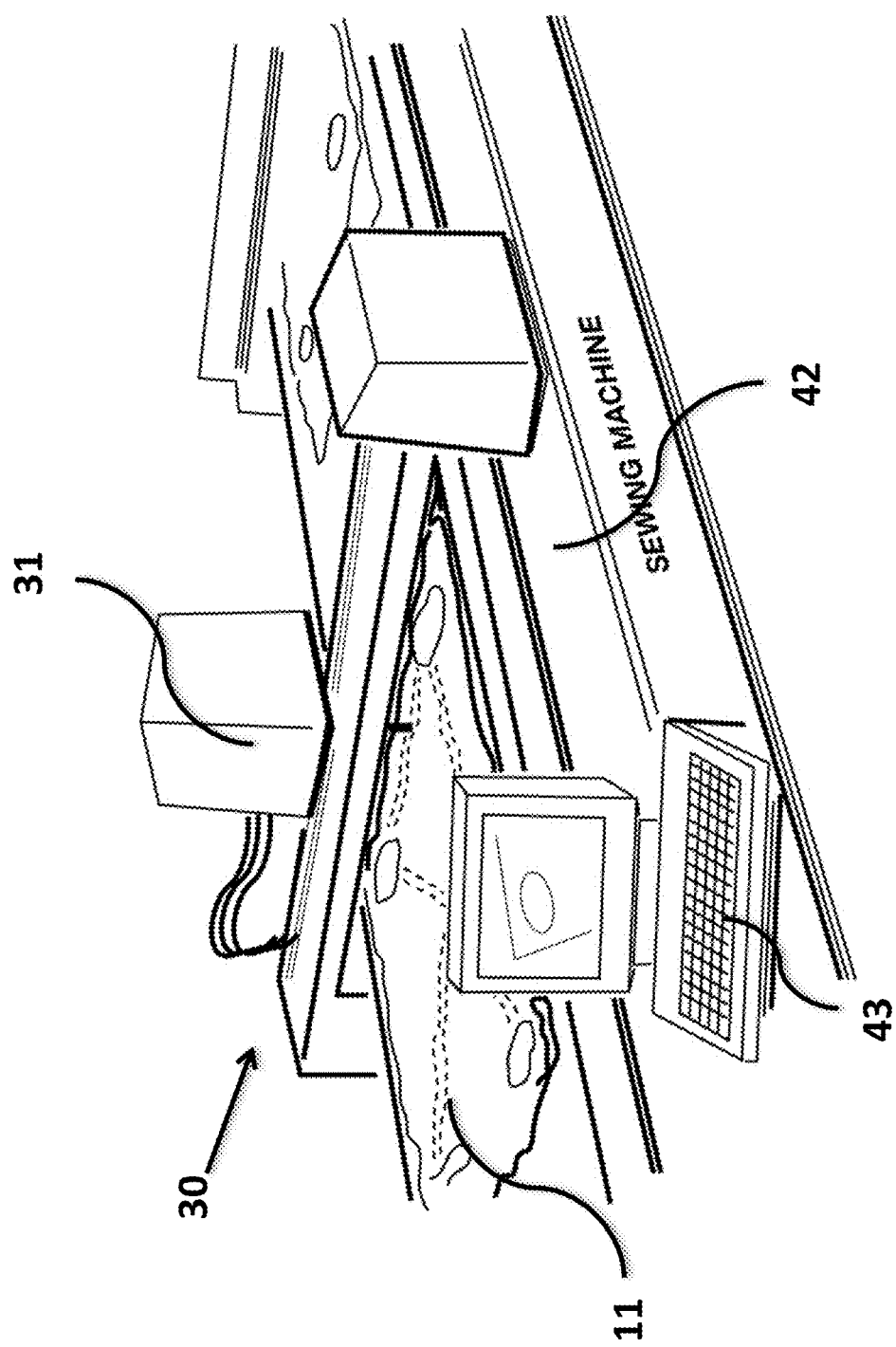
FIG. 12D is a perspective view of a CNC fabric sewing machine table used to construct the isometric-exercise towel of the third illustrative embodiment of the present invention.
Figure 12E:
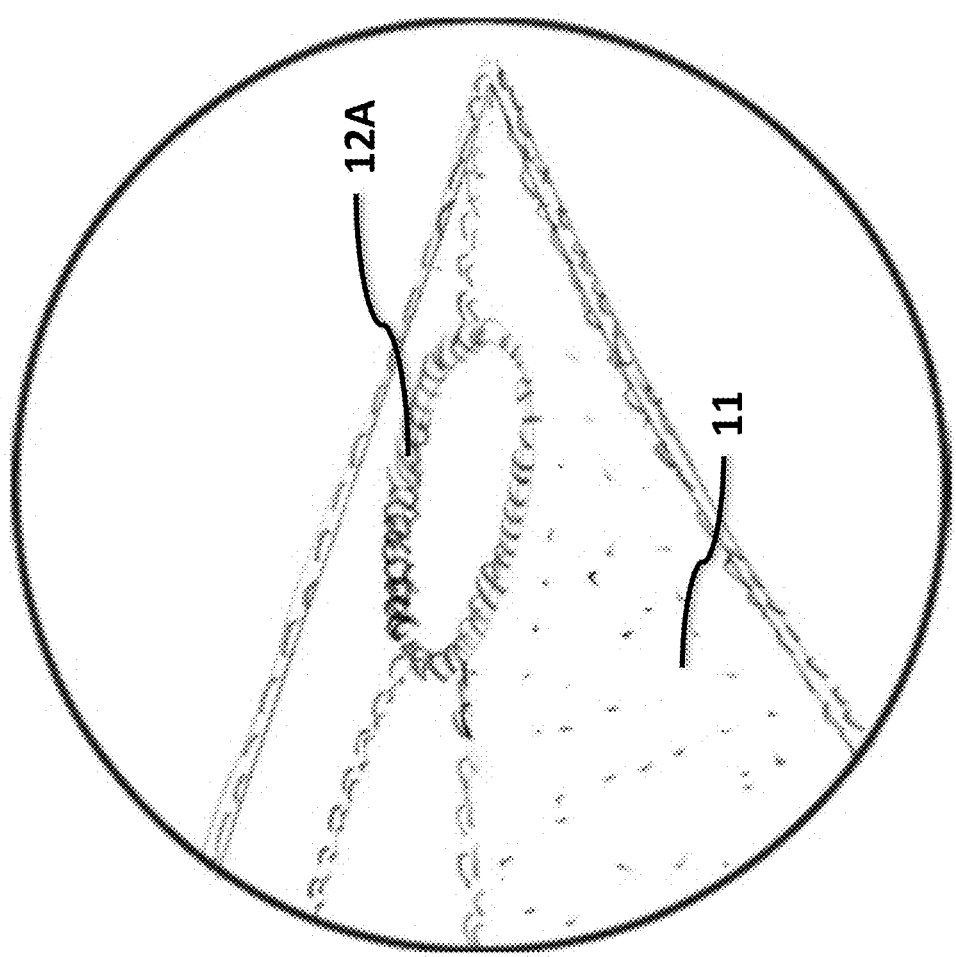
FIG. 12E is a first perspective view of stitches made about the inside perimeter of a hand/foot-insertable aperture formed in isometric-exercise towel of FIGS. 10A and 10B, using the CNC fabric sewing machine table illustrated in FIG. 12D.
Figure 12F:
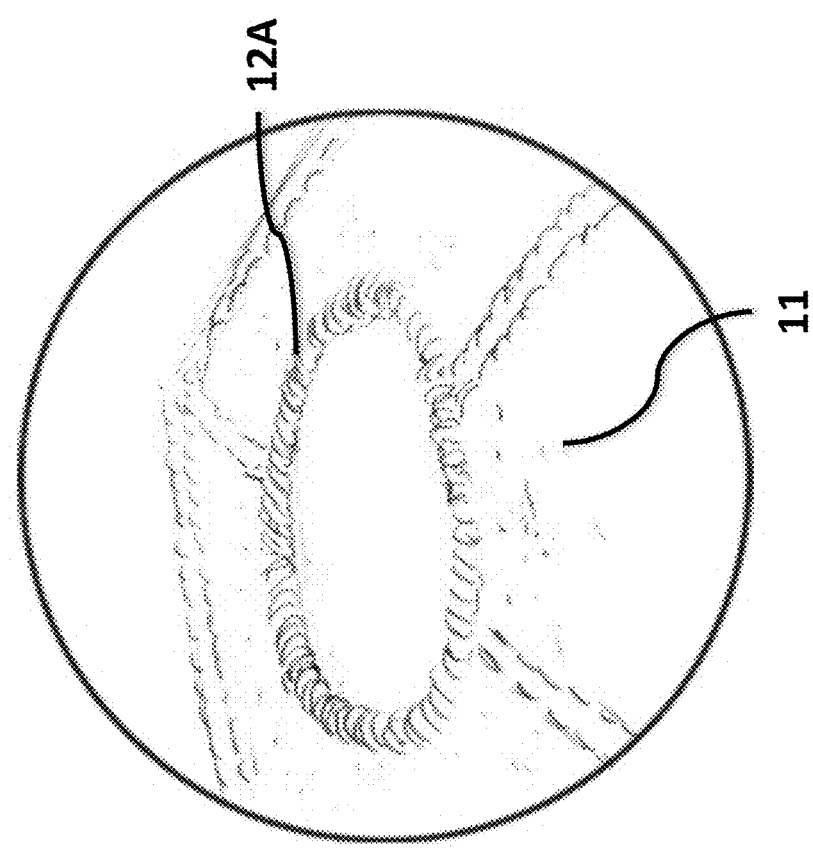
FIG. 12F is a second perspective view of stitches made about the inside perimeter of a hand/foot-insertable aperture formed in isometric-exercise towel of FIGS. 10A and 10B, using the CNC fabric sewing machine table illustrated in FIG. 12D.

FIGS. 12D and 12E show stitches 22 made about the inside perimeter of a hand/foot-insertable aperture 12A (through 12D and 12E and 12F) formed in isometric-exercise towel of FIGS. 10A and 10B, using the CNC fabric sewing machine table illustrated in FIG. 12D.

Specification of the Fourth Illustrative Embodiment of the Isometric-Exercise Towel of the Present Invention In FIGS. 13A and 13B, a fourth illustrative embodiment of the isometric-exercise towel of the present invention 10''' is shown constructed from a layer of moisture-absorbent material 11 and two pieces of precut pliant canvass material 18A and 18B. As shown, the isometric-exercise towel 10''' has: (i) a thick woven pile offering excellent moisture-wicking characteristics; (ii) four hand/foot-insertable apertures 12A through 12D formed in the corners of the isometric-exercise towel, and a pair of hand/foot-insertable apertures 12E and 12F formed on the side edges of the towel 10'''. Reinforced stitching patterns 13A, 13B can be formed between pairs of hand/foot-insertable apertures formed on opposing ends of the isometric-exercise towel to increase its strength.

FIGS. 14A1 and 14A2 show how the isometric-exercise towel of the fourth illustrative embodiment 10''' is folded along its latitudinal axis, so that the apertures on the latitudinal ends are spatially aligned for insertion of the user's hands or feet, as described hereinafter.

FIGS. 14B1 and 14B2 show how the isometric-exercise towel of the fourth illustrative embodiment 10''' is folded along its longitudinal axis, so that the apertures 12E and 12F on the longitudinal sides are spatially aligned for insertion of the user's hands or feet, as described hereinafter.

FIG. 15 describes the primary steps involved in manufacturing process for the isometric-exercise towel of the fourth illustrative embodiment 10''' comprising: (a) positioning a piece of moisture-absorbent fabric material 11 on a flat surface and using a CNC-based fabric cutting machine table 20 to cut it so that it meets its dimensions, and has necessary the hand/foot-insertable apertures, and also positioning a piece of canvas material on the table to be cut into two pieces with hand/foot-insertable apertures, for each isometric-exercise towel to be manufactured; (b) using a CNC-based sewing machine table 30 to apply stitches to the fabric material to reinforce each hand/foot-insertable aperture, form necessary reinforcements between the hand/foot-insertable apertures; and (c) applying finishing operations to the fabric material using a CNC-based inspection and finishing machine table to produce the isometric-exercise towel of the fourth embodiment of the present invention 10'''.

Figure 16A:
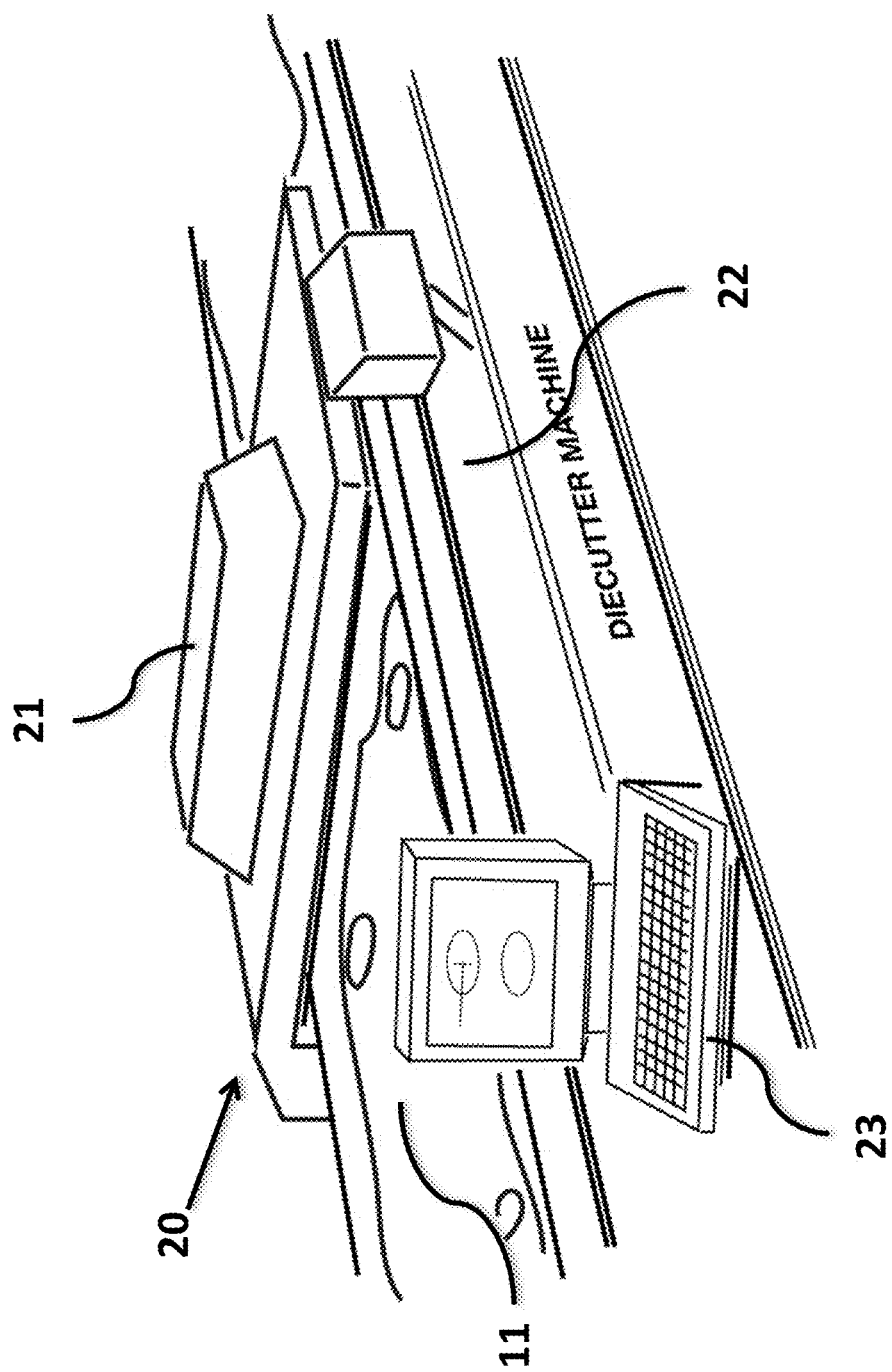
FIG. 16A is a perspective view of a CNC fabric cutting machine table supporting a fabric cutting head, used to cut and trim the moisture absorbent fabric used to construct the isometric-exercise towel of the fourth illustrative embodiment of the present invention.

FIG. 16A shows a CNC fabric cutting machine table 20 supporting a fabric cutting head 21, used to cut and trim the moisture absorbent fabric 11 used to construct the isometric-exercise towel of the fourth illustrative embodiment 10'''.

Figure 16B:
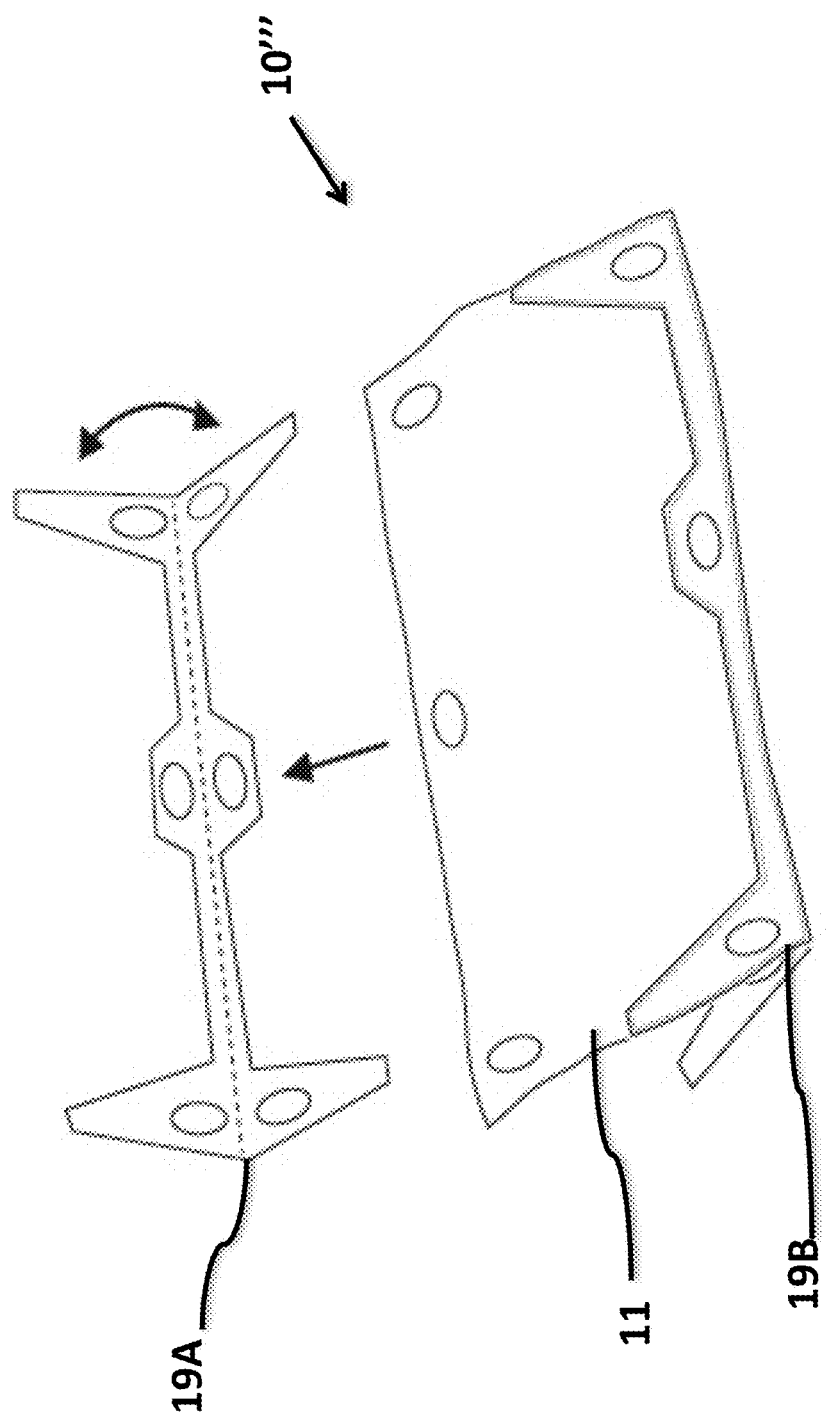

FIG. 16B shows the assembly the pieces of fabric 11, 19A, 19B prior to sewing and stitching operations so as to construct the isometric-exercise towel of the fourth illustrative embodiment 10'''.

Figure 16C:
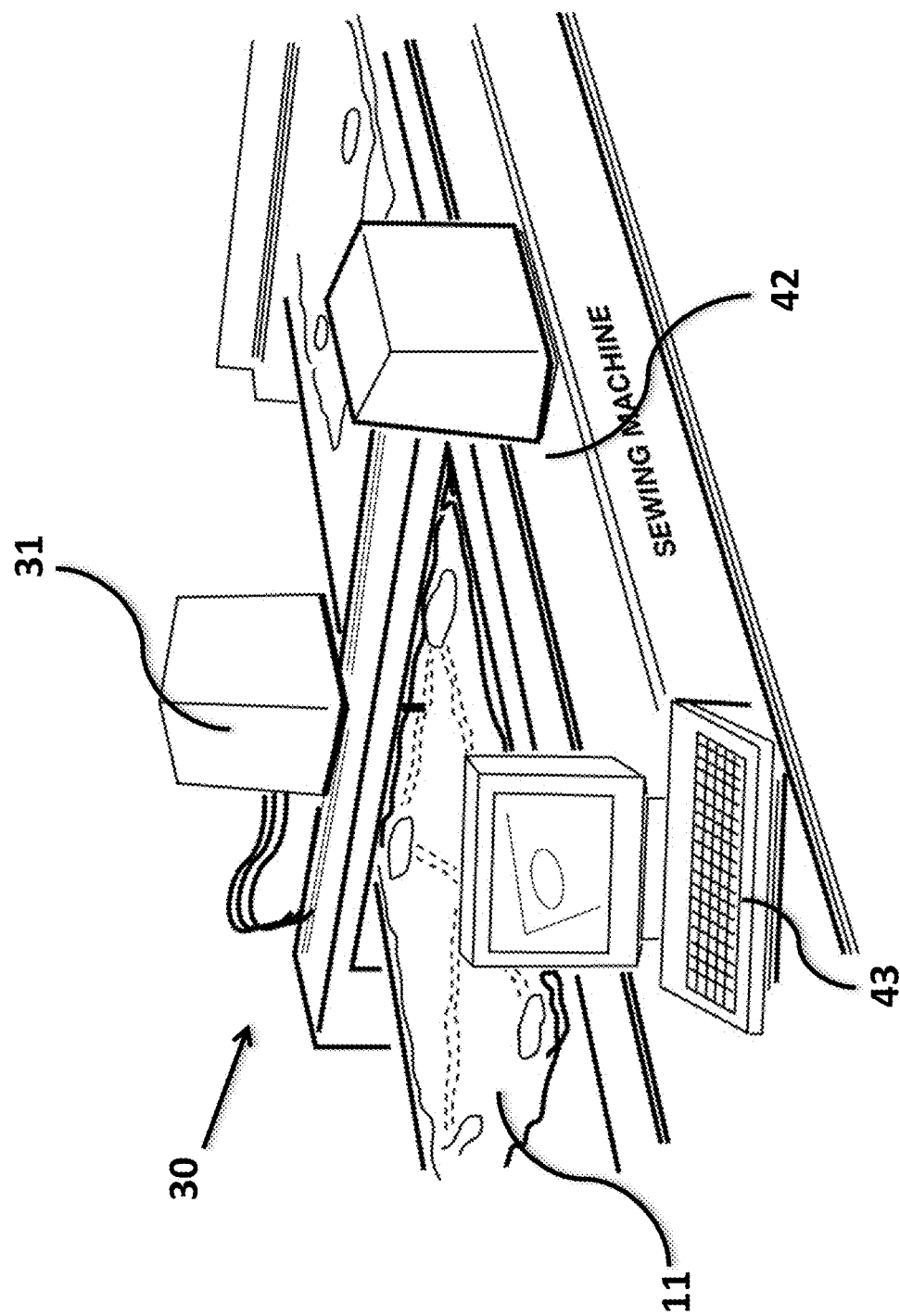
FIG. 16C is a cross-sectional view of stitches made about the inside perimeter of a hand/foot-insertable aperture formed in isometric-exercise towel of FIGS. 13A and 13B, using the CNC fabric sewing machine table illustrated in FIG. 16D.

FIG. 16C shows a CNC fabric sewing machine table 30 used to construct the isometric-exercise towel of the fourth illustrative embodiment 10'''.

Figure 16D:
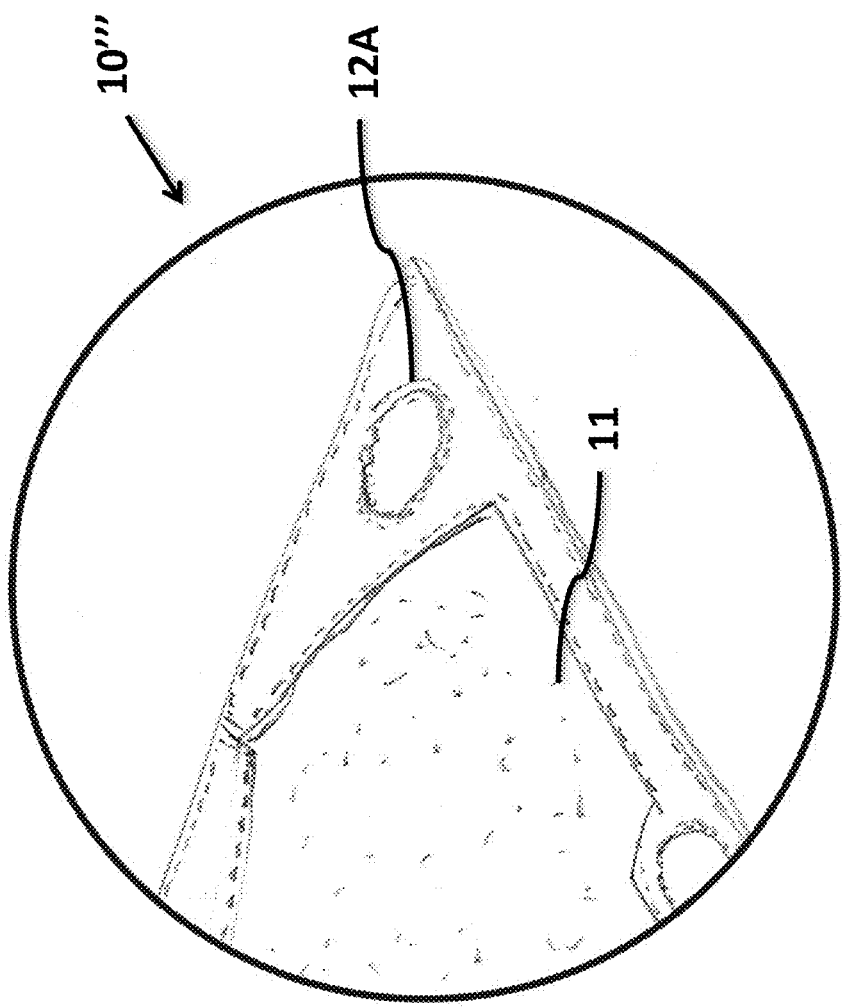
FIG. 16D is a perspective view of a CNC fabric sewing machine table used to construct the isometric-exercise towel of the fourth illustrative embodiment of the present invention.
Figure 16E:
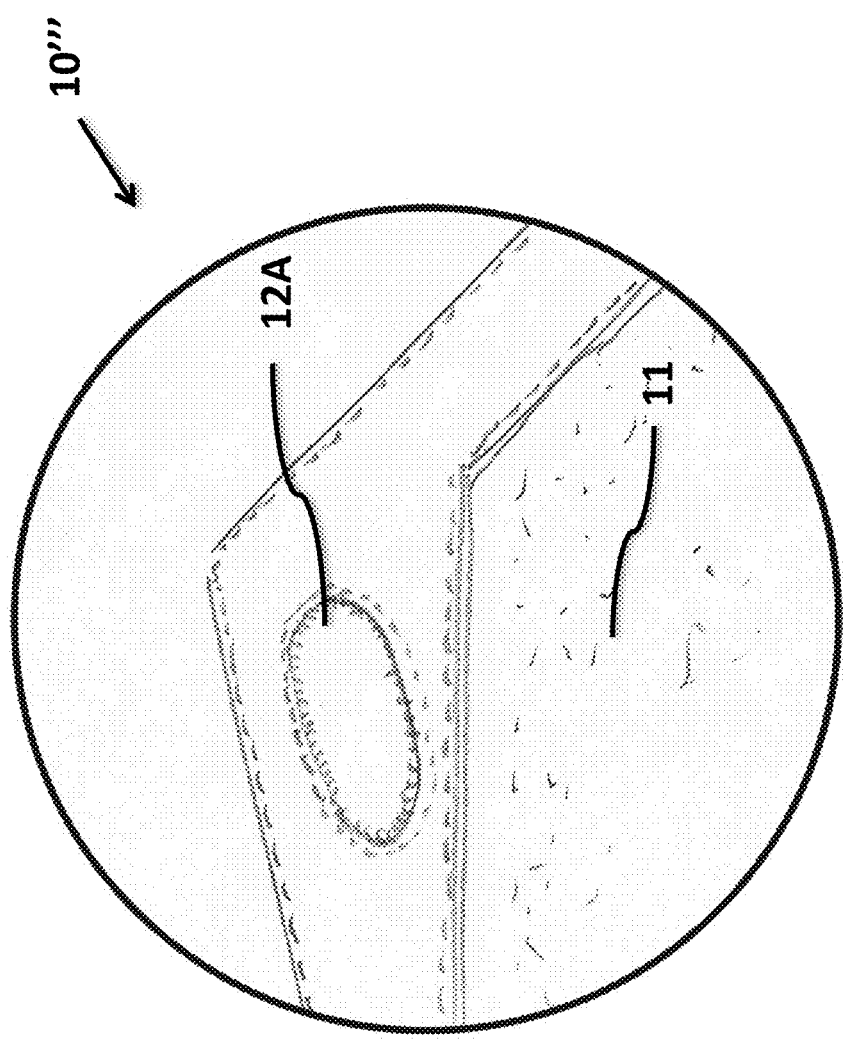
FIG. 16E is a first perspective view of stitches made about the inside perimeter of a hand/foot-insertable aperture formed in isometric-exercise towel of FIGS. 13A and 13B, using the CNC fabric sewing machine table illustrated in FIG. 16D.

FIGS. 16D and 16E show stitches made about the inside perimeter of a hand/foot-insertable aperture formed in isometric-exercise towel 10''' of FIGS. 13A and 13B, using the CNC fabric sewing machine table 30 illustrated in FIG. 16C.

Specification of Portable Isometric Exercise System of the Present Invention

Figure 17:
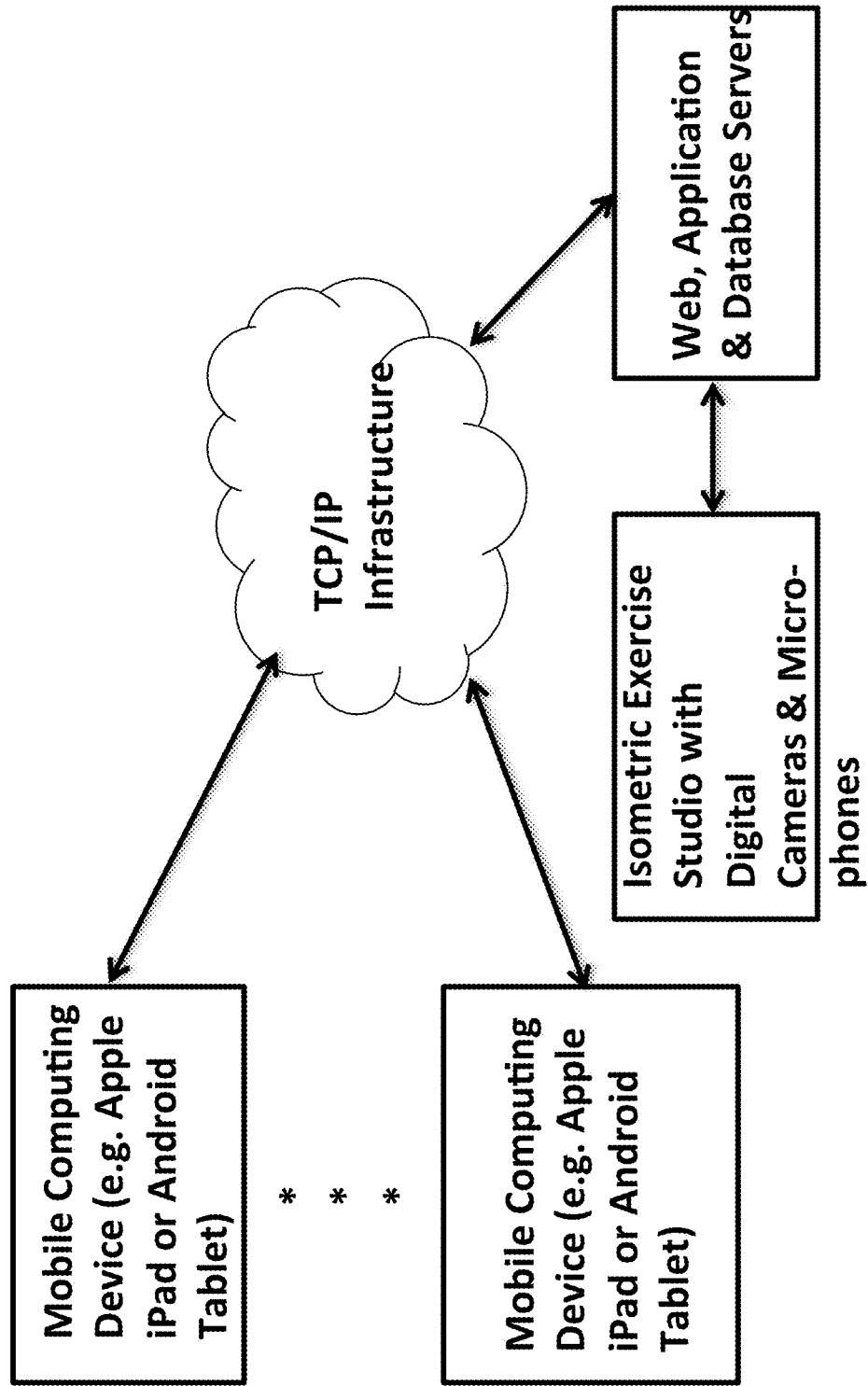
FIG. 17 is a schematic presentation of the portable Web-based video isometric exercise communication and presentation network of the present invention shown comprising the TCP/IP infrastructure of the Internet, one or more Web-based video servers (e.g. web, application and database servers), a remote web-based studio subsystem (including high-definition or HD video cameras, microphones, video-encoders and application and database servers) for creating and broadcasting video-based isometric exercise routines and workouts over the network, and a plurality of mobile web-based computing devices such as Apple® IPad devices, Android® tablet computers and other mobile computing devices supporting playback of downloaded or transmitted video-based isometric exercise routines and workouts from the studio subsystem.

FIG. 17 shows the portable Web-based isometric-exercise video communication and presentation network of the present invention comprising the following network components: the TCP/IP infrastructure of the Internet; one or more Web-based video servers (e.g. web, application and database servers); a remote web-based studio subsystem (including HD video cameras, microphones, video encoders and application and database servers) for creating and broadcasting video-based isometric exercise routines and workouts over the network; and a plurality of mobile web-based computing devices such as Apple® IPad devices, Android® tablet computers and other mobile computing devices supporting playback of downloaded or transmitted video-based isometric exercise routines and workouts from the studio subsystem, as illustrated in FIGS. 18 through 34.

These video-based isometric exercise workouts, illustrated in FIGS. 18 through 34, consists a set of carefully organized exercises, carried out using the isometric towel of the present invention, can be streamed live if sufficient data communication bandwidth is available to the user, or played locally from video files stored on the Apple® iPad device itself, as the case may be. In either case, the user may use such a portable display device and video isometric exercise network of the present invention to display isometric exercise routines, in a choreographed manner, with or without motivational music, to inspire and guide one or more users through a daily exercise routine using the isometric exercise towel of the present invention, as illustrated in FIGS. 18 through 34.

In the case of displaying live video streaming exercises, the user's mobile computing device will typically run a native or web-based application that presents a graphical user interface (GUI) on its LCD screen showing various user selectable programming/operating options, such as, for example: select level of exercise experience; select type of exercise instructor; select the kind of background of music desired during exercise; request user feedback after each isometric exercise; display user scoreboard and targets; and the like. Such video-based isometric exercise routines and workouts may be performed by an instructor in a classroom setting within the studio, involving the exercise instructor performing the workout alone, and possibly with one or more students, for motivational purposes. The isometric-exercise application running on the mobile computing device can be adapted to support currently available social media applications such as Facebook, and others well known in the art, to involve friends, associates and others into the isometric exercise experience.

Specification Methods of Isometric Exercise Using the Isometric-Exercise Towel of the Present Invention The following isometric exercises illustrated in FIGS. 18 through 34 can be performed using any isometric-exercise towel of the present invention 10, 10', 10" and/or 10'". Preferably, the video-based isometric-exercise presentation network shown in FIG. 17 will be used, although this is not necessary to practice the methods of the isometric exercise according to the principles of the present invention. The isometric exercise videos delivered and presented by this network will include isometric exercises illustrated in FIGS. 18 through 34, displayed on portable computing devices such as Apple® iPads available to individuals at their place of exercise where they use the isometric exercise towel of the present invention while viewing isometric exercise videos distributed by the network of the present invention.

For purposes of illustration only, the isometric-exercise towel 10 of the first illustration embodiment is shown and used in the following exercise illustrations. However, it is understood that any of the other embodiments of the present invention may be used with equal results.

FIG. 18 shows a door hook 60 being used to store the isometric-exercise towel of the present invention 10, 10', 10" and/or 10'". FIG. 19 shows a person using the door hook 61 to perform a first isometric exercise using the isometric-exercise towel of the present invention.

FIG. 20 shows a person using the top surface of a door 60 to perform an isometric exercise using the isometric-exercise towel of the present invention.

Figure 21:
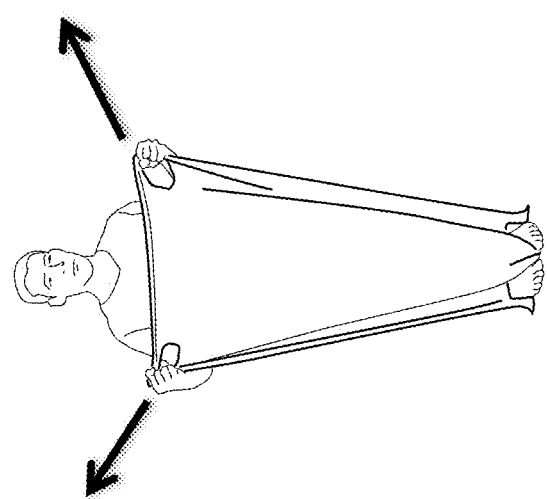
FIG. 21 is a graphical illustration of a GUI screen showing a person inserting his/her two feet within the lower pair of hand/foot-insertable apertures in the isometric-exercise towel of the present invention, and his two hands inserted within the upper hand/foot-insertable apertures thereof, so as to perform an isometric exercise using the same by stretching the isometric-towel in the directions indicated by the force vectors present in the graphical illustration.

FIG. 21 shows a person inserting his/her two feet within the lower pair of hand/foot-insertable apertures in the isometric-exercise towel of the present invention, and his two hands inserted within the upper hand/foot-insertable apertures thereof, so as to perform an isometric exercise using the same by stretching the isometric-towel in the directions indicated by the force vectors present in the graphical illustration.

Figure 22:
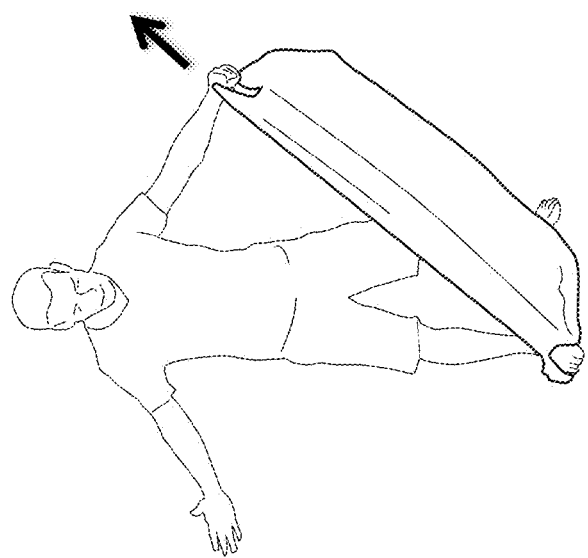
FIG. 22 is a graphical illustration of a GUI screen showing a person inserting one foot within the lower pair of folded hand/foot-insertable apertures in the isometric-exercise towel of the present invention, arranged in a longitudinally folded configuration, while his left hand is inserted within the upper folded pair of hand/foot-insertable apertures thereof, so as to perform an isometric exercise using the same by stretching the isometric-towel in a direction indicated by the force vector present in the graphical illustration.

FIG. 22 shows a person inserting one foot within the lower pair of folded hand/foot-insertable apertures in the isometric-exercise towel of the present invention, arranged in a longitudinally folded configuration, while his left hand is inserted within the upper folded pair of hand/foot-insertable apertures thereof, so as to perform an isometric exercise using the same by stretching the isometric-towel in a direction indicated by the force vector present in the graphical illustration.

Figure 23:
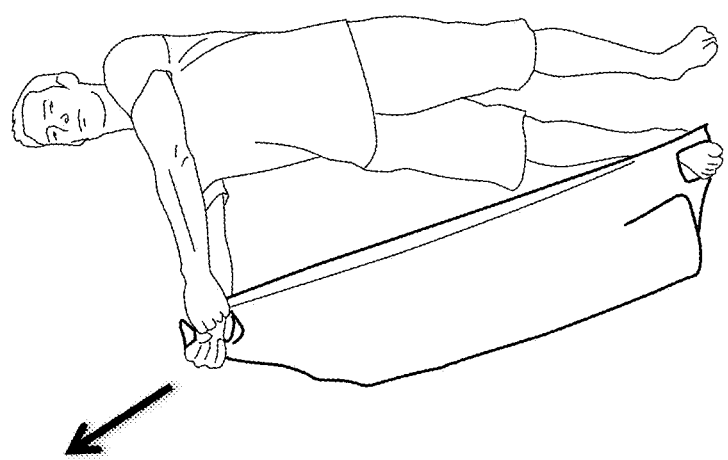
FIG. 23 is a graphical illustration of a GUI screen showing a person inserting one foot within the lower pair of folded hand/foot-insertable apertures in the isometric-exercise towel of the present invention, arranged in a folded configuration, while both his left and right hands are inserted within the upper folded pair of hand/foot-insertable apertures thereof, so as to perform an isometric exercise using the same by stretching the a directions indicated by the force vector present in the graphical illustration.

FIG. 23 shows a person inserting one foot within the lower pair of folded hand/foot-insertable apertures in the isometric-exercise towel of the present invention, arranged in a folded configuration, while both his left and right hands are inserted within the upper folded pair of hand/foot-insertable apertures thereof, so as to perform an isometric exercise using the same by stretching the a directions indicated by the force vector present in the graphical illustration.

Figure 24:
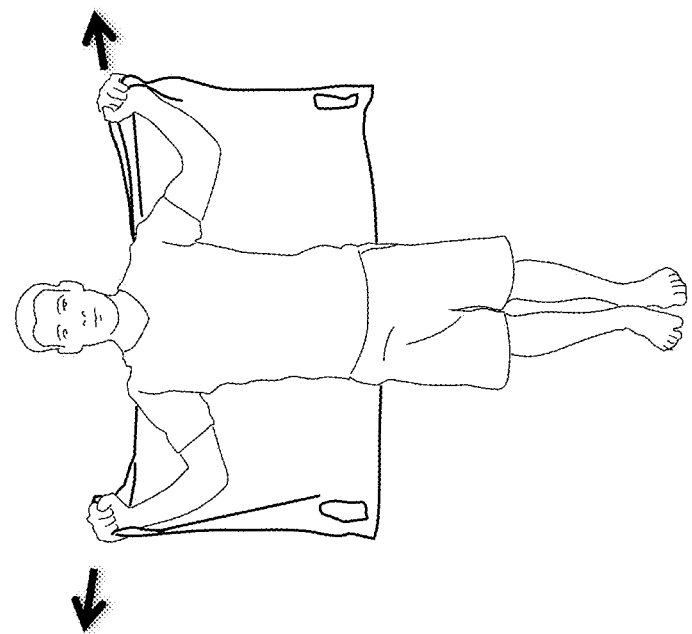
FIG. 24 is a graphical illustration of a GUI screen showing a person inserting one his left hand within one hand/foot-insertable aperture in the isometric-exercise towel of the present invention, while his right hand is inserted within the opposing hand/foot-insertable aperture and the towel is draped behind his shoulders, so as to perform an isometric exercise using the same by stretching the isometric-towel in the directions indicated by the force vectors present in the graphical illustration, while his arms are stretched horizontally.

FIG. 24 shows a person inserting one his left hand within one hand/foot-insertable aperture in the isometric-exercise towel of the present invention, while his right hand is inserted within the opposing hand/foot-insertable aperture and the towel is draped behind his shoulders, so as to perform an isometric exercise using the same by stretching the isometric-towel in the directions indicated by the force vectors present in the graphical illustration, while his arms are stretched horizontally.

Figure 25:
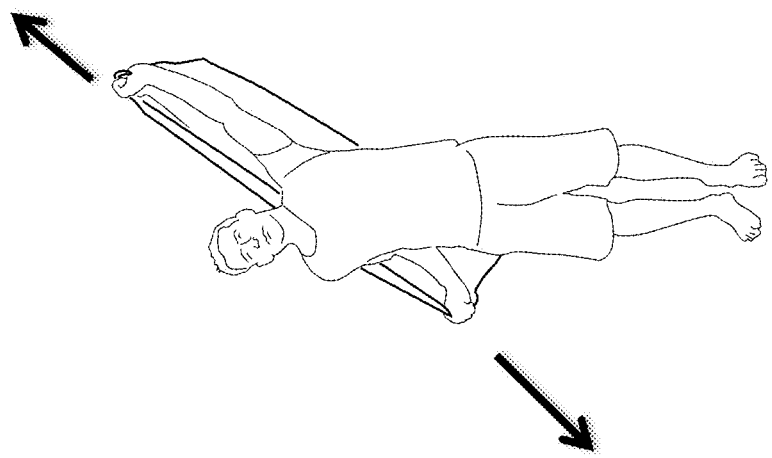
FIG. 25 is a graphical illustration of a GUI screen showing a person inserting one his left hand within one hand/foot-insertable aperture in the isometric-exercise towel of the present invention, while his right hand is inserted within the opposing hand/foot-insertable aperture and the towel is draped behind his shoulders, so as to perform an isometric exercise using the same by stretching the isometric-towel in the directions indicated by the force vectors present in the graphical illustration, while his arms are stretched diagonally, as shown.

FIG. 25 shows a person inserting one his left hand within one hand/foot-insertable aperture in the isometric-exercise towel of the present invention, while his right hand is inserted within the opposing hand/foot-insertable aperture and the towel is draped behind his shoulders, so as to perform an isometric exercise using the same by stretching the isometric-towel in the directions indicated by the force vectors present in the graphical illustration, while his arms are stretched diagonally, as shown.

Figure 26:
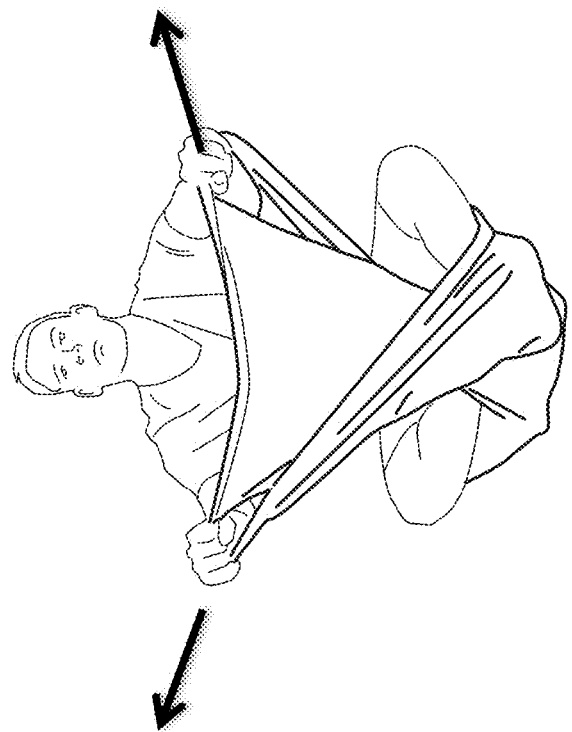
FIG. 26 is a graphical illustration of a GUI screen showing a person sitting down with his legs crossed and upon one longitudinal end of the isometric-exercise towel of the present invention, while his left and right hands are inserted within the pair of opposing hand/foot-insertable apertures on the opposing end of the isometric-exercise towel of the present invention, so as to perform an isometric exercise using the same by lifting the opposing end of the isometric-exercise towel and stretching it in the directions indicated by the force vectors present in the graphical illustration.

FIG. 26 shows a person sitting down with his legs crossed and upon one longitudinal end of the isometric-exercise towel of the present invention, while his left and right hands are inserted within the pair of opposing hand/foot-insertable apertures on the opposing end of the isometric-exercise towel of the present invention, so as to perform an isometric exercise using the same by lifting the opposing end of the isometric-exercise towel and stretching it in the directions indicated by the force vectors present in the graphical illustration.

Figure 27:
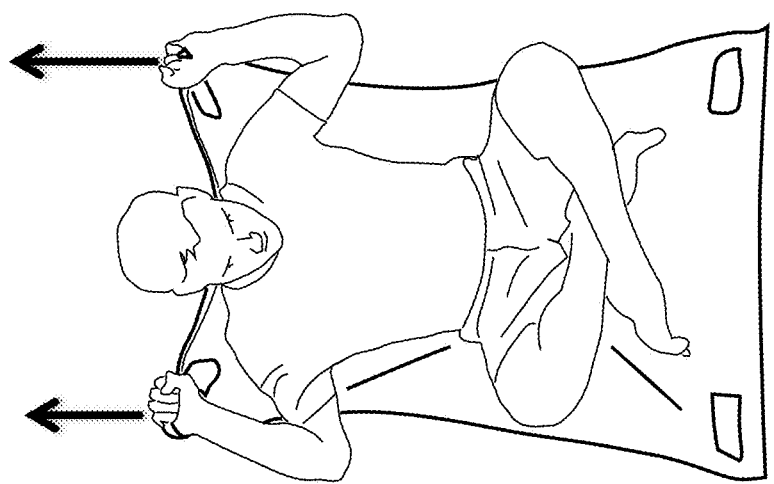
FIG. 27 is a graphical illustration of a GUI screen showing a person sitting down with his legs cross and sitting in the middle of the isometric-exercise towel of the present invention, while the person's pair of left and right hands are inserted within the pair of hand/foot-insertable apertures on one longitudinal end of the isometric-exercise towel of the present invention pulled up from behind the back of the person, so as to perform an isometric exercise using the same by stretching the isometric-towel in the directions indicated by the force vectors present in the graphical illustration.

FIG. 27 shows a person sitting down with his legs cross and sitting in the middle of the isometric-exercise towel of the present invention, while the person's pair of left and right hands are inserted within the pair of hand/foot-insertable apertures on one longitudinal end of the isometric-exercise towel of the present invention pulled up from behind the back of the person, so as to perform an isometric exercise using the same by stretching the isometric-towel in the directions indicated by the force vectors present in the graphical illustration.

Figure 28:
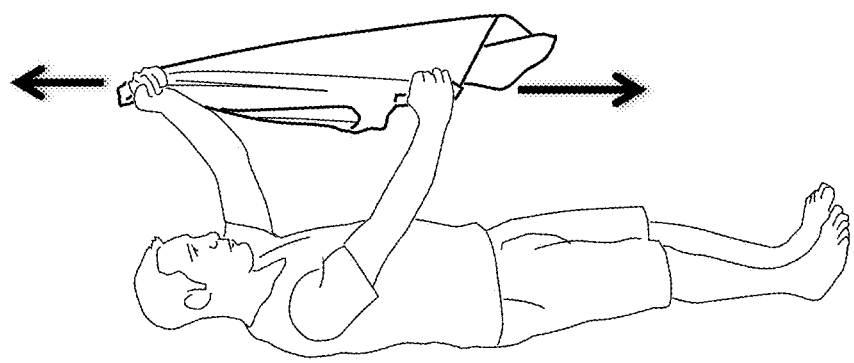
FIG. 28 is a graphical illustration of a GUI screen showing a person inserting his left hand within one hand/foot-insertable aperture in the isometric-exercise towel of the present invention in its latitudinally-folded configuration, while his right hand is inserted within the other hand/foot-insertable aperture on the same side of the towel, so as to perform an isometric exercise using the same by stretching the isometric-towel in the directions indicated by the force vectors present in the graphical illustration.

FIG. 28 shows a person inserting his left hand within one hand/foot-insertable aperture in the isometric-exercise towel of the present invention in its latitudinally-folded configuration, while his right hand is inserted within the other hand/foot-insertable aperture on the same side of the towel, so as to perform an isometric exercise using the same by stretching the isometric-towel in the directions indicated by the force vectors present in the graphical illustration.

Figure 29:
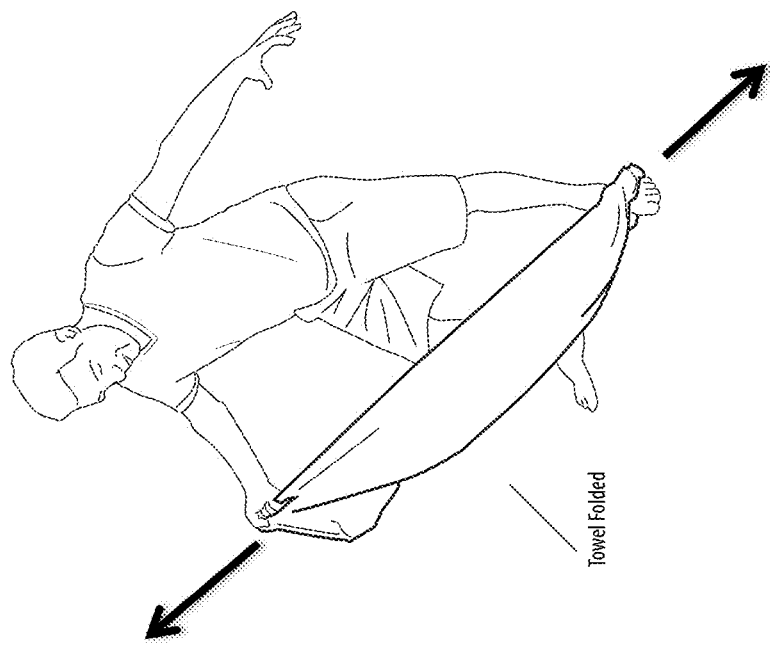
FIG. 29 is a graphical illustration of a GUI screen showing a person inserting right hand within the first pair of folded hand/foot-insertable apertures in the isometric-exercise towel of the present invention, arranged in a latitudinally-folded configuration, while his left foot is inserted within the lower folded pair of hand/foot-insertable apertures thereof, so as to perform an isometric exercise using the same by stretching the isometric-towel in a direction indicated by the force vector present in the graphical illustration.

FIG. 29 shows a person inserting right hand within the first pair of folded hand/foot-insertable apertures in the isometric-exercise towel of the present invention, arranged in a latitudinally-folded configuration, while his left foot is inserted within the lower folded pair of hand/foot-insertable apertures thereof, so as to perform an isometric exercise using the same by stretching the isometric-towel in a direction indicated by the force vector present in the graphical illustration.

Figure 30:
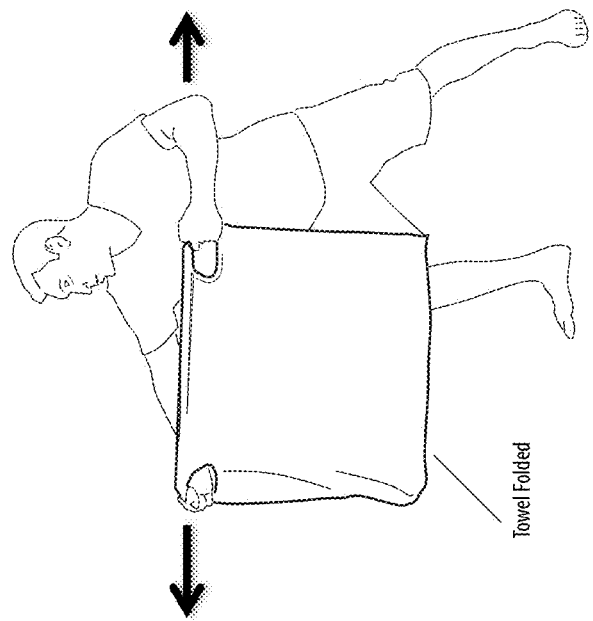
FIG. 30 is a graphical illustration of a GUI screen showing a person inserting left hand within the first pair of folded hand/foot-insertable apertures in the isometric-exercise towel of the present invention, arranged in a latitudinally folded configuration, while right left hand is inserted within the upper folded pair of hand/foot-insertable apertures thereof, so as to perform an isometric exercise using the same by stretching the isometric-towel in a direction indicated by the force vector present in the graphical illustration.

FIG. 30 shows a person inserting left hand within the first pair of folded hand/foot-insertable apertures in the isometric-exercise towel of the present invention, arranged in a latitudinally folded configuration, while right left hand is inserted within the upper folded pair of hand/foot-insertable apertures thereof, so as to perform an isometric exercise using the same by stretching the isometric-towel in a direction indicated by the force vector present in the graphical illustration.

Figure 31:
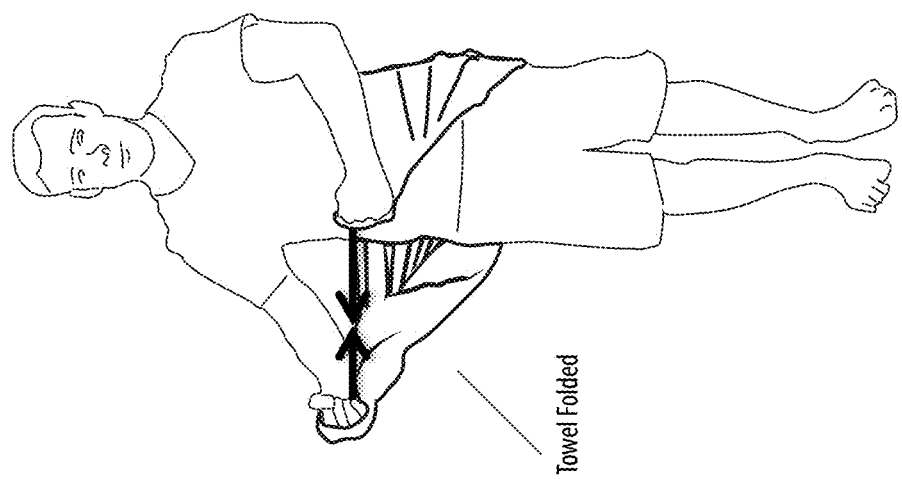
FIG. 31 is a graphical illustration of a GUI screen showing a person inserting left hand within the first pair of folded hand/foot-insertable apertures in the isometric-exercise towel of the present invention, arranged in a longitudinally folded configuration, while his right hand is inserted within the upper folded pair of hand/foot-insertable apertures thereof, as the isometric-exercise towel is wrapped around the person's rear waist region, so as to perform an isometric exercise using the same by stretching the isometric-towel in a direction indicated by the force vector present in the graphical illustration.

FIG. 31 shows a person inserting left hand within the first pair of folded hand/foot-insertable apertures in the isometric-exercise towel of the present invention, arranged in a longitudinally-folded configuration, while his right hand is inserted within the upper folded pair of hand/foot-insertable apertures thereof, as the isometric-exercise towel is wrapped around the person's rear waist region, so as to perform an isometric exercise using the same by stretching the isometric-towel in a direction indicated by the force vector present in the graphical illustration.

Figure 32:
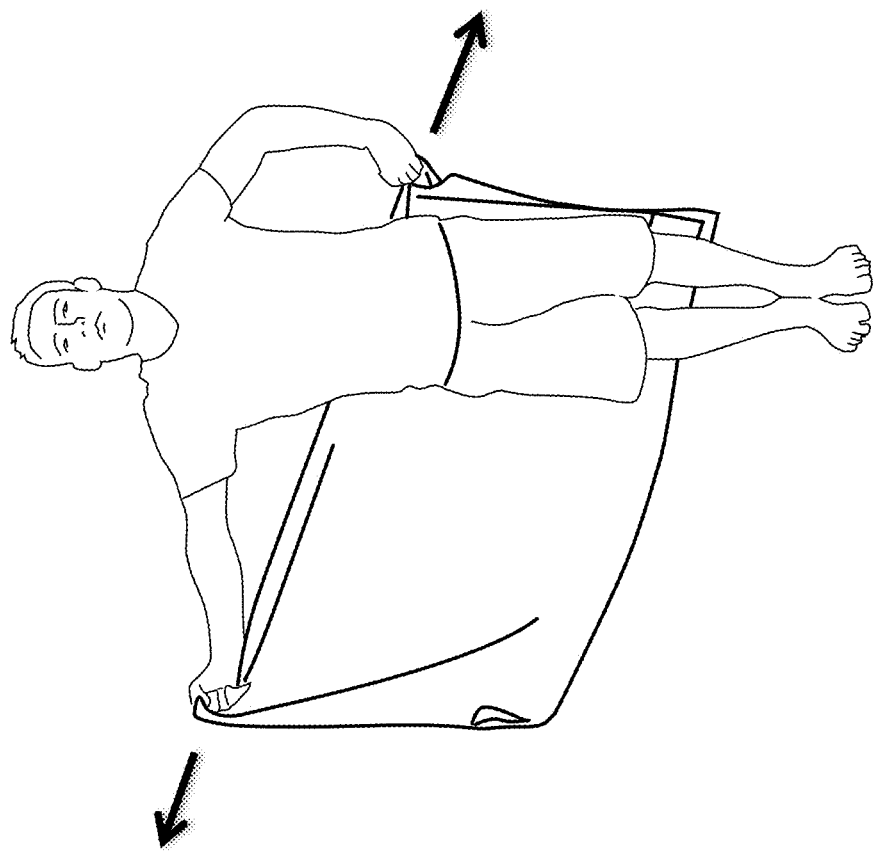
FIG. 32 is a graphical illustration of a GUI screen showing a person inserting one hand within the first pair of hand/foot-insertable apertures in the isometric-exercise towel of the present invention, while his left hand is inserted within the upper folded pair of hand/foot-insertable apertures thereof, as the towel is wrapped behind the person's rear waist region, so as to perform an isometric exercise using the same by stretching the isometric-towel in a direction indicated by the force vector present in the graphical illustration.

FIG. 32 shows a person inserting one hand within the first pair of hand/foot-insertable apertures in the isometric-exercise towel of the present invention, while his left hand is inserted within the upper folded pair of hand/foot-insertable apertures thereof, as the towel is wrapped behind the person's rear waist region, so as to perform an isometric exercise using the same by stretching the isometric-towel in a direction indicated by the force vector present in the graphical illustration.

FIG. 33 shows a person inserting both hands within the first pair of folded hand/foot-insertable apertures in the isometric-exercise towel of the present invention, while kneeling on the middle region of the isometric-exercise towel, as the person's feet are inserted within the opposing pair of hand/foot-insertable apertures thereof, so as to perform an isometric exercise using the same by stretching the isometric-towel in a direction indicated by the force vector present in the graphical illustration.

FIG. 34 shows a person inserting his right hand within the hand/foot-insertable aperture in one end of the isometric-exercise towel of the present invention, while his left hand is inserted within the opposing hand/foot-insertable aperture, while the isometric-exercise towel is suspended behind the person's head, so as to perform an isometric exercise using the same by stretching the isometric-towel in a direction indicated by the force vector present in the graphical illustration.

In alternative embodiments, each isometric-exercise towel of the present invention may be have embroidery reflecting membership to a particular health club, business organization, educational institution (e.g. college) or other social organization identified by a logo, trademark, service-mark or other form of graphics significant source of origin. Further, each isometric-exercise towel of the present invention may bear silk-screen printing of selected graphics, logos, messaging and the like, well known in the silk-screening arts.

Also, the terry cloth fabric and canvas material of the isometric-exercise towel may be treated with antimicrobial and antifungal agents so as to make them more resistant to growth of microbes (e.g. bacteria, fungi, viruses, and parasites) during normal use in expected exercise environments. The fabric material can be machine washed (i.e. machine washable) and treated to resist the formation of wrinkles during washings (i.e. to be wrinkle-resistant or wrinkle free). These and other variations and modifications will come to mind in view of the present invention disclosure.

While several modifications to the illustrative embodiments have been described above, it is understood that various other modifications to the illustrative embodiment of the present invention will readily occur to persons with ordinary skill in the art. All such modifications and variations are deemed to be within the scope and spirit of the present invention as defined by the accompanying Claims to Invention.

What is claimed is:

1. An isometric-exercise towel for use in performing isometric exercises using the hands and feet of a person performing said isometric exercises, said isometric-exercise towel comprising:

a rectangular-shaped layer of fabric material having moisture-wicking characteristics, four corner regions, a pair of opposing ends, a pair of side edges extending between said four corner regions and said opposing ends;

four hand/foot-insertable apertures formed in said four corner regions of said rectangular-shaped layer of fabric material, and a pair of hand/foot-insertable apertures formed along said side edges between said opposing ends of said rectangular-shaped layer of fabric material; and multiple pieces of flexible canvas material arranged about the perimeter of said rectangular-shaped layer of fabric material, and stitched together, for reinforcing and strengthening said opposing ends, said side edges and said four corner regions of said rectangular-shaped layer of fabric material, in which said hand/foot-insertable apertures are formed in said isometric-exercise towel;

wherein each said hand/foot-insertable aperture has side inner perimeter surfaces and is reinforced with double stitching about said side inner perimeter surfaces of said hand/foot-insertable aperture;

wherein said isometric-exercise towel has a longitudinal axis extending between said opposing ends, and a latitudinal axis extending between said pair of side edges;

wherein said isometric towel has an unfolded configuration, a latitudinal folded configuration, and a longitudinal folded configuration;

wherein when arranged in said unfolded configuration, said isometric-exercise towel is unfolded along its longitudinal and latitudinal axes, and said hand/foot-insertable apertures are available for insertion of the person's hands and/or feet during isometric exercise;

wherein when arranged in said latitudinal folded configuration, said isometric-exercise towel is folded along its latitudinal axis, two sets of hand/foot-insertable apertures are spatially aligned along said opposing ends, for insertion of the person's hands and/or feet during isometric exercise;

wherein when arranged in said longitudinal folded configuration, said isometric-exercise towel is folded along its longitudinal axis, and three sets of hand/foot-insertable apertures are spatially aligned along said side edges for insertion of the person's hands and/or feet during isometric exercise; and wherein when using said isometric-exercise towel in one of said configurations, one hand or one foot of a person, or both hands or both feet of said person, are inserted within any one of said hand/foot-insertable apertures formed in said isometric-exercise towel so as to perform an isometric exercise by said person using said hands and/or feet to exert forces against the side inner perimeter surfaces of said hand/foot-insertable apertures in an outwardly and isometric manner, while said multiple pieces of canvas material stitched together provide reinforcement and strength between adjacent sets of hand/foot-insertable apertures used by the hands and/or feet of said person during said one or more isometric exercises.

2. The isometric-exercise towel of claim 1, wherein said layer of fabric material is formed using a thick Terry cloth fabric with loops that is configured to absorb large amounts of moisture.

3. A method of exercising the body of a person having two feet and a pair of hands using said isometric-exercise towel of claim 1, said method comprising the steps of:
(a) the person inserting his/her two feet within a lower pair of hand/foot-insertable apertures of said four hand/foot-insertable apertures in said isometric-exercise towel, and
(b) said person inserting his/her two hands within an upper pair of hand/foot-insertable apertures of said four hand/foot-insertable apertures in said isometric-exercise towel; and
(c) performing an isometric exercise by stretching said isometric-exercise towel between said hands and said feet in outward directions in an isometric manner.

4. A method of exercising the body of a person having two feet and a pair of hands using said isometric-exercise towel of claim 1, said method comprising the steps of:
(a) the person inserting one foot within a lower pair of folded hand/foot-insertable apertures of said four hand/foot-insertable apertures in said isometric-exercise towel when arranged in said longitudinal folded configuration;
(b) while inserting a left hand within an upper folded pair of said hand/foot-insertable apertures of said four hand/foot-insertable apertures; and
(c) then performing an isometric exercise by stretching said isometric-exercise towel in outward directions in an isometric manner.

5. A method of exercising the body of a person having two feet and a pair of hands using said isometric-exercise towel of claim 1, said method comprising the steps of:
(a) the person inserting one foot within a lower pair of folded hand/foot-insertable apertures of said four hand/foot-insertable apertures in said isometric-exercise towel when arranged in said longitudinal folded configuration;
(b) while inserting both left and right hands within an upper folded pair of said hand/foot-insertable apertures of said four hand/foot-insertable apertures; and
(c) performing an isometric exercise by stretching said isometric-exercise towel in outward directions in an isometric manner.

6. A method of exercising the body of a person having two feet and a pair of hands using said isometric-exercise towel of claim 1, said method comprising the steps of:
(a) the person inserting a left hand within one said hand/foot-insertable aperture of said four hand/foot-insertable apertures in said isometric-exercise towel;
(b) while inserting a right hand within the opposing hand/foot-insertable aperture of said four hand/foot-insertable apertures and said isometric-exercise towel is draped behind his/her shoulders; and
(c) performing an isometric exercise by stretching said isometric-exercise towel, while the person's arms are stretched horizontally in outward directions in an isometric manner.

7. A method of exercising the body of a person having two feet and a pair of hands using said isometric-exercise towel of claim 1, said method comprising the steps of:
(a) the person inserting a left hand within one hand/foot-insertable aperture of said four hand/foot-insertable apertures in said isometric-exercise towel;
(b) while inserting a right hand within the opposing hand/foot-insertable aperture of said four hand/foot-insertable apertures and said isometric-exercise towel is draped behind the person's shoulders; and
(c) performing an isometric exercise by stretching said isometric-exercise towel, while the person's arms are stretched diagonally in outward directions in an isometric manner.

8. A method of exercising the body of a person having two feet and a pair of hands using said isometric-exercise towel of claim 1, said method comprising the steps of:
(a) the person sitting down with legs crossed and upon one longitudinal end of the isometric-exercise towel;
(b) while inserting the person's left and right hands within a pair of said hand/foot-insertable apertures of said four hand/foot-insertable apertures on the opposing end of said isometric-exercise towel; and
(c) performing an isometric exercise by lifting the opposing end of said isometric-exercise towel and stretching it said isometric-exercise towel in outward directions in an isometric manner.

9. A method of exercising the body of a person having two feet and a pair of hands using said isometric-exercise towel of claim 1, said method comprising the steps of:
(a) the person sitting down with legs crossed and sitting in the middle of the isometric-exercise towel;
(b) while inserting the person's pair of left and right hands within a pair of hand/foot-insertable apertures of said four hand/foot-insertable apertures on one longitudinal end of said isometric-exercise towel pulled up from behind the back of said person; and
(c) performing an isometric exercise by stretching said isometric-exercise towel in outward directions in an isometric manner.

10. A method of exercising the body of a person having two feet and a pair of hands using said isometric-exercise towel of claim 1, said method comprising the steps of:
(a) the person inserting a left hand within one said hand/foot-insertable aperture in said isometric-exercise towel when arranged in said latitudinal folded configuration;
(b) while inserting the person's right hand within the other said hand/foot-insertable aperture of said four hand/foot-insertable apertures on the same side of said isometric-exercise towel; and (c) performing an isometric exercise by stretching said isometric-exercise towel in outward directions in an isometric manner.

11. A method of exercising the body of a person having two feet and a pair of hands using said isometric-exercise towel of claim 1, said method comprising the steps of:
   (a) the person inserting a right hand within a first pair of folded hand/foot-insertable apertures of said four hand/foot-insertable apertures in said isometric-exercise towel arranged in said latitudinal folded configuration;
   (b) while inserting a left foot within the lower folded pair of hand/foot-insertable apertures of said four hand/foot-insertable apertures in said isometric-exercise towel; and
   (c) performing an isometric exercise by stretching said isometric-exercise towel.

12. A method of exercising the body of a person having two feet and a pair of hands using said isometric-exercise towel of claim 1, said method comprising the steps of:
   (a) the person inserting a left hand within a first pair of folded hand/foot-insertable apertures of said four hand/foot-insertable apertures in said isometric-exercise towel arranged in said latitudinal folded configuration;
   (b) while inserting a right hand within an upper folded pair of hand/foot-insertable apertures of said four hand/foot-insertable apertures in said isometric-exercise towel; and
   (c) performing an isometric exercise by stretching said isometric-exercise towel in outward directions in an isometric manner.

13. A method of exercising the body of a person having two feet and a pair of hands using said isometric-exercise towel of claim 1, said method comprising the steps of:
   (a) the person inserting a left hand within a first pair of folded hand/foot-insertable apertures of said four hand/foot-insertable apertures in said isometric-exercise towel when arranged in said longitudinal folded configuration;
   (b) while inserting a right hand within an upper folded pair of hand/foot-insertable apertures of said four hand/foot-insertable apertures, as said isometric-exercise towel is wrapped around the person's rear waist region; and
   (c) performing an isometric exercise by stretching said isometric-exercise towel in outward directions in an isometric manner.

14. A method of exercising the body of a person having two feet and a pair of hands using said isometric-exercise towel of claim 1, said method comprising the steps of:
   (a) the person inserting one hand within a first pair of hand/foot-insertable apertures of said four hand/foot-insertable apertures in the isometric-exercise towel;
   (b) while inserting the other hand within an upper folded pair of said hand/foot-insertable apertures of said four hand/foot-insertable apertures, as said isometric-exercise towel is wrapped behind the person's rear waist region; and
   (c) performing an isometric exercise by stretching said isometric-exercise towel in outward directions in an isometric manner.

15. A method of exercising the body of a person having two feet and a pair of hands using said isometric-exercise towel of claim 1, said method comprising the steps of:
   (a) the person inserting both hands within a first pair of hand/foot-insertable apertures of said four hand/foot-insertable apertures in the isometric-exercise towel;
   (b) while kneeling on the middle region of said isometric-exercise towel, inserting the person's feet within the opposing pair of said hand/foot-insertable apertures of said four hand/foot-insertable apertures in said isometric-exercise towel; and
   (c) performing an isometric exercise by stretching said isometric-exercise towel in outward directions in an isometric manner.

16. A method of exercising the body of a person having two feet and a pair of hands using said isometric-exercise towel of claim 1, said method comprising the steps of:
   (a) the person inserting a right hand within said hand/foot-insertable aperture of said four hand/foot-insertable apertures in one end of said isometric-exercise towel;
   (b) while inserting a left hand within the opposing hand/foot-insertable aperture of said four hand/foot-insertable apertures in said isometric-exercise towel, while said isometric-exercise towel is suspended behind the person's head; and
   (c) performing an isometric exercise by stretching said isometric-exercise towel in outward directions in an isometric manner.

* * * * *